United States Patent
De Peretti et al.

(10) Patent No.: US 8,338,451 B2
(45) Date of Patent: Dec. 25, 2012

(54) **POLYSUBSTITUTED DERIVATIVES OF 2-HETEROARYL-6-PHENYLIMIDAZO[1,2-*A*] PYRIDINES, AND PREPARATION AND THERAPEUTIC USE THEREOF**

(75) Inventors: Danielle De Peretti, Paris (FR); Yannick Evanno, Paris (FR); Patrick Lardenois, Paris (FR); David Machnik, Paris (FR); Nathalie Rakotoarisoa, Paris (FR); Antonio Almario Garcia, Paris (FR)

(73) Assignee: Sanofi, Paris (FR)

( * ) Notice: Subject to any disclaimer, the term of this patent is extended or adjusted under 35 U.S.C. 154(b) by 72 days.

(21) Appl. No.: 12/881,815

(22) Filed: Sep. 14, 2010

(65) Prior Publication Data

US 2011/0065727 A1    Mar. 17, 2011

Related U.S. Application Data

(63) Continuation of application No. PCT/FR2009/000303, filed on Mar. 20, 2009.

(30) Foreign Application Priority Data

Mar. 21, 2008 (FR) ..................................... 08 01584

(51) Int. Cl.
*A61K 31/44* (2006.01)
*C07D 513/02* (2006.01)
(52) U.S. Cl. ......... 514/300; 514/256; 546/121; 546/311
(58) Field of Classification Search .................. 514/256, 514/300; 546/121, 311
See application file for complete search history.

(56) References Cited

U.S. PATENT DOCUMENTS

| | | | |
|---|---|---|---|
| 7,087,757 B2 * | 8/2006 | Breitenbucher et al. ...... | 546/121 |
| 7,902,219 B2 | 3/2011 | Peyronel et al. | |
| 2009/0253735 A1 | 10/2009 | Almario Garcia et al. | |
| 2010/0168155 A1 | 7/2010 | El Ahmad et al. | |
| 2011/0065699 A1 | 3/2011 | De Peretti et al. | |
| 2011/0065700 A1 | 3/2011 | De Peretti et al. | |
| 2011/0065745 A1 | 3/2011 | De Peretti et al. | |

FOREIGN PATENT DOCUMENTS

| | | |
|---|---|---|
| FR | 2 903 105 | 1/2008 |
| FR | 2 903 107 | 1/2008 |
| WO | WO 2004/076412 A2 | 9/2004 |
| WO | WO 2008/034974 A1 | 3/2008 |

OTHER PUBLICATIONS

International Search Report for WO2009/144395 dated Dec. 3, 2009.
U.S. Appl. No. 12/881,827—Non-Final Office Action dated Sep. 22, 2011.
U.S. Appl. No. 12/881,805—Non-Final Office Action dated Sep. 7, 2011.
Gudmundsson et al, An Improved Synthesis of 2-Chlorinated Imidazo[1,2-a]pyridines and the Application of this Procedure for the Synthesis of Several New Polychlorinated Imidazo[1,2-a]pyridines, Syn. Comm., 1997 (27) 10, pp. 1763-1775.
Barder et al, Catalysts for Suzuki-Miyaura Coupling Processes: Scope and Studies of the Effect of Ligand Structure, JACS, 2005(127) pp. 4685-4696.
Cai et al, Synthesis and Structure-Affinity Relationships of New 4-(6-Iodo-H-imidazo[1,2-a] pyridin-2-yl)-N-dimethylbenzeneamine Derivatives as Ligands for Human b-Amyloid plaques, J. Med. Chem., 2007 (50) pp. 4746-4758.
DiMauro et al, Microwave-Assisted Preparation of Fused Bicyclic Heteroaryl Boronates: Application in One-Pot Suzuki Couplings, JOC, 2006(71) pp. 3959-5962.
Enguehard at al, (Hetero)Arylation of 6-Halogenoimidazo [1,2-a]Pyridines Differently Substituted at C(2): Influence of the 2-Substituent on the Suzuki Cross-Coupling Reaction, Helvetica Chimica Acta, 2001(84) pp. 3610-3615.
Fisher et al, Imidazo[1,2-a]pyridine Anthelmintic and Antifungal Agents, J.Med.Chem., 1972 (15) 9, pp. 982-985.

* cited by examiner

*Primary Examiner* — Rei-tsang Shiao
(74) *Attorney, Agent, or Firm* — Kelly L. Bender

(57) ABSTRACT

Compounds of formula (I):

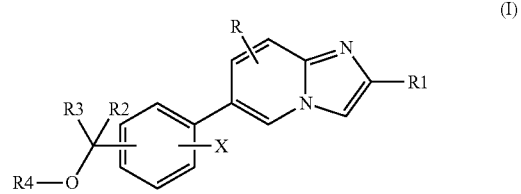

wherein R, $R_1$, $R_2$, $R_3$, $R_4$ and X are as defined in the disclosure, or an acid addition salt thereof, and the therapeutic use and process of synthesis thereof.

14 Claims, No Drawings

POLYSUBSTITUTED DERIVATIVES OF 2-HETEROARYL-6-PHENYLIMIDAZO[1,2-A]PYRIDINES, AND PREPARATION AND THERAPEUTIC USE THEREOF

This application is a continuation of International application No. PCT/FR2009/000303 filed Mar. 20, 2009, which is incorporated herein by reference in its entirety; which claims the benefit of priority of French Patent Application No. 0801584 filed Mar. 21, 2008.

The present invention relates to polysubstituted 2-heteroaryl-6-phenylimidazo[1,2-a]pyridine derivatives, to the preparation thereof and to the therapeutic use thereof in the treatment or prevention of diseases involving Nurr-1 nuclear receptors, also known as NR4A2, NOT, TINUR, RNR-1 and HZF3.

The subject of the present invention is also the compounds of formula (I):

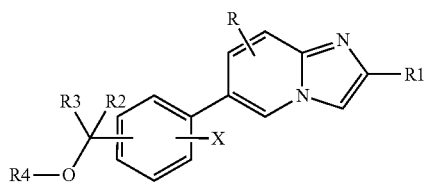

in which:

$R_1$ represents:
  a heteroaryl or heterocyclic group, it being possible for this group to be optionally substituted with one or more atoms or groups chosen, independently of one another, from the following atoms or groups: halogen, $(C_1-C_{10})$alkyl, halo$(C_1-C_{10})$alkyl, $(C_1-C_{10})$alkoxy, halo$(C_1-C_{10})$alkoxy, oxo, $(C_1-C_{10})$thioalkyl, —S(O)$(C_1-C_{10})$alkyl, —S(O)$_2$($C_1-C_{10}$-alkyl), hydroxyl, cyano, nitro, hydroxy$(C_1-C_{10})$alkylene, NRaRb$(C_1-C_{10})$alkylene, $(C_1-C_{10})$alkoxy$(C_1-C_{10})$alkyleneoxy, NRaRb, CONRaRb, SO$_2$NRaRb, NRcCORd, OC(O)NRaRb, OCO$(C_1-C_{10})$alkyl, NRcC(O)ORe, NRcSO$_2$Re, aryl$(C_1-C_{10})$alkylene, monocyclic heteroaryl or aryl, the monocyclic heteroaryl or aryl being optionally substituted with one or more substituents chosen from a halogen, and a $(C_1-C_{10})$alkyl, halo$(C_1-C_{10})$alkyl, $(C_1-C_{10})$alkoxy, halo$(C_1-C_{10})$alkoxy, NRaRb, hydroxyl, oxo, nitro, cyano or OCO$(C_1-C_{10})$alkyl group, and R1 is linked to the imidazo[1,2-a]pyridine by an aromatic carbon;

X represents from 1 to 4 substituents, which may be identical to or different from one another, chosen from hydrogen, a halogen, $(C_1-C_{10})$alkyl, $(C_1-C_{10})$alkoxy, NRaRb, nitro, cyano, it being possible for the $(C_1-C_{10})$alkyl group to be optionally substituted with one or more groups chosen from a halogen, $(C_1-C_{10})$alkoxy, $(C_1-C_{10})$haloalkoxy, NRaRb or hydroxyl;

R represents, at position 3, 5, 7 or 8 of the imidazo[1,2-a]pyridine, from 1 to 4 substituents, which may be identical to or different from one another, chosen from a hydrogen, a halogen, $(C_1-C_{10})$alkyl, halo$(C_1-C_{10})$alkyl, $(C_1-C_{10})$alkoxy;

$R_2$ and $R_3$ represent, independently of one another,
  a hydrogen atom,
  a $(C_1-C_{10})$alkyl group, optionally substituted with an Rf group;
  an aryl group, optionally substituted with one or more substituents chosen from a halogen, and a $(C_1-C_{10})$alkyl, halo$(C_1-C_{10})$alkyl, $(C_1-C_{10})$alkoxy, halo$(C_1-C_{10})$alkoxy, NRaRb, hydroxyl, nitro or cyano group;

$R_2$ and X can form, together with the carbon atoms which bear them, a carbon-based ring containing from 5 to 7 carbon atoms;

$R_4$ represents:
  a hydrogen atom;
  a $(C_1-C_{10})$alkyl group, optionally substituted by an Rf group;
  an aryl group, optionally substituted with one or more substituents chosen from a halogen, and a $(C_1-C_{10})$alkyl, halo$(C_1-C_{10})$alkyl, $(C_1-C_{10})$alkoxy, halo$(C_1-C_{10})$alkoxy, NRaRb, hydroxyl, nitro, cyano, $(C_1-C_{10})$alkyl(CO)—, CONRaRb, NRcCORd, OC(O)NRaRb, OCO$(C_1-C_{10})$alkyl, NRcC(O)ORe or aryl group, the aryl being optionally substituted with one or more substituents chosen from a halogen, and a $(C_1-C_{10})$alkyl halo$(C_1-C_{10})$, alkyl, $(C_1-C_{10})$alkoxy, halo$(C_1-C_{10})$alkoxy, NRaRb, hydroxyl, nitro or cyano group;

Ra and Rb represent, independently of one another, a hydrogen atom or a $(C_1-C_{10})$alkyl, aryl$(C_1-C_{10})$alkylene or aryl group;

or Ra and Rb form, together with the nitrogen atom which bears them, an azetidine, pyrrolidine, piperidine, azepine, morpholine, thiomorpholine, piperazine or homopiperazine group, this group being optionally substituted with a $(C_1-C_{10})$alkyl, aryl or aryl$(C_1-C_{10})$alkylene group;

Rc and Rd represent, independently of one another, a hydrogen atom or a $(C_1-C_{10})$alkyl, aryl$(C_1-C_{10})$alkylene or aryl group, or Rc and Rd together form a $(C_2-C_5)$alkylene group;

Re represents a $(C_1-C_{10})$alkyl, aryl$(C_1-C_{10})$alkylene or aryl group, or Rc and Re together form a $(C_2-C_5)$alkylene group;

Rf represents a halogen atom, or a $(C_1-C_{10})$alkoxy, halo$(C_1-C_{10})$alkoxy, hydroxyl, cyano, NRaRb, C(O)NRaRb, NRcCORd, OC(O)NRaRb, OCO$(C_1-C_{10})$alkyl, NRcCOORe, SO$_2$NRaRb, NRcSO$_2$Re, aryl$(C_1-C_{10})$alkylene or aryl group, the aryl being optionally substituted with one or more substituents chosen from a halogen, and a $(C_1-C_{10})$alkyl, halo$(C_1-C_{10})$ alkyl, $(C_1-C_{10})$alkoxy, halo$(C_1-C_{10})$alkoxy, NRaRb, hydroxyl, nitro, cyano or OCO$(C_1-C_{10})$alkyl group;

in the form of a base or of an addition salt with an acid.

The compounds of formula (I) may comprise one or more asymmetrical carbon atoms. They may therefore exist in the form of enantiomers or of diastereoisomers. These enantiomers and diastereoisomers, and also mixtures thereof, including racemic mixtures, are part of the invention.

The compounds of formula (I) may exist in the form of bases or of addition salts with acids. Such addition salts are part of the invention.

These salts can be prepared with pharmaceutically acceptable acids, but the salts of other acids that are useful for example, for purifying or isolating the compounds of formula (I) are also part of the invention.

The compounds of formula (I) may also exist in the form of hydrates or of solvates, i.e. in the form of associations or of combinations with one or more water molecules or with a solvent. Such hydrates and solvates are also part of the invention.

In the context of the present invention:
  the term "a $(C_x-C_t)$ group" is intended to mean: a group comprising between x and t carbon atoms;
  the term "a halogen atom" is intended to mean: a fluorine, a chlorine, a bromine or an iodine;
  the term "an alkyl group" is intended to mean: a linear, branched or cyclic, saturated aliphatic group optionally substituted with a linear branched or cyclic, saturated alkyl group. By way of examples, mention may be made of methyl, ethyl, propyl, isopropyl, butyl, isobutyl, tert-butyl, cyclopropyl, cyclobutyl, cyclopentyl, cyclohexyl, methylcyclopropyl, cyclopropylmethyl, etc, groups;

the term "an alkylene group" is intended to mean: a divalent alkyl group;

the term "an alkoxy group" is intended to mean: an —O-alkyl radical wherein the alkyl group is as defined above;

the term "a haloalkyl group" is intended to mean: an alkyl group substituted with one or more halogen atoms, which may be identical or different. By way of examples, mention may be made of $CF_3$, $CH_2CF_3$, $CHF_2$ or $CCl_3$ groups;

the term "a haloalkoxy group" is intended to mean: an —O-alkyl radical wherein the alkyl group is as defined above and substituted with one or more halogen atoms, which may be identical or different. By way of examples, mention may be made of $OCF_3$, $OCHF_2$ or $OCCl_3$ groups;

the term "a thioalkyl group" is intended to mean: an S-alkyl radical wherein the alkyl group is as defined above;

the term "an aryl group" is intended to mean: a monocyclic or bicyclic aromatic group containing from 6 to 10 atoms. By way of examples of aryl groups, mention may be made of phenyl and naphthyl groups;

the term "a heteroaryl group" is intended to mean: a monocyclic or bicyclic aromatic group containing from 5 to 10 atoms, including from 1 to 4 heteroatoms chosen from N, O and S. By way of examples of heteroaryl groups, mention may be made of: pyrrole, furan, thiophene, pyrazole, imidazole, triazole, tetrazole, oxazole, isoxazole, oxadiazole, thiazole, isothiazole, thiadiazole, pyridine, pyrimidine, pyrazine, pyridazine, triazine, thienothiophene, furofuran, thienofuran, furopyrrole, thienopyrrole, pyrrolopyrrole, pyrroloisoxazole, furoisoxazole, thienoisoxazole, isoxazoloisoxazole, pyrrolooxazole, furooxazole, thienooxazole, oxazoloisoxazole, oxazolooxazole, pyrroloisothiazole, furoisothiazole, thienoisothiazole, isothiazoloisoxazole, isothiazolooxazole, isothiazoloisothiazole, pyrrolothiazole, furothiazole, thienothiazole, thiazolooxazole, thiazoloisoxazole, thiazoloisothiazole, thiazolothiazole, pyrrolopyrazole, furopyrazole, thienopyrazole, pyrazoloisoxazole, pyrazolooxazole, pyrazoloisothiazole, pyrazolothiazole, pyrazolopyrazole, pyrroloimidazole, furoimidazole, thienoimidazole, imidazoisoxazole, imidazooxazole, imidazoisothiazole, imidazothiazole, imidazopyrazole, imidazoimidazole, pyrrolooxadiazole, furooxadiazole, thienooxadiazole, pyrazolooxadiazole, imidazooxadiazole, furothiadiazole, thienothiadiazole, pyrrolothiadiazole, imidazothiadiazole, pyrazolothiadiazole, thienotriazole, pyrrolotriazole, furotriazole, oxazolotriazole, isoxazolotriazole, thiazolotriazole, isothiazolotriazole, pyrazolotriazole, imidazotriazole, indole, isoindole, benzimidazole, indazole, indolizine, benzofuran, isobenzofuran, benzothiophene, benzo[c]thiophene, pyrrolopyridine, imidazopyridine, pyrazolopyridine, triazolopyridine, tetrazolopyridine, pyrrolopyrimidine, imidazopyrimidine, pyrazolopyrimidine, triazolopyrimidine, pyrrolopyrazine, imidazopyrazine, pyrazolopyrazine, triazolopyrazine, pyrrolopyridazine, imidazopyridazine, pyrazolopyridazine, triazolopyridazine, pyrrolotriazine, imidazotriazine, pyrazolotriazine, furopyridine, furopyrimidine, furopyrazine, furopyridazine, furotriazine, oxazolopyridine, oxazolopyrimidine, oxazolopyrazine, oxazolopyridazine, isoxazolopyridine, isoxazolopyrimidine, isoxazolopyrazine, isoxazolopyridazine, oxadiazolopyridine, benzoxazole, benzisoxazole, benzoxadiazole, thienopyridine, thienopyrimidine, thienopyrazine, thienopyridazine, thienotriazine, thiazolopyridine, thiazolopyrimidine, thiazolopyrazine, thiazolopyridazine, isothiazolopyridine, isothiazolopyrimidine, isothiazolopyrazine, isothiazolopyridazine, thiadiazolopyridine, benzothiazole, benzoisothiazole, benzothiadiazole, benzotriazole, quinoline, isoquinoline, cinnoline, phthalazine, quinoxaline, quinazoline, naphthyridine, benzotriazine, pyridopyrimidine, pyridopyrazine, pyridopyridazine, pyridotriazine, pyrimidopyrimidine, pyrimidopyrazine, pyrimidopyridazine, pyrazinopyrazine, pyrazinopyridazine, pyridazinopyridazine.

the term "a heterocyclic group" is intended to mean: a bicyclic group containing from 9 to 10 atoms comprising from 1 to 4 heteroatoms chosen from N, O and S, one ring of which is aromatic and the other ring of which is saturated or partially saturated, each of the rings comprising at most only 2 heteroatoms. By way of examples of bicyclic groups, mention may be made of: benzodioxole, benzoxathiole, benzopyran, benzothiopyran, benzoxazine, benzothiazine, benzodioxine, benzothioxine, dioxolopyridine, oxathiolopyridine, pyranopyridine, thiopyranopyridine, oxazinopyridine, thiazinopyridine, dioxinopyridine, thioxinopyridine, dioxolopyrimidine, oxathiolopyrimidine, pyranopyrimidine, thiopyranopyrimidine, oxazinopyrimidine, thiazinopyrimidine, dioxinopyrimidine, thioxinopyrimidine, dioxolopyrazine, oxathiolopyrazine, pyranopyrazine, thiopyranopyrazine, oxazinopyrazine, thiazinopyrazine, dioxinopyrazine, thioxinopyrazine, dioxolopyridazine, oxathiolopyridazine, pyranopyridazine, thiopyranopyridazine, oxazinopyridazine, thiazinopyridazine, dioxinopyridazine, thioxinopyridazine, indole, isoindole, benzimidazole, indazole, indolizine, benzofuran, isobenzofuran, benzothiophene, benzo[c]thiophene, pyrrolopyridine, imidazopyridine, pyrazolopyridine, pyrrolopyrimidine, imidazopyrimidine, pyrazolopyrimidine, pyrrolopyrazine, imidazopyrazine, pyrazolopyrazine, pyrrolopyridazine, imidazopyridazine, pyrazolopyridazine, furopyridine, furopyrimidine, furopyrazine, furopyridazine, oxazolopyridine, oxazolopyrimidine, oxazolopyrazine, oxazolopyridazine, isoxazolopyridine, isoxazolopyrimidine, isoxazolopyrazine, isoxazolopyridazine, benzoxazole, benzisoxazole, benzoxadiazole, thienopyridine, thienopyrimidine, thienopyrazine, thienopyridazine, thiazolopyridine, thiazolopyrimidine, thiazolopyrazine, thiazolopyridazine, isothiazolopyridine, isothiazolopyrimidine, isothiazolopyrazine, isothiazolopyridazine, benzothiazole, benzoisothiazole, quinoline, isoquinoline, cinnoline, phthalazine, quinoxaline, quinazoline, naphthyridine, pyridopyrimidine, pyridopyrazine, pyridopyridazine, pyrimidopyrimidine, pyrimidopyrazine, pyrimidopyridazine, pyrazinopyrazine, pyrazinopyridazine, pyridazinopyridazine, one of the rings of these bicyclic groups being in saturated or partially saturated form, for example dihydrobenzofuran, tetrahydroquinoline, dihydrobenzoxazole or benzodioxole;

the term "an aromatic carbon" is intended to mean: a carbon which is included in an aromatic ring;

the term sulphur and nitrogen atoms may be in the oxidized state (N-oxide, sulphoxide, sulphone).

Among the compounds of formula (I) which are subjects of the invention, a first group of compounds is constituted of the compounds for which:

$R_1$ represents an isoxazolyl, pyridinyl, thiazolyl, quinolinyl, benzo[1,3]dioxolyl, indolyl, 1,2,3,4-tetrahydroquinolinyl, benzofuranyl, dihydrobenzofuranyl, dihydrobenzoxazolyl, furyl, thienyl, pyrrolo[2,3-b]pyridinyl, pyrimidinyl, benzothiazolyl, benzothiophenyl, benzimidazolyl, indazolyl, benzisoxazolyl, isoquinolinyl or pyrazolyl group;

it being possible for these groups to be optionally substituted with one or more atoms or groups chosen, independently of one another, from halogen, $(C_1-C_{10})$alkyl, oxo, NRaRb, $(C_1-C_{10})$alkoxy, aryl and CONRaRb;

Ra and Rb represent, independently of one another, a hydrogen atom or a $(C_1-C_{10})$alkyl group;

the other substituents being defined as above.

Among the compounds of formula (I) which are subjects of the invention, a second group of compounds is constituted of the compounds for which:

$R_1$ represents an isoxazolyl, pyridinyl, thiazolyl, quinolinyl, benzo[1,3]dioxolyl, indolyl, 1,2,3,4-tetrahydroquinolinyl, benzofuryl, dihydrobenzofuryl, dihydrobenzoxazolyl, furyl, thienyl, pyrrolo[2,3-b]pyridinyl, pyrimidinyl, benzothiazolyl, benzothiophenyl, benzimidazolyl, indazolyl, benzisoxazolyl, isoquinolinyl or pyrazolyl group;

it being possible for these groups to be optionally substituted with one or more atoms or groups chosen, independently of one another, from halogen, methyl, oxo, NRaRb, methoxy, ethoxy, phenyl, isopentyl and $CONHC(CH_3)_3$;

Ra and Rb represent, independently of one another, a hydrogen atom or a methyl group; the other substituents being defined as above.

Among the compounds of formula (I) which are subjects of the invention, a third group of compounds is constituted of the compounds for which:

X represents 1 or 2 hydrogen or halogen atoms; the other substituents being defined as above.

Among the compounds of formula (I) which are subjects of the invention, a fourth group of compounds is constituted of the compounds for which:

X represents 1 or 2 hydrogen or fluorine atoms;
the other substituents being defined as above.

Among the compounds of formula (I) which are subjects of the invention, a fifth group of compounds is constituted of the compounds for which:

R represents, at position 3, 5, 7 or 8 of the imidazo[1,2-a]pyridine, a hydrogen atom or a $(C_1-C_{10})$alkyl group;

the other substituents being defined as above.

Among the compounds of formula (I) which are subjects of the invention, a sixth group of compounds is constituted of the compounds for which:

R represents, at position 3, 5, 7 or 8 of the imidazo[1,2-a]pyridine, a hydrogen atom or a methyl group;

the other substituents being defined as above.

Among the compounds of formula (I) which are subjects of the invention, a seventh group of compounds is constituted of the compounds for which:

$R_2$ and $R_3$ represent, independently of one another, a hydrogen atom or a $(C_1-C_{10})$alkyl group;

the other substituents being defined as above.

Among the compounds of formula (I) which are subjects of the invention, an eighth group of compounds is constituted of the compounds for which:

$R_2$ and $R_3$ represent, independently of one another, a hydrogen atom or a methyl group;

the other substituents being defined as above.

Among the compounds of formula (I) which are subjects of the invention, a ninth group of compounds is constituted of the compounds for which:

$R_4$ represents a hydrogen atom, or a $(C_1-C_{10})$alkyl group optionally substituted with an Rf group;

Rf represents a $(C_1-C_{10})$alkoxy group;

the other substituents being defined as above.

Among the compounds of formula (I) which are subjects of the invention, a tenth group of compounds is constituted of the compounds for which:

$R_4$ represents a hydrogen atom, or a group chosen from methyl, butyl and methoxyethyl groups;

the other substituents being defined as above.

Among the compounds of formula (I) which are subjects of the invention, an eleventh group of compounds is constituted of the compounds for which:

the group

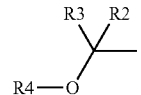

is at position 2, 3 or 4 of the phenyl which bears it;
the substituents being as defined above.

Among the compounds of formula (I) which are subjects of the invention, a twelfth group of compounds is constituted of the compounds for which:

$R_1$ represents an isoxazolyl, pyridinyl, thiazolyl, quinolinyl, benzo[1,3]dioxolyl, indolyl, 1,2,3,4-tetrahydroquinolinyl, benzofuranyl, dihydrobenzofuranyl, dihydrobenzoxazolyl, furyl, thienyl, pyrrolo[2,3-b]pyridinyl, pyrimidinyl, benzothiazolyl, benzothiophenyl, benzimidazolyl, indazolyl, benzisoxazolyl, isoquinolinyl or pyrazolyl group;

it being possible for these groups to be optionally substituted with one or more atoms or groups chosen, independently of one another, from halogen, $(C_1-C_{10})$alkyl, oxo, NRaRb, $(C_1-C_{10})$alkoxy, aryl and CONRaRb;

Ra and Rb represent, independently of one another, a hydrogen atom or a $(C_1-C_{10})$alkyl group;

X represents 1 or 2 hydrogen or halogen atoms;

R represents, at position 3, 5, 7 or 8 of the imidazo[1,2-a]pyridine, a hydrogen atom or a $(C_1-C_{10})$alkyl group;

$R_2$ and $R_3$ represent, independently of one another, a hydrogen atom or a $(C_1-C_{10})$alkyl group;

$R_4$ represents a hydrogen atom, or a $(C_1-C_{10})$alkyl group optionally substituted with an Rf group;

Rf represents a $(C_1-C_{10})$alkoxy group;

in the form of a base or of an addition salt with an acid.

Among the compounds of formula (I) which are subjects of the invention, a thirteenth group of compounds is constituted of the compounds for which:

$R_1$ represents an isoxazolyl, pyridinyl, thiazolyl, quinolinyl, benzo[1,3]dioxolyl, indolyl, 1,2,3,4-tetrahydroquinolinyl, benzofuryl, dihydrobenzofuryl, dihydrobenzoxazolyl, furyl, thienyl, pyrrolo[2,3-b]pyridinyl, pyrimidinyl, benzothiazolyl, benzothiophenyl, benzimidazolyl, indazolyl, benzisoxazolyl, isoquinolinyl or pyrazolyl group;

it being possible for these groups to be optionally substituted with one or more atoms or groups chosen, independently of one another, from halogen, methyl, oxo, NRaRb, ethoxy, phenyl, isopentyl, $CONHC(CH_3)_3$ and methoxy;

Ra and Rb represent, independently of one another, a hydrogen atom or a methyl group;

X represents 1 or 2 hydrogen or fluorine atoms;
R represents, at position 3, 5, 7 or 8 of the imidazo[1,2-a]pyridine, a hydrogen atom or a methyl group;
$R_2$ and $R_3$ represent, independently of one another, a hydrogen atom or a methyl group;
$R_4$ represents a hydrogen atom, or a group chosen from methyl, butyl and methoxyethyl groups;
in the form of a base or of an addition salt with an acid.

Among the compounds of formula (I) which are subjects of the invention, a fourteenth group of compounds is constituted of the compounds for which:
$R_1$ represents an isoxazolyl, pyridinyl, thiazolyl, quinolinyl, benzo[1,3]dioxolyl, indolyl, 1,2,3,4-tetrahydroquinolinyl, benzofuranyl, dihydrobenzofuranyl, dihydrobenzoxazolyl, furyl, thienyl, pyrrolo[2,3-b]pyridinyl, pyrimidinyl, benzothiazolyl, benzothiophenyl, benzimidazolyl, indazolyl, benzisoxazolyl, isoquinolinyl or pyrazolyl group;
it being possible for these groups to be optionally substituted with one or more atoms or groups chosen, independently of one another, from halogen, $(C_1-C_{10})$alkyl, oxo, NRaRb, $(C_1-C_{10})$alkoxy, aryl and CONRaRb;
Ra and Rb represent, independently of one another, a hydrogen atom or a $(C_1-C_{10})$alkyl group;
X represents 1 or 2 hydrogen or halogen atoms;
R represents, at position 3, 5, 7 or 8 of the imidazo[1,2-a]pyridine, a hydrogen atom or a $(C_1-C_{10})$alkyl group;
$R_2$ and $R_3$ represent, independently of one another, a hydrogen atom or a $(C_1-C_{10})$alkyl group;
$R_4$ represents a hydrogen atom, or a $(C_1-C_{10})$alkyl group optionally substituted with an Rf group;
Rf represents a $(C_1-C_{10})$alkoxy group;
the group

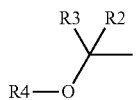

being at position 2, 3 or 4 of the phenyl which bears it;
in the form of a base or of an addition salt with an acid.

Among the compounds of formula (I) which are subjects of the invention, a fifteenth group of compounds is constituted of the compounds for which:
$R_1$ represents an isoxazolyl, pyridinyl, thiazolyl, quinolinyl, benzo[1,3]dioxolyl, indolyl, 1,2,3,4-tetrahydroquinolinyl, benzofuryl, dihydrobenzofuryl, dihydrobenzoxazolyl, furyl, thienyl, pyrrolo[2,3-b]pyridinyl, pyrimidinyl, benzothiazolyl, benzothiophenyl, benzimidazolyl, indazolyl, benzisoxazolyl, isoquinolinyl or pyrazolyl group;
it being possible for these groups to be optionally substituted with one or more atoms or groups chosen, independently of one another, from halogen, methyl, oxo, NRaRb, ethoxy, phenyl, isopentyl, $CONHC(CH_3)_3$ and methoxy;
Ra and Rb represent, independently of one another, a hydrogen atom or a methyl group;
X represents 1 or 2 hydrogen or fluorine atoms;
R represents, at position 3, 5, 7 or 8 of the imidazo[1,2-a]pyridine, a hydrogen atom or a methyl group;
$R_2$ and $R_3$ represent, independently of one another, a hydrogen atom or a methyl group;
$R_4$ represents a hydrogen atom, or a group chosen from methyl, butyl and methoxyethyl groups;
the group

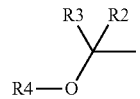

being in position 2, 3 or 4 of the phenyl which bears it;
in the form of a base or of an addition salt with an acid.

Among the compounds of formula (I) which are subjects of the invention, a sixteenth group of compounds is constituted of the compounds for which:
$R_1$ represents an isoxazolyl, pyridinyl, thiazolyl, quinolinyl, benzo[1,3]dioxolyl, indolyl, 1,2,3,4-tetrahydroquinolinyl, benzofuranyl, dihydrobenzofuranyl, dihydrobenzoxazolyl, furyl, thienyl, pyrrolo[2,3-b]pyridinyl group, it being possible for these groups to be optionally substituted with one or more atoms or groups chosen, independently of one another, from halogen, $(C_1-C_{10})$alkyl, oxo, NRaRb and aryl;
X represents a hydrogen,
R represents a hydrogen or a $(C_1-C_{10})$alkyl group;
$R_2$ and $R_3$ represent, independently of one another, a hydrogen atom;
$R_4$ represents a hydrogen atom or a $(C_1-C_{10})$alkyl group, this group being optionally substituted with an Rf group;
Ra and Rb represent, independently of one another, a hydrogen atom or a $(C_1-C_{10})$alkyl group;
Rf represents a $(C_1-C_{10})$alkoxy group;
in the form of a base or of an addition salt with an acid.

Among the compounds of formula (I) which are subjects of the invention, mention may in particular be made of the following compounds:
{3-[2-(5-methylisoxazol-4-yl)imidazo[1,2-a]pyridin-6-yl]phenyl}methanol;
[3-[2-(pyridin-4-yl)imidazo[1,2-a]pyridin-6-yl]phenyl]methanol and the hydrochloride thereof;
6-(3-tertbutoxymethylphenyl)-2-(pyridin-3-yl)imidazo[1,2-a]pyridine hydrochloride (1:2);
[3-[2-(thiazol-4-yl)imidazo[1,2-a]pyridin-6-yl]phenyl]methanol
[3-[2-(quinolin-3-yl)imidazo[1,2-a]pyridin-6-yl]phenyl]methanol and the hydrochloride thereof;
{3-[2-(1,3-benzodioxol-5-yl)imidazo[1,2-a]pyridin-6-yl]phenyl}methanol and the hydrochloride thereof;
[3-]2-(pyridin-3-yl)imidazo[1,2-a]pyridin-6-yl]phenyl]methanol and the hydrochloride thereof;
{3-[2-[(1H-indol-5-yl)imidazo[1,2-a]pyridin-6-yl]phenyl}methanol and the hydrochloride thereof;
6-[6-(3-hydroxymethylphenyl)imidazo[1,2-a]pyridin-2-yl]-3,4-dihydro-1H-quinolin-2-one and the hydrochloride thereof;
2-(5-bromo-2,3-dihydrobenzofuran-7-yl)-6-(3-tert-butoxymethylphenyl)imidazo[1,2-a]pyridine;
6-[6-(3-hydroxymethylphenyl)imidazo[1,2-a]pyridin-2-yl]-3H-benzoxazol-2-one and the hydrochloride thereof;
[2-(2-furan-3-ylimidazo[1,2-a]pyridin-6-yl)phenyl]methanol hydrochloride (1:1);
{3-[2-(5-bromo-2,3-dihydrobenzofuran-7-yl)imidazo[1,2-a]pyridin-6-yl]phenyl}methanol;
{3-[2-(5-chlorothien-2-yl)imidazo[1,2-a]pyridin-6-yl]phenyl}methanol and the hydrochloride thereof;

{3-[2-(6-dimethylaminopyridin-3-yl)imidazo[1,2-a]pyridin-6-yl]phenyl}methanol and the hydrochloride thereof;
{3-[2-(1H-indol-4-yl)imidazo[1,2-a]pyridin-6-yl]phenyl}methanol and the hydrochloride thereof;
{3-[2-(6-aminopyridin-3-yl)imidazo[1,2-a]pyridin-6-yl]phenyl}methanol and the hydrochloride thereof;
{3-[2-(1H-indol-3-yl)imidazo[1,2-a]pyridin-6-yl]phenyl}methanol and the hydrochloride thereof;
{3-[2-(2-aminopyridin-3-yl)imidazo[1,2-a]pyridin-6-yl]phenyl}methanol and the hydrochloride thereof;
{3-[2-(1H-pyrrolo[2,3-b]pyridin-5-yl)imidazo[1,2-a]pyridin-6-yl]phenyl}methanol and the hydrochloride thereof;
{3-[2-(3-phenylisoxazol-5-yl)imidazo[1,2-a]pyridin-6-yl]phenyl}methanol;
[3-[2-(benzofuran-2-yl)imidazo[1,2-a]pyridin-6-yl]phenyl]methanol;
[3-[2-(benzofuran-3-yl)imidazo[1,2-a]pyridin-6-yl]phenyl]methanol;
[4-[2-(benzofuran-3-yl)imidazo[1,2-a]pyridin-6-yl]phenyl]methanol;
[3-[2-(pyridin-2-yl)imidazo[1,2-a]pyridin-6-yl]phenyl]methanol;
[4-[2-(pyridin-2-yl)imidazo[1,2-a]pyridin-6-yl]phenyl]methanol;
[3-[2-(thien-2-yl)imidazo[1,2-a]pyridin-6-yl]phenyl]methanol;
2-(benzofuran-2-yl)-6-[3-(2-methoxyethoxymethyl)phenyl]imidazo[1,2-a]pyridine;
6-[3-(2-methoxyethoxymethyl)phenyl]-2-(thien-2-yl)imidazo[1,2-a]pyridine and the oxalate thereof;
[3-(2-thien-3-ylimidazo[1,2-a]pyridin-6-yl)phenyl]methanol;
[3-(3-methyl-2-thien-2-ylimidazo[1,2-a]pyridin-6-yl)phenyl]methanol hydrochloride (1:1);
{3-[2-(1H-indol-3-yl)-3-methylimidazo[1,2-a]pyridin-6-yl]phenyl}methanol and the hydrochloride thereof;
{3-[2-(1H-indol-6-yl)imidazo[1,2-a]pyridin-6-yl]phenyl}methanol and the hydrochloride thereof;
{3-[2-(2-ethoxypyrimidin-5-yl)imidazo[1,2-a]pyridin-6-yl]phenyl}methanol and the hydrochloride thereof;
[2-(2-quinolin-3-ylimidazo[1,2-a]pyridin-6-yl)phenyl]methanol and the hydrochloride thereof;
{3-[2-(2-chloropyridin-4-yl)imidazo[1,2-a]pyridin-6-yl]phenyl}methanol and the hydrochloride thereof;
[3-(2-benzothiazol-2-ylimidazo[1,2-a]pyridin-6-yl)phenyl]methanol and the hydrochloride thereof;
[3-(2-benzo[b]thiophen-2-ylimidazo[1,2-a]pyridin-6-yl)phenyl]methanol and the hydrochloride thereof;
[3-(2-benzo[b]thiophen-5-ylimidazo[1,2-a]pyridin-6-yl)phenyl]methanol and the hydrochloride thereof;
3-(2-benzo[b]thiophen-3-ylimidazo[1,2-a]pyridin-6-yl)phenyl]methanol and the hydrochloride thereof;
{2-[2-(1H-indol-6-yl)imidazo[1,2-a]pyridin-6-yl]phenyl}methanol and the hydrochloride thereof;
{3-[2-(2,3-dihydrobenzofuran-5-yl)imidazo[1,2-a]pyridin-6-yl]phenyl}methanol and the hydrochloride thereof;
{2-[2-(1H-indol-5-yl)imidazo[1,2-a]pyridin-6-yl]phenyl}methanol and the hydrochloride thereof;
[3-(2-benzofuran-5-ylimidazo[1,2-a]pyridin-6-yl)phenyl]methanol;
{3-[2-(3-chlorothien-2-yl)imidazo[1,2-a]pyridin-6-yl]phenyl}methanol;
{2-fluoro-6-[2-(5-methylisoxazol-3-yl)imidazo[1,2-a]pyridin-6-yl]phenyl}methanol;
2-{3-[2-(1H-indol-6-yl)imidazo[1,2-a]pyridin-6-yl]phenyl}propan-2-ol;
2-[3-(3-methyl-2-thien-2-ylimidazo[1,2-a]pyridin-6-yl)phenyl]propan-2-ol;
2-[3-(2-thien-3-ylimidazo[1,2-a]pyridin-6-yl)phenyl]propan-2-ol;
2-[3-(2-pyridin-2-ylimidazo[1,2-a]pyridin-6-yl)phenyl]propan-2-ol;
2-{3-[2-(5-chlorothien-2-yl)imidazo[1,2-a]pyridin-6-yl]phenyl}propan-2-ol;
2-[3-(2-benzofuran-2-ylimidazo[1,2-a]pyridin-6-yl)phenyl]propan-2-ol;
2-[3-(2-thien-2-ylimidazo[1,2-a]pyridin-6-yl)phenyl]propan-2-ol;
2-[3-(2-benzofuran-3-ylimidazo[1,2-a]pyridin-6-yl)phenyl]propan-2-ol;
2-[3-(2-benzothiazol-2-ylimidazo[1,2-a]pyridin-6-yl)phenyl]propan-2-ol;
2-[3-(2-benzo[b]thienyl-2-ylimidazo[1,2-a]pyridin-6-yl)phenyl]propan-2-ol;
2-{3-[2-(1-methyl-1H-benzimidazol-2-yl)imidazo[1,2-a]pyridin-6-yl]phenyl}propan-2-ol;
2-{3-[2-(2,3-dihydrobenzofuran-5-yl)imidazo[1,2-a]pyridin-6-yl]phenyl}propan-2-ol;
2-[3-(2-furan-2-ylimidazo[1,2-a]pyridin-6-yl)phenyl]propan-2-ol;
2-[3-(2-benzofuran-5-ylimidazo[1,2-a]pyridin-6-yl)phenyl]propan-2-ol;
2-[3-(2-benzo[b]thienyl-5-ylimidazo[1,2-a]pyridin-6-yl)phenyl]propan-2-ol;
2-[3-(2-thiazol-2-ylimidazo[1,2-a]pyridin-6-yl)phenyl]propan-2-ol;
{2-fluoro-6-[2-(1H-indazol-3-yl)imidazo[1,2-a]pyridin-6-yl]phenyl}methanol and the hydrochloride thereof;
2-{3-[2-(1H-indazol-3-yl)imidazo[1,2-a]pyridin-6-yl]phenyl}propan-2-ol and the hydrochloride thereof;
{2,6-difluoro-3-[2-(1H-indazol-3-yl)imidazo[1,2-a]pyridin-6-yl]phenyl}methanol and the hydrochloride thereof;
[2-fluoro-6-(2-thien-3-ylimidazo[1,2-a]pyridin-6-yl)phenyl]methanol;
[2-fluoro-6-(2-pyridin-2-ylimidazo[1,2-a]pyridin-6-yl)phenyl]methanol;
[2-fluoro-6-(2-thien-2-ylimidazo[1,2-a]pyridin-6-yl)phenyl]methanol;
[2-(2-benzothiazol-2-ylimidazo[1,2-a]pyridin-6-yl)-6-fluorophenyl]methanol;
[2-(2-benzo[b]thiophen-2-ylimidazo[1,2-a]pyridin-6-yl)-6-fluorophenyl]methanol;
{2-[2-(2,3-dihydrobenzofuran-5-yl)imidazo[1,2-a]pyridin-6-yl]-6-fluorophenyl}methanol;
[2-(2-benzofuran-5-ylimidazo[1,2-a]pyridin-6-yl)-6-fluorophenyl]methanol;
[2-(2-benzo[b]thienyl-5-ylimidazo[1,2-a]pyridin-6-yl)-6-fluorophenyl]methanol;
[2-fluoro-6-(2-thiazol-2-ylimidazo[1,2-a]pyridin-6-yl)phenyl]methanol;
[2,6-difluoro-3-(3-methyl-2-thien-2-ylimidazo[1,2-a]pyridin-6-yl)phenyl]methanol;
[2,6-difluoro-3-(2-thien-3-ylimidazo[1,2-a]pyridin-6-yl)phenyl]methanol;
[2,6-difluoro-3-(2-pyridin-2-ylimidazo[1,2-a]pyridin-6-yl)phenyl]methanol;

{3-[2-(5-chlorothien-2-yl)imidazo[1,2-a]pyridin-6-yl]-2,6-difluorophenyl}methanol;

[3-(2-benzofuran-2-ylimidazo[1,2-a]pyridin-6-yl)-2,6-difluorophenyl]methanol;

[2,6-difluoro-3-(2-thien-2-ylimidazo[1,2-a]pyridin-6-yl)phenyl]methanol;

[3-(2-benzofuran-3-ylimidazo[1,2-a]pyridin-6-yl)-2,6-difluorophenyl]methanol;

[3-(2-benzothiazol-2-ylimidazo[1,2-a]pyridin-6-yl)-2,6-difluorophenyl]methanol;

[2,6-difluoro-3-(2-thiazol-2-ylimidazo[1,2-a]pyridin-6-yl)phenyl]methanol;

6-(3-methoxymethylphenyl)-2-(1-methyl-1H-indol-6-yl)imidazo[1,2-a]pyridine and the hydrochloride thereof;

2-(1H-indol-6-yl)-6-(3-methoxymethylphenyl)imidazo[1,2-a]pyridine and the hydrochloride thereof;

2-{3-[2-(5-methylisoxazol-3-yl)imidazo[1,2-a]pyridin-6-yl]phenyl}propan-2-ol;

[2-fluoro-6-(3-methyl-2-thienyl-2-ylimidazo[1,2-a]pyridin-6-yl)phenyl]methanol;

{2-[2-(5-chlorothiophen-2-yl)imidazo[1,2-a]pyridin-6-yl]-6-fluorophenyl}methanol;

[2-(2-benzofuran-2-ylimidazo[1,2-a]pyridin-6-yl)-6-fluorophenyl]methanol;

[2-(2-benzofuran-3-ylimidazo[1,2-a]pyridin-6-yl)-6-fluorophenyl]methanol;

{2-fluoro-6-[2-(1-methyl-1H-benzimidazol-2-yl)imidazo[1,2-a]pyridin-6-yl]phenyl}methanol;

[2-fluoro-6-(2-furan-2-ylimidazo[1,2-a]pyridin-6-yl)phenyl]methanol;

[3-(2-benzo[b]thienyl-2-ylimidazo[1,2-a]pyridin-6-yl)-2,6-difluorophenyl]methanol;

{2,6-difluoro-3-[2-(1-methyl-1H-benzimidazol-2-yl)imidazo[1,2-a]pyridin-6-yl]phenyl}methanol;

{3-[2-(2,3-dihydrobenzofuran-5-yl)imidazo[1,2-a]pyridin-6-yl]-2,6-difluorophenyl}methanol;

[2,6-difluoro-3-(2-furan-2-ylimidazo[1,2-a]pyridin-6-yl)phenyl]methanol;

[3-(2-benzofuran-5-ylimidazo[1,2-a]pyridin-6-yl)-2,6-difluorophenyl]methanol;

[3-(2-benzo[b]thienyl-5-ylimidazo[1,2-a]pyridin-6-yl)-2,6-difluorophenyl]methanol;

2-(1H-indol-6-yl)-6-[3-[2-(methoxyethyl)oxymethyl]phenyl]imidazo[1,2-a]pyridine;

2-[3-(2-benzo[d] isoxazol-3-ylimidazo[1,2-a]pyridin-6-yl)phenyl]propan-2-ol;

[2-(2-benzo[d] isoxazol-3-ylimidazo[1,2-a]pyridin-6-yl)-6-fluorophenyl]methanol;

2-{3-[2-(1H-indol-5-yl)imidazo[1,2-a]pyridin-6-yl]phenyl}propan-2-ol;

2-{3-[2-(1H-indol-4-yl)imidazo[1,2-a]pyridin-6-yl]phenyl}propan-2-ol;

2-{3-[2-(2-methoxypyridin-3-yl)imidazo[1,2-a]pyridin-6-yl]phenyl}propan-2-ol;

2-{3-[2-(4-methylthien-3-yl)imidazo[1,2-a]pyridin-6-yl]phenyl}propan-2-ol;

2-{3-[2-(1-methyl-1H-indol-5-yl)imidazo[1,2-a]pyridin-6-yl]phenyl}propan-2-ol;

2-[3-(2-quinolin-5-ylimidazo[1,2-a]pyridin-6-yl)phenyl]propan-2-ol;

2-[3-(2-isoquinolin-5-ylimidazo[1,2-a]pyridin-6-yl)phenyl]propan-2-ol;

2-{3-[2-(2,6-difluoropyridin-4-yl)imidazo[1,2-a]pyridin-6-yl]phenyl}propan-2-ol;

2-(3-{2-[1-(3-methylbutyl)-1H-pyrazol-4-yl]imidazo[1,2-a]pyridin-6-yl}phenyl)propan-2-ol;

2-[3-(2-quinolin-3-ylimidazo[1,2-a]pyridin-6-yl)phenyl]propan-2-ol;

{2-fluoro-6-[2-(1H-indol-5-yl)imidazo[1,2-a]pyridin-6-yl]phenyl}methanol;

{2-fluoro-6-[2-(6-methoxypyridin-3-yl)imidazo[1,2-a]pyridin-6-yl]phenyl}methanol {2-fluoro-6-[2-(3-fluoropyridin-4-yl)imidazo[1,2-a]pyridin-6-yl]phenyl}methanol;

{2-fluoro-6-[2-(4-methylthien-2-yl)imidazo[1,2-a]pyridin-6-yl]phenyl}methanol;

[2-fluoro-6-(2-pyrimidin-5-ylimidazo[1,2-a]pyridin-6-yl)phenyl]methanol;

{2-fluoro-6-[2-(1H-indol-4-yl)imidazo[1,2-a]pyridin-6-yl]phenyl}methanol;

{2-fluoro-6-[2-(1H-indol-6-yl)imidazo[1,2-a]pyridin-6-yl]phenyl}methanol;

{2-fluoro-6-[2-(2-methoxypyridin-3-yl)imidazo[1,2-a]pyridin-6-yl]phenyl}methanol;

{2-fluoro-6-[2-(4-methylthien-3-yl)imidazo[1,2-a]pyridin-6-yl]phenyl}methanol;

{2-fluoro-6-[2-(1-methyl-1H-indol-5-yl)imidazo[1,2-a]pyridin-6-yl]phenyl}methanol;

[2-fluoro-6-(2-quinolin-5-ylimidazo[1,2-a]pyridin-6-yl)phenyl]methanol;

[2-fluoro-6-(2-isoquinolin-5-ylimidazo[1,2-a]pyridin-6-yl)phenyl]methanol;

{2-[2-(2,6-difluoropyridin-4-yl)imidazo[1,2-a]pyridin-6-yl]-6-fluorophenyl}methanol;

(2-fluoro-6-{2-[1-(3-methylbutyl)-1H-pyrazol-4-yl]imidazo[1,2-a]pyridin-6-yl}phenyl)methanol;

{2,6-difluoro-3-[2-(1H-indol-5-yl)imidazo[1,2-a]pyridin-6-yl]phenyl}methanol;

{2,6-difluoro-3-[2-(6-methoxypyridin-3-yl)imidazo[1,2-a]pyridin-6-yl]phenyl}methanol;

{2,6-difluoro-3-[2-(4-methylthien-2-yl)imidazo[1,2-a]pyridin-6-yl]phenyl}methanol;

{2,6-difluoro-3-[2-(1H-indol-6-yl)imidazo[1,2-a]pyridin-6-yl]phenyl}methanol;

{2,6-difluoro-3-[2-(2-methoxypyridin-3-yl)imidazo[1,2-a]pyridin-6-yl]phenyl}methanol;

{2,6-difluoro-3-[2-(4-methylthien-3-yl)imidazo[1,2-a]pyridin-6-yl]phenyl}methanol;

{2,6-difluoro-3-[2-(1-methyl-1H-indol-5-yl)imidazo[1,2-a]pyridin-6-yl]phenyl}methanol;

[2,6-difluoro-3-(2-quinolin-5-ylimidazo[1,2-a]pyridin-6-yl)phenyl]methanol;

[2,6-difluoro-3-(2-isoquinolin-5-ylimidazo[1,2-a]pyridin-6-yl)phenyl]methanol;

{3-[2-(2,6-difluoropyridin-4-yl)imidazo[1,2-a]pyridin-6-yl]-2,6-difluorophenyl}methanol;

(2,6-difluoro-3-{2-[1-(3-methylbutyl)-1H-pyrazol-4-yl]imidazo[1,2-a]pyridin-6-yl}phenyl)methanol;

N-tert-butyl-5-[6-(2,4-difluoro-3-hydroxymethylphenyl)imidazo[1,2-a]pyridin-2-yl]nicotinamide.

In accordance with the invention, the compounds of general formula (I) can be prepared according to the process described in scheme 1.

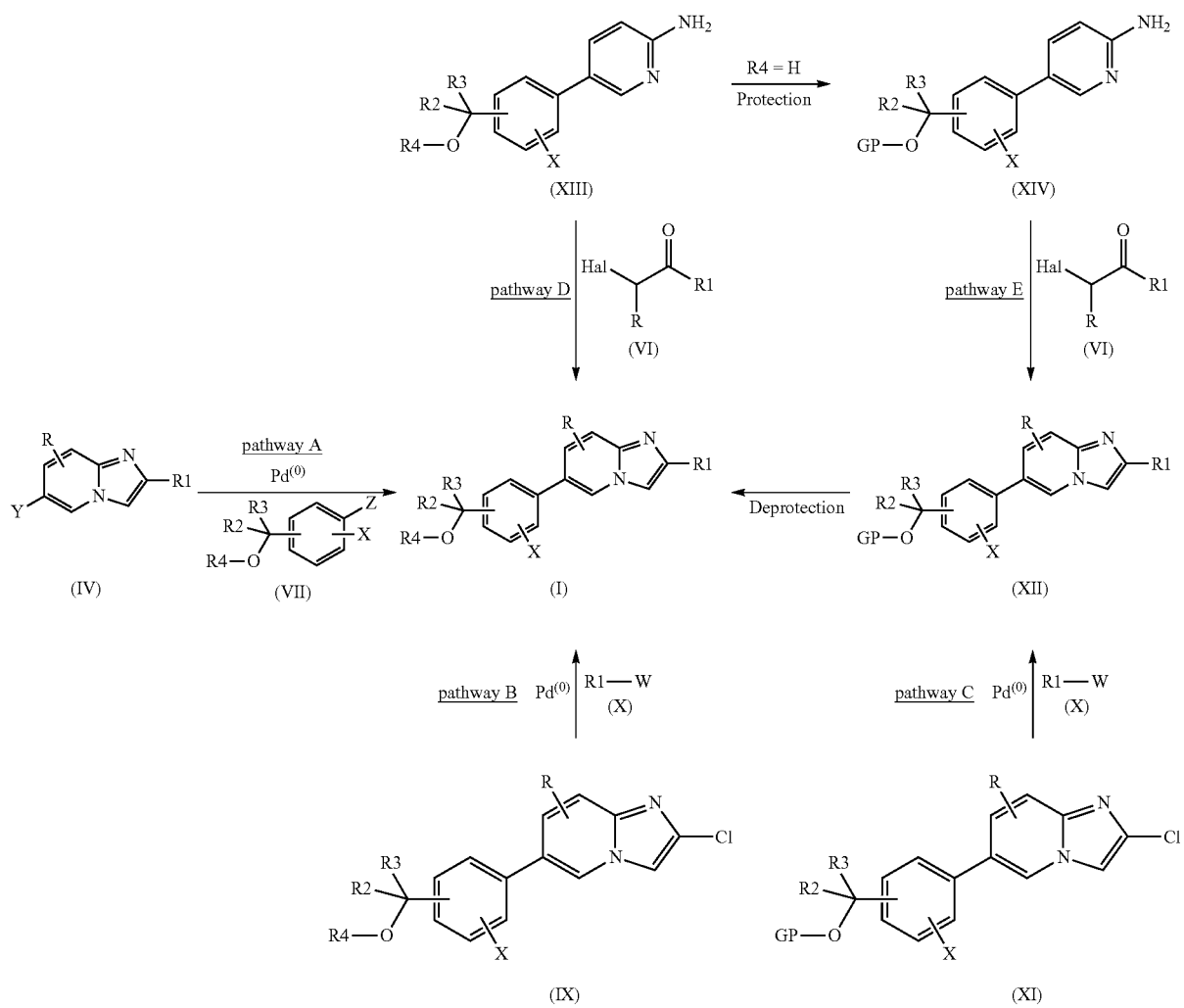

Scheme 1

The compounds of the invention can be prepared according to scheme 1 (pathway A) by means of a coupling reaction, catalysed by a metal such as palladium, between an imidazopyridine of general formula (IV), in which R and R1 are defined as above and Y represents a halogen atom or a boron derivative, and a derivative of general formula (VII), in which R2, R3, R4 and X are defined as above and Z represents a boron or tin derivative if Y represents a halogen atom, or a halogen if Y represents a boron derivative, so as to obtain the compounds of general formula (I), for example according to the method described by A. Gueiffier in *Helv. Chim. Acta* 2001, 84, 3610-3615.

Alternatively, the compounds of the invention can be prepared according to scheme 1 (pathway B) by means of a coupling reaction, catalysed by a metal such as palladium, between a 2-chloroimidazopyridine of general formula (IX), in which R, R2, R3, R4 and X are defined as above, and a derivative of general formula (X), in which R1 is defined as above and W represents a boron or tin derivative, so as to obtain the compounds of general formula (I), for example according to the method described by S. Buchwald in *J.A.C.S.* 2005, 127, 4685.

According to scheme 1 (pathway C), the derivatives of general formula (XI), in which R, R2, R3 and X are defined as above and PG represents a hydroxyl-function-protecting group, as described, for example, by T. Greene dans "*Protective Groups in Organic Synthesis*" (*Wiley Interscience*), can be subjected to a coupling reaction, catalysed by a metal such as palladium, with a derivative of general formula (X), in which R1 is defined as above and W represents a boron or tin derivative, so as to obtain the compounds of general formula (XII), for example according to the method described by S. Buchwald in *J.A.C.S.* 2005, 127, 4685. Finally, the compounds of general formula (XII) can be subjected to a deprotection reaction, as described, for example, by T. Greene in "*Protective Groups in Organic Synthesis*" (*Wiley Interscience*), or by any other method known to those skilled in the art, so as to obtain the compounds of general formula (I).

Alternatively, the compounds of the invention can be prepared according to scheme 1 (pathway D) by condensation between an aminopyridine of general formula (XIII), in which R2, R3, R4 and X are defined as above, R4 not being a hydrogen atom, and a haloketone of general formula (VI), in which R and R1 are defined as above, so as to obtain the compounds of general formula (I), for which R is at position 3 with respect to the imidazopyridine nucleus.

When R4 represents a hydrogen atom, the compounds of general formula (XIII) can be converted according to scheme 1 (pathway E) into derivatives of general formula (XIV), in which R2, R3 and X are defined as above and PG represents a hydroxyl-function-protecting group, as described, for example, by T. Greene in "*Protective Groups in Organic Synthesis*" (*Wiley Interscience*), or by any method known to those skilled in the art. The compounds of general formula (XIV) can be condensed with a haloketone of general formula (VI), in which R and R1 are defined as above, so as to obtain the compounds of general formula (XII), for which R is at position 3 with respect to the imidazopyridine nucleus. Finally, the compounds of general formula (XII) can be subjected to a deprotection reaction, as described, for example, by T. Greene in "*Protective Groups in Organic Synthesis*" (*Wiley Interscience*), or by any other method known to those skilled in the art, so as to obtain the compounds of general formula (I).

In accordance with the invention, the intermediates of the compounds of general formula (I) can be prepared according to the processes described in scheme 2.

defined as above, so as to obtain the compounds of general formula (IV), for which R is at position 3 of the imidazopyridine nucleus.

According to scheme 2 (pathway c), the compounds of general formula (XIIIa), (XIIIb) or (XIV) can be obtained by means of a coupling reaction, catalysed by a metal such as palladium, between an aminopyridine of general formula (Va) or (Vb), protected by a protective group R', in which Y represents a halogen atom or a boron derivative, and a derivative of general formula (VII), in which R2, R3 and X are defined as above, R6 represents R4 (compounds XIIIa and XIIIb) or a hydroxyl-function-protecting group PG (compounds XIV) and Z represents a boron or tin derivative if Y represents a halogen, or a halogen if Y represents a boron derivative.

According to scheme 2 (pathway d), the compounds of general formula (VIII) can be obtained from the compounds of general formula (II), for example according to the method described by C. Townsend in *Syn. Commun.* 1997, 27, 1763-

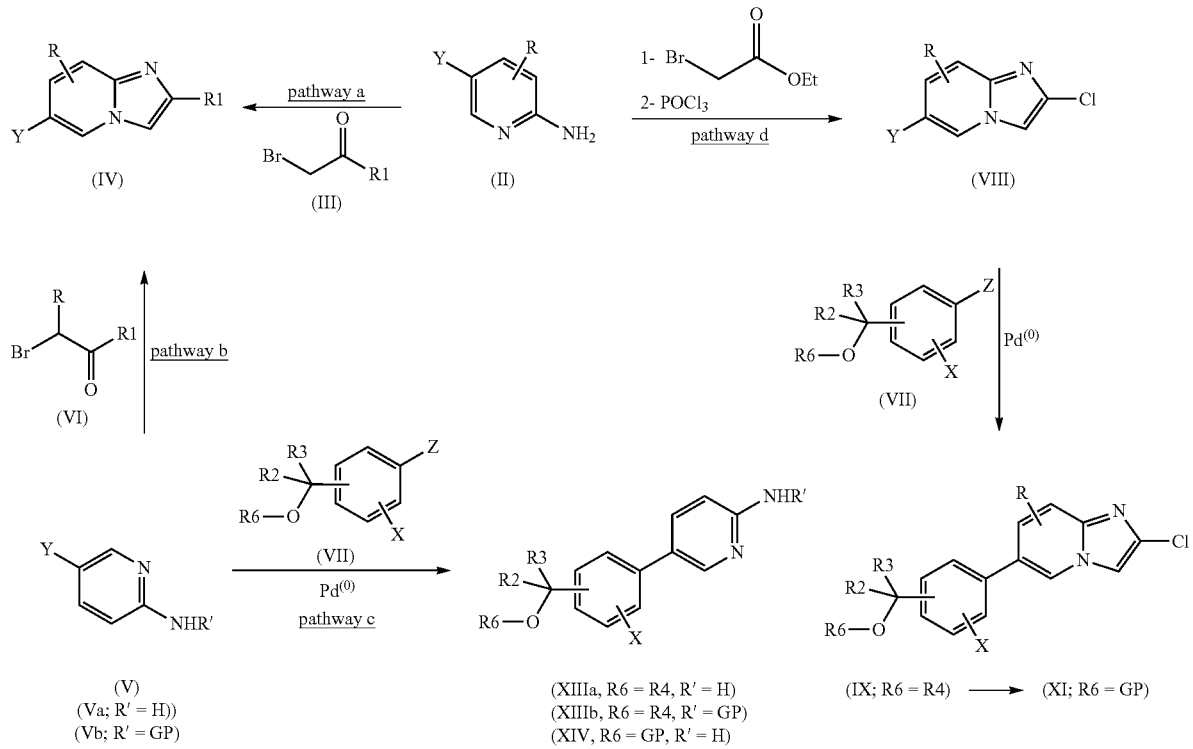

Scheme 2

According to scheme 2 (pathway a), the compounds of general formula (IV) can be obtained by condensation between an aminopyridine of general formula (II), in which R is defined as above and Y represents a halogen atom or a boron derivative, and a haloketone of general formula (III), in which R1 is defined as above, for example according to the methods described by L. Cai in *J. Med. Chem.* 2007, 50, 4746, so as to obtain the compounds of general formula (IV), for which R is at position 5, 7 or 8 of the imidazopyridine nucleus.

Alternatively, according to scheme 2 (pathway b), the compounds of general formula (IV) can be obtained by condensation between an aminopyridine of general formula (V), in which Y represents a halogen atom or a boron derivative, and a haloketone of general formula (VI), in which R and R1 are 1765. The compounds of general formula (IX) or (XI), in which R, R2, R3 and X are defined as above and R6 represents an R4 group (compounds IX) or a protective group PG (compounds XI), can be obtained by means of a coupling reaction, catalysed by a metal such as palladium, between an imidazopyridine of general formula (VIII), in which R is defined as above and Y represents a halogen atom or a boron derivative, and a derivative of general formula (VII), in which R2, R3 and X are defined as above, R6 represents an R4 group or a protective group PG and Z represents a boron or tin derivative if Y represents a halogen atom, or a halogen if Y represents a boron derivative, for example according to the method described by A. Gueiffier in *Helv. Chim. Acta* 2001, 84, 3610-3615.

In general, the above intermediates can be subjected, if desired and if necessary, to any protection/deprotection reactions known to those skilled in the art before and/or after any reactions described in the schemes above.

The products of formula (I) can be subjected, if necessary and if desired, to any reactions known to those skilled in the art, in any order, so as to be converted into other products of formula (I).

By way of examples of reactions, mention may be made of: reactions for esterification or for amidation of an acid function, carbamoylation reactions, ester function hydrolysis reactions, reactions for converting a hydroxyl function to an alkoxy function, coupling reactions catalysed by a transition metal, reactions for protecting reactive functions, reactions for removing the protective groups that the protected reactive functions may be bearing, salification reactions with an inorganic or organic acid or with a base so as to obtain the corresponding salt, reactions for resolving racemic forms into enantiomers, said products of formula (I) thus obtained being, where appropriate, in all the possible racemic, enantiomeric and diastereoisomeric isomer forms.

In schemes 1 and 2, the starting compounds and the reactants, when the method for preparing them is not described, are commercially available or described in the literature, or else can be prepared according to methods which are described therein or which are known to those skilled in the art.

According to another of its aspects, a subject of the invention is also the compounds of formulae (VIII-1), (IX-1), (IX-2), (XI-1), (XI-2), (XI-3), (XI-4), (XIII-1), (XIII-2), (XIV-1), (XIV-2) and (XIV-3). These compounds are useful as synthesis intermediates of the compounds of formula (I).

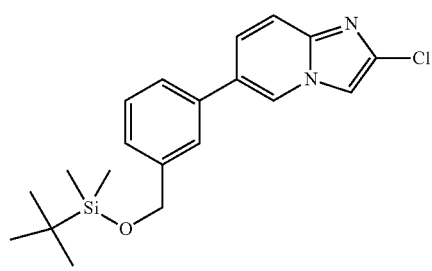
(XI-1)

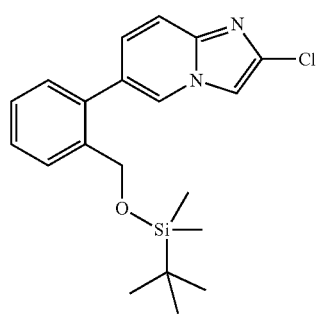
(XI-2)

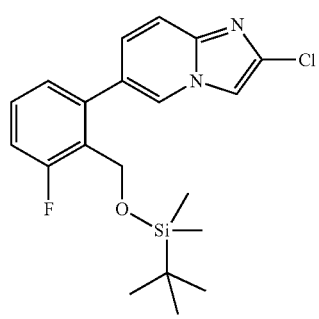
(XI-3)

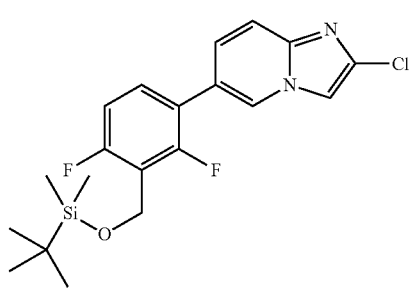
(XI-4)

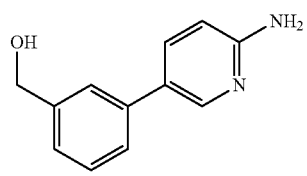
(XIII-1)

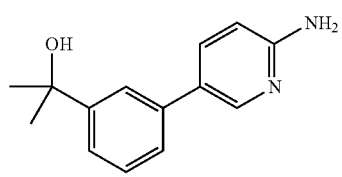
(XIII-2)

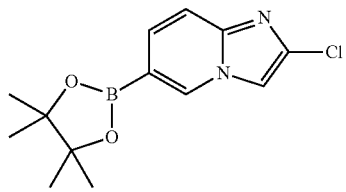
(VIII-1)

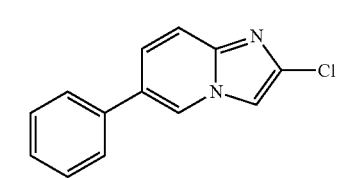
(IX-1)

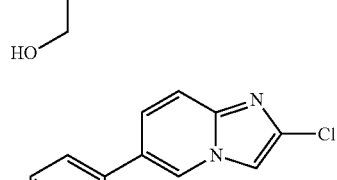
(IX-2)

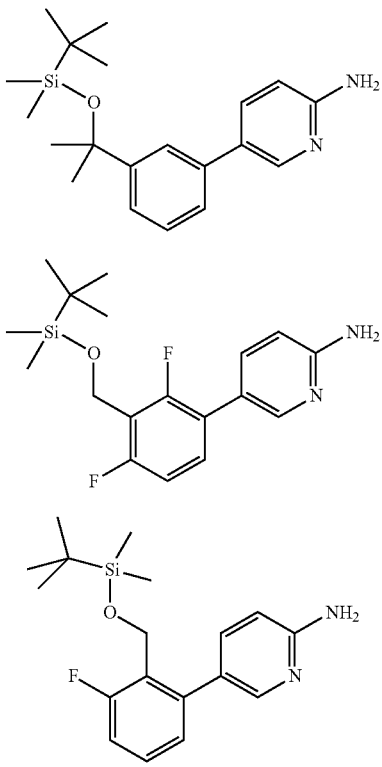

(XIV-1)

(XIV-2)

(XIV-3)

The compound of formula (VIII-1) can be prepared, for example, according to the process described in Example No. 3. In a first stage, a condensation can be carried out between an aminopyridine substituted with a boron derivative, such as, for example, 5-(4,4,5,5-tetramethyl-1,3,2-dioxaborolan-2-yl)pyridin-2-ylamine and ethyl 2-bromoacetate. In a second stage, the compound is subjected to a cyclization and chlorination reaction in the presence of a chlorinating agent such as phosphorus oxychloride, which gives the compound (VIII-1).

The compound of formula (IX-1) can be prepared by means of a coupling reaction, catalysed by a metal, such as palladium, between 6-bromo-2-chloroimidazo[1,2-a]pyridine and 3-(hydroxymethyl)phenylboronic acid, as described in Example No. 2.

The compound of formula (IX-2) can be prepared by means of a coupling reaction, catalysed by a metal, such as palladium, between the compound of formula (VIII-1) and 2-(3-bromophenyl)propan-2-ol, as described in Example No. 7

The compound of formula (XI-1) can be prepared through the action of tert-butylchlorodimethylsilane on the compound of formula (IX-1), in the presence of a base such as imidazole and in a solvent such as tetrahydrofuran, as described in Example No. 4.

The compound of formula (XI-2) can be prepared by means of a coupling reaction, catalysed by a metal, such as palladium, between (2-bromobenzyloxy)-tert-butyldimethylsilane and the compound of formula (VIII-1), as described in Example No. 3.

The compound of formula (XI-3) can be prepared by means of a coupling reaction, catalysed by a metal, such as palladium, between (2-bromo-6-fluorobenzyloxy)-tert-butyldimethylsilane and the compound of formula (VIII-1), as described in Example No. 13.

The compound of formula (XI-4) can be prepared by means of a coupling reaction, catalysed by a metal, such as palladium, between (3-bromo-2,6-difluorobenzyloxy)-tert-butyldimethylsilane and the compound of formula (VIII-1), as described in Example No. 14.

The compound of formula (XIII-1) can be prepared by means of a coupling reaction, catalysed by a metal, such as palladium, between 5-bromo-2-aminopyridine and a boronic acid derivative, for example 3-(hydroxymethyl)phenylboronic acid, as described in Example No. 6.

The compound of formula (XIII-2) can be prepared by means of a coupling reaction, catalysed by a metal, such as palladium, between 5-(4,4,5,5-tetramethyl-1,3,2-dioxaborolan-2-yl)pyridin-2-ylamine and 2-(3-bromophenyl)propan-2-ol, as described in Example No. 8

The compound of formula (XIV-1) can be prepared through the action of (tert-butylchlorodimethyl)silane on the compound of formula (XIII-1) in a solvent, for example tetrahydrofuran, in the presence of a base such as imidazole, as described in Example No. 6.

The compound of formula (XIV-2) can be prepared by means of a coupling reaction, catalysed by a metal, such as palladium, between 5-(4,4,5,5-tetramethyl-1,3,2-dioxaborolan-2-yl)pyridin-2-ylamine and 3-(tent-butyldimethylsilyloxymethyl)-2,4-difluorobromobenzene, as described in Example No. 10

The compound of formula (XIV-3) can be prepared by means of a coupling reaction, catalysed by a metal, such as palladium, between 5-(4,4,5,5-tetramethyl-1,3,2-dioxaborolan-2-yl)pyridin-2-ylamine and 2-(tent-butyldimethylsilyloxymethyl)-3-fluorobromobenzene, as described in Example No. 9

The compounds of formulae (VIII-1), (IX-1), (XI-1), (XI-2), (XIII-1) and (XIV-1) were prepared in the form of a powder or of an oil, in the form of a base or of a salt. Table 1 gives some physicochemical data of these intermediates.

TABLE 1

| No. | $^1$H NMR (DMSO-d6, δ ppm); M + H; Mp |
|---|---|
| (VIII-1) | 1.35 (m, 12H); 7.4 (d, 1H); 7.5 (d, 1H); 8.1 (s, 1H); 8.85 (s, 1H); M + H = 279; Mp = 115-120° C. |
| (IX-1) | 4.6 (d, 2H); 5.3 (t, 1H); from 7.35 to 7.75 (m, 6H); 8.1 (s, 1H); 8.85 (s, 1H); M + H = 259. |
| (IX-2) | 1.5 (s, 6H); 5.1 (s, 1H); 7.45 (m, 1H); 7.55 (m, 2H); from 7.6 to 7.7 (m, 2H); 7.8 (s, 1H); 8.05 (s, 1H); 8.85 (s, 1H). |
| (XI-1) | 0.10 (s, 6H); 0.92 (s, 9H); 4.79 (s, 2H); 7.37 (d, 1H); from 7.55 to 7.67 (m, 5H); 8.05 (s, 1H); 8.84 (t, 1H); M + H = 373; Mp = 120-123° C. |
| (XI-2) | (CDCl$_3$): 0 (s, 6H); 0.85 (s, 9H); 4.5 (s, 2H); from 7.15 to 7.55 (m, 7H); 8.15 (s, 1H); M + H = 373. |
| (XI-3) | (CDCl$_3$): 0 (s, 6H); 0.85 (s, 9H); 4.5 (s, 2H); from 7.05 to 7.1 (m, 2H); from 7.25 to 7.3 (m, 2H); 7.4 (s, 1H); 7.45 (s, 1H); 8.3 (s, 1H). M + H = 391. |

TABLE 1-continued

| No. | $^1$H NMR (DMSO-d6, δ ppm); M + H; Mp |
|---|---|
| (XI-4) | 0.0 (s, 6H); 0.8 (s, 9H); 4.7 (s, 2H); 7.15 (t, 1H); 7.4 (d, 1H); from 7.5 to 7.6 (m, 2H); 8.0 (s, 1H); 8.65 (s, 1H). M + H = 409. |
| (XIII-1) | 4.55 (d, 2H); 5.2 (t, 1H); 6.05 (s, 2H); 6.55 (d, 1H); 7.2 (d, 1H); from 7.3 to 7.55 (m, 3H); 7.7 (d, 1H); 8.25 (s, 1H); M + H = 201 |
| (XIII-2) | 1.45 (s, 6H); 5.0 (s, 1H); 6.0 (s, 2H); 6.55 (d, 1H); from 7.3 to 7.4 (m, 3H); 7.65 (s, 1H); 7.7 (d, 1H); 8.25 (s, 1H). M + H = 229 |
| (XIV-1) | 0.09 (s, 6H); 0.91 (s, 9H); 4.75 (s, 2H); 6.02 (m, 2H); 6.52 (dd, 1H); 7.21 (d, 1H); 7.36 (t, 1H); 7.43 (d, 1H); 7.47 (s, 1H); 7.66 (dd, 1H); 8.21 (d, 1H). M + H = 315; Mp = 82-84° C. |
| (XIV-2) | 0 (s, 6H); 0.8 (s, 9H); 4.7 (s, 2H); 6.05 (s, 2H); 6.45 (d, 1H); 7.05 (t, 1H); from 7.35 to 7.45 (m, 2H); 8.0 (s, 1H). M + H = 351 |
| (XIV-3) | 0 (s, 6H); 0.85 (s, 9H); 4.5 (s, 2H); 6.05 (s, 2H); 6.45 (d, 1H); from 7.05 to 7.15 (m, 2H); from 7.3 to 7.4 (m, 1H); from 7.45 to 7.5 (m, 1H); 8.0 (d, 1H). M + H = 333 |

The following examples describe the preparation of certain compounds in accordance with the invention. These examples are not limiting and merely illustrate the invention. The numbers of the compounds exemplified refer back to those given in the table hereinafter, which illustrates the chemical structures and the physical properties of some compounds according to the invention.

The nomenclature of the compounds was established on the basis of the Autonom software.

EXAMPLE 1

6-(3-tert-Butoxymethylphenyl)-2-(pyridin-3-yl)imidazo[1,2-a]pyridine hydrochloride (1:2) (compound 3 of the table)

1.1 N-[5-(3-tert-Butoxymethylphenyl)pyridin-2-yl]acetamide

Under an argon stream, 1.0 g of N-(5-bromopyridin-2-yl)acetamide, 967 mg of 3-(tert-butoxymethyl)phenylboronic acid and 269 mg of tetrakis(triphenylphosphine)-palladium are placed in a round-bottomed flask containing 30 ml of dimethoxyethane and 15 ml of a 2M solution of sodium carbonate degassed beforehand. The mixture is heated at 90° C. for 15 hours. After cooling, the reaction mixture is concentrated under reduced pressure. The residue is taken up between dichloromethane and water, the organic phase is separated and dried over sodium sulfate, and the filtrate is concentrated under reduced pressure. The residue is then purified by silica gel chromatography, elution being carried out with a dichloromethane/methanol mixture. The solid obtained is triturated with diethyl ether, recovered by filtration and then dried. 1.0 g of compound is obtained.

$^1$H NMR spectrum (DMSO-d6, δ in ppm): 1.4 (s, 9H); 2.3 (s, 3H); 4.55 (s, 2H); from 7.4 to 7.55 (m, 3H); 7.6 (s, 1H); 8.05 (m, 1H); from 8.2 to 8.4 (m, 2H); 8.55 (m, 1H). M+H=299.

1.2 5-(3-tert-Butoxymethylphenyl)pyridin-2-ylamine 559 mg of sodium hydroxide in 2 ml of ethanol and 2 ml of water are placed in a round-bottomed flask containing 695 mg of N-[5-(3-tert-butoxymethylphenyl)pyridin-2-yl]acetamide. 1 ml of water and 1 ml of ethanol are added thereto and the mixture is heated at the reflux of the solvent for 1 hour. After cooling, the reaction mixture is concentrated under reduced pressure. The residue is taken up between dichloromethane and water and the organic phase is then separated, dried over magnesium sulphate and concentrated under reduced pressure. The residue is purified by silica gel chromatography, elution being carried out with a dichloromethane/methanol mixture. 487 mg of compound are obtained.

$^1$H NMR spectrum (DMSO-d6, δ in ppm): 1.25 (s, 9H); 4.45 (s, 2H); 6.05 (s, 2H); 6.55 (d, 1H); 7.25 (d, 1H); 7.35 (t, 1H); 7.45 (d, 1H); 7.5 (s, 1H); 7.7 (m, 1H); 8.25 (s, 1H). M+H=257.

1.3 6-(3-tert-Butoxymethylphenyl)-2-pyridin-3-ylimidazo[1,2-a]pyridine 487 mg of 5-(3-tert-butoxymethylphenyl)pyridin-2-ylamine (obtained according to the protocol described in Example 1.2) and 380 mg of 2-bromo-1-pyridin-3-ylethanone in 15 ml of n-propanol are placed in a round-bottomed flask. 223 mg of sodium hydrogencarbonate are added. The reaction mixture is heated at 80° C. for 24 hours, left to cool to ambient temperature and concentrated under reduced pressure. The residue is taken up between water and ethyl acetate. The organic phase is separated and dried and the filtrate is concentrated under reduced pressure. The residue is purified by silica gel chromatography, elution being carried out with a dichloromethane/methanol mixture. 128 mg of compound are obtained.

M+H=358.

1.4 6-(3-tert-Butoxymethylphenyl)-2-(pyridin-3-yl)imidazo[1,2-a]pyridine hydrochloride (1:2)

121 mg of 6-(3-tert-butoxymethylphenyl)-2-pyridin-3-ylimidazo[1,2-a]pyridine are suspended in 5 ml of dichloromethane; 7.48 ml of a 0.1N solution of hydrochloric acid in 2-propanol are added thereto, dropwise and with stirring, and the mixture is stirred at ambient temperature for 7 hours. The mixture is concentrated under reduced pressure. The solid obtained is triturated with diethyl ether, recovered by filtration and oven-dried under reduced pressure at 40° C. The solid is then dissolved at ambient temperature in a minimum of isopropanol and then reprecipitated using isopropyl ether. The precipitate formed (after 3 h in a refrigerator) is recovered by filtration, washed with pentane and then oven-dried under reduced pressure at 50° C. 60 mg of compound are obtained.

Mp=220-222° C. $^1$H NMR spectrum (DMSO-d6, δ in ppm): 1.3 (s, 9H); 4.5 (s, 2H); 7.45 (d, 1H); 7.55 (t, 1H); from 7.65 to 7.75 (m, 2H); from 7.85 to 8.0 (m, 2H); 8.05 (d, 1H); from 8.75 to 8.90 (m, 3H); 9.15 (s, 1H); 9.4 (s, 1H). M+H=358.

EXAMPLE 2

[3-(2-Quinolin-3-ylimidazo[1,2-a]pyridin-6-yl)phenyl]methanol hydrochloride (1:2) (compound 5 of the table)

2.1 6-Bromo-3H-imidazo[1,2-a]pyridin-2-one 3.0 g of 5-bromopyridin-2-ylamine in 5.8 ml of ethyl 2-bromoacetate are placed in a round-bottomed flask and stirred at ambient temperature for 48 h. A precipitate forms, and is recovered by filtration, washed with diethyl ether and oven-dried under reduced pressure. The solid is then taken up in 50 ml of ethanol, and 2.18 g of sodium hydrogencarbonate are added thereto. The reaction mixture is heated at the reflux of the solvent for 5 h, cooled to ambient temperature, and then concentrated under reduced pressure. The residue obtained is taken up between water and dichloromethane and the organic phase is separated, dried and concentrated under reduced pressure. 1.46 g of compound, used as it is in the subsequent stages, are obtained.
M+H=214.

2.2 6-Bromo-2-chloroimidazo[1,2-a]pyridine

A mixture of 1.4 g of 6-bromo-3H-imidazo[1,2-a]pyridin-2-one in 5 ml of $POCl_3$ is heated at 105° C. for 2 hours and then cooled to ambient temperature and concentrated under reduced pressure. The residue is taken up between water and dichloromethane and a 30% aqueous solution of $NH_4OH$ is added until a basic pH is obtained. The organic phase is then separated, dried over magnesium sulphate and concentrated under reduced pressure. The residue is then purified by silica gel chromatography, elution being carried out with a dichloromethane/methanol mixture. 760 mg of compound are obtained.
$^1H$ NMR spectrum (DMSO-d6, δ in ppm): 7.35 (d, 1H); 7.55 (m, 2H); 8.3 (s, 1H). M+H=232.

2.3 [3-(2-Chloroimidazo[1,2-a]pyridin-6-yl)phenyl]methanol

In a round-bottomed flask, 760 mg of 6-bromo-2-chloroimidazo[1,2-a]pyridine are placed in 25 ml of toluene and 8 ml of ethanol and the mixture is degassed with argon for 10 min. After the addition of 230 mg of tetrakis(triphenylphosphine)palladium, the mixture is stirred for 5 min at ambient temperature and then 650 mg of 3-(hydroxymethyl)-phenylboronic acid and 8 ml of a 2M solution of sodium carbonate are added. The reaction mixture is heated at 80° C. for 16 h and then cooled to ambient temperature and concentrated under reduced pressure. The residue is taken up between water and ethyl acetate and the organic phase is separated, dried over magnesium sulphate and concentrated under reduced pressure. The oil obtained is purified by silica gel chromatography, elution being carried out with a heptane/ethyl acetate mixture. 550 mg of compound are obtained.
$^1H$ NMR spectrum (DMSO-d6, δ in ppm): 4.6 (d, 2H); 5.3 (t, 1H); from 7.35 to 7.75 (m, 6H); 8.1 (s, 1H); 8.85 (s, 1H). M+H=259.

2.4 [3-[2-(Quinolin-3-yl)imidazo[1,2-a]pyridin-6-yl]phenyl]methanol

In a screw reactor, 550 mg of [3-(2-chloroimidazo[1,2-a]pyridin-6-yl)phenyl]methanol, 550 mg of 3-quinolineboronic acid, 20 mg of palladium acetate, 70 mg of 2-dicyclohexylphosphino-2',6'-dimethoxy-1,1'-biphenyl and 900 mg of $K_3PO_4$ are placed in 8 ml of anhydrous toluene. The reactor is closed and heating is carried out at 115° C. for 16 h. After cooling, the reaction mixture is filtered through celite and rinsed with dichloromethane. The organic phase is washed with a saturated solution of NaCl, and then separated, dried and concentrated under reduced pressure. The residue is purified by silica gel chromatography, elution being carried out with a dichloromethane/methanol mixture. 90 mg of compound are obtained.
M+H=351.

2.5 [3-[2-(Quinolin-3-yl)imidazo[1,2-a]pyridin-6-yl]phenyl]methanol hydrochloride (1:2)

A solution of 90 mg of [3-[(2-quinolin-3-yl)imidazo[1,2-a]pyridin-6-yl]phenyl]methanol in dichloromethane and methanol is passed through sintered glass and then 5.2 ml of a 0.1N solution of hydrochloric acid in isopropanol is added to the filtrate. A precipitate forms, and is collected by filtration and washed with diethyl ether. The solid is then dissolved at ambient temperature with the minimum amount of methanol and then taken up with diethyl ether. The precipitate is recovered by filtration and oven-dried under reduced pressure. 66 mg of compound are obtained.
Mp=279-281° C. $^1H$ NMR spectrum (DMSO-d6, δ in ppm): 4.65 (s, 2H); 7.45 (d, 1H); 7.55 (t, 1H); 7.7 (d, 1H); 7.8 (m, 2H); 7.95 (m, 1H); 8.0 (m, 1H); 8.1 (m, 1H); 8.2 (m, 2H); 8.95 (s, 1H); 9.15 (s, 1H); 9.2 (s, 1H); 9.6 (s, 1H). M+H=445.

EXAMPLE 3

[2-[2-(Furan-3-yl)imidazo[1,2-a]pyridin-6-yl]phenyl]methanol hydrochloride (1:1) (compound 12 of the table)

3.1 Ethyl[2-imino-5-(4,4,5,5-tetramethyl-1,3,2-dioxaborolan-2-yl)-2H-pyridin-1-yl]acetate hydrobromide 5.0 g of 5-(4,4,5,5-tetramethyl-1,3,2-dioxaborolan-2-yl)pyridin-2-ylamine in 7.6 ml of ethyl 2-bromoacetate are placed in a round-bottomed flask and the mixture is stirred at ambient temperature for 20 h. A precipitate forms, and is recovered by filtration, washed with diethyl ether and then with ethanol and oven-dried under reduced pressure. 8.78 g of compound are obtained.
$^1H$ NMR spectrum (DMSO-d6, δ in ppm): 1.3 (m, 15H); from 4.1 to 4.25 (m, 2H); 5.2 (s, 2H); 7.1 (d, 1H); 8.0 (d, 1H); 8.3 (s, 1H); 9.0 (s, 1H). M+H=388.

3.2 2-Chloro-6-(4,4,5,5-tetramethyl-1,3,2-dioxaborolan-2-yl)imidazo[1,2-a]pyridine In a round-bottomed flask, 8.78 g of compound obtained according to the protocol described in 3.1 are placed in 20 ml of $POCl_3$. The reaction mixture is heated at 105° C. for 16 h, cooled to ambient temperature and concentrated under reduced pressure. The residue is taken up between dichloromethane and water at 0° C., and a 30% aqueous solution of $NH_4OH$ is added until a basic pH is obtained. The organic phase is separated, dried over magnesium sulphate and concentrated under reduced pressure. 4.3 g of compound are obtained.
Mp=115-120° C. $^1H$ NMR spectrum (DMSO-d6, δ in ppm): 1.35 (m, 12H); 7.4 (d, 1H); 7.5 (d, 1H); 8.1 (s, 1H); 8.85 (s, 1H). M+H=279.

3.3 (2-Bromobenzyloxy)tert-butyldimethylsilane 2.0 g of (2-bromophenyl)methanol are placed in a round-bottomed flask and dissolved in 100 ml of tetrahydrofuran. 1.1 g of 1H-imidazole are added thereto, followed by 2.1 g of tert-butyldimethylsilane chloride, and the mixture is left to stir at ambient temperature for 48 hours. The reaction mixture is then hydrolysed with water, and the organic phase, which has been extracted with ethyl acetate, is separated, dried over magnesium sulphate and concentrated under reduced pressure. The residue obtained is purified by silica gel chromatography, elution being carried out with a heptane/ethyl acetate mixture. 2.66 g of compound are obtained.

$^1$H NMR spectrum (CDCl$_3$, δ in ppm): 0 (s, 6H); 0.8 (s, 9H); 4.6 (s, 2H); 6.95 (m, 1H); 7.2 (m, 1H); from 7.35 to 7.45 (m, 2H). M+H=302.

3.4 6-[2-[(tert-Butyldimethylsilanyl)oxymethyl]phenyl-2-chloroimidazo[1,2-a]pyridine 450 mg of (2-bromobenzyloxy)-tert-butyldimethylsilane, 500 mg of 2-chloro-6-(4,4,5,5-tetramethyl-1,3,2-dioxaborolan-2-yl)imidazo[1,2-a]pyridine and 1.46 g of caesium carbonate are dissolved in 8 ml of tetrahydrofuran and 1 ml of water. The mixture is degassed with argon for 10 min, 110 mg of [1,1'-bis(diphenylphosphino)-ferrocene]dichloropalladium are added and the mixture is heated at the reflux of the solvent for 16 hours. After cooling, the reaction mixture is hydrolysed with water, and the organic phase, which has been extracted with dichloromethane, is separated, dried and concentrated under reduced pressure. The oil obtained is purified by silica gel chromatography, elution being carried out with a heptane/ethyl acetate mixture. 260 mg of compound are obtained.

$^1$H NMR spectrum (CDCl$_3$, δ in ppm): 0 (s, 6H); 0.85 (s, 9H); 4.5 (s, 2H); from 7.15 to 7.55 (m, 7H); 8.15 (s, 1H). M+H=373.

3.5 6-[2-[(tert-Butyldimethylsilanyl)oxymethyl]phenyl]-2-(furan-3-yl)imidazo[1,2-a]pyridine 3 mg of palladium acetate, 11 mg of 2-(dicyclohexyl)phosphino-2',6'-dimethoxy-1,1'-biphenyl, 270 mg of K$_3$PO$_4$, 110 mg of 3-furanboronic acid and a few drops of ethanol are placed in a reactor containing a mixture of 240 mg of 6-[2-[(tert-butyldimethylsilanyl)oxymethyl]phenyl]-2-chloroimidazo[1,2-a]pyridine in 2 ml of toluene degassed beforehand under an argon stream. The reactor is closed and heated at 115° C. for 16 h. After cooling, the reaction mixture is filtered through celite, washed with dichloromethane and then concentrated under reduced pressure. The residue is purified by silica gel chromatography, elution being carried out with a dichloromethane/methanol mixture. 258 mg of compound are obtained.

$^1$H NMR spectrum (CDCl$_3$, δ in ppm): 0 (s, 6H); 0.85 (s, 9H); 4.55 (s, 2H); 6.75 (m, 1H); from 7.1 to 7.6 (m, 8H); 7.95 (s, 1H); 8.15 (s, 1H). M+H=405.

3.6 [2-[2-(Furan-3-yl)imidazo[1,2-a]pyridin-6-yl]phenyl]methanol 250 mg of 6-[2-[(tert-butyldimethylsilanyloxy)methyl]phenyl]-2-(furan-3-yl)imidazo[1,2-a]pyridine in 6 ml of tetrahydrofuran are placed in a round-bottomed flask, and 320 mg of tetrabutylammonium fluoride are added thereto. The reaction mixture is stirred at ambient temperature for 48 h and concentrated under reduced pressure. The residue is purified by silica gel chromatography, elution being carried out with a dichloromethane/methanol mixture. 156 mg of compound are obtained.

M+H=291.

3.7 [2-(2-(Furan-3-yl)imidazo[1,2-a]pyridin-6-yl)phenyl]methanol hydrochloride (1:1)

156 mg of [2-(2-furan-3-ylimidazo[1,2-a]pyridin-6-yl)phenyl]methanol are suspended in dichloromethane; 5.4 ml of a 0.1N solution of hydrochloric acid in isopropanol are added thereto, dropwise, and the mixture is stirred at ambient temperature. The reaction mixture is then concentrated under reduced pressure. The residual solid is taken up in diethyl ether and the precipitate is recovered by filtration, washed with diethyl ether and oven-dried under reduced pressure.

Mp=205-208° C. $^1$H NMR spectrum (DMSO-d6, δ in ppm): 4.45 (s, 2H); 7.1 (m, 1H); 7.4 (m, 1H); 7.45 (t, 1H); 7.5 (t, 1H); 7.65 (d, 1H); from 7.9 to 8.0 (m, 3H); 8.45 (s, 1H); 8.55 (s, 1H); 8.95 (s, 1H). M+H=327.

EXAMPLE 4

{3-[2-(1H-indol-6-yl)imidazo[1,2-a]pyridin-6-yl]phenyl}methanol hydrochloride (1:1) (compound No. 33 of the table)

4.1 Ethyl (5-bromo-2-imino-1H-pyridin-1-yl)acetate hydrobromide

By carrying out the process as in Example 3.1 and using 5.0 g of 5-bromopyridin-2-ylamine and 9.6 ml of ethyl 2-bromoacetate, 9.56 g of compound are obtained.

$^1$H NMR spectrum (DMSO-d6, δ in ppm): 1.3 (t, 3H); 4.25 (q, 2H); 5.15 (s, 2H); 7.15 (d, 1H); 8.1 (d, 1H); 8.45 (s, 1H); 8.95 (s, 1H); M+H=341.

4.2 6-Bromo-2-chloroimidazo[1,2-a]pyridine

By carrying out the process as in Example 3.2, starting from 9.5 g of ethyl (5-bromo-2-imino-1H-pyridin-1-yl)acetate hydrobromide and 30 ml of POCl$_3$, 6.7 g of 6-bromo-2-chloroimidazo[1,2-a]pyridine are obtained. The compound is purified by silica gel chromatography, elution being carried out with a heptane/ethyl acetate mixture. 5.97 g of compound are obtained.

Mp=155-159° C. 1H NMR spectrum (CDCl$_3$, δ in ppm): 7.35 (d, 1H); from 7.45 to 7.6 (m, 2H); 8.3 (s, 1H); M+H=232.

4.3 6-[3-[(tert-Butyldimethylsilanyloxy)methyl]phenyl]-2-chloroimidazo[1,2-a]pyridine 5.7 g of [3-(2-chloroimidazo[1,2-a]pyridin-6-yl)phenyl]methanol, obtained according to the protocol described in Example 2.3, in 220 ml of tetrahydrofuran are placed in a round-bottomed flask, and then 1.95 g of 1H-imidazole and 3.65 g of tert-butyldimethylsilane chloride are added and the mixture is left to stir at ambient temperature for 48 hours. The reaction mixture is then hydrolysed with 150 ml of water, and the organic phase, which has been extracted with ethyl acetate, is separated, dried over magnesium sulphate and concentrated under reduced pressure. The residual solid is purified by silica gel chromatography, elution being carried out with a heptane/ethyl acetate mixture. 6.1 g of compound are obtained.

¹H NMR spectrum (CDCl₃, δ in ppm): 0.10 (s, 6H); 0.92 (s, 9H); 4.79 (s, 2H); 7.37 (d, 1H); from 7.55 to 7.67 (m, 5H); 8.05 (s, 1H); 8.84 (t, 1H). Mp=120-123° C. M+H=373.

4.4 6-[3-[(tert-Butyldimethylsilanyloxy)methyl]phenyl]-2-(1H-indol-6-yl)imidazo[1,2-a]pyridine 200 mg of 6-[3-[(tert-butyldimethylsilanyloxy)methyl]phenyl]-2-chloroimidazo[1,2-a]pyridine in 2 ml of toluene are placed in a reactor and degassed under an argon stream for 10 min, and then 3 mg of palladium acetate, 11 mg of 2-(dicyclohexyl)phosphino-2',6'-dimethoxy-1,1'-biphenyl, 110 mg of 6-indoleboronic acid, 230 mg of K₃PO₄ and a few drops of ethanol are added. The reactor is closed and heated at 115° C. for 16 h. After cooling, the reaction mixture is concentrated under reduced pressure and the residue obtained is then purified by silica gel chromatography, elution being carried out with a heptane/ethyl acetate mixture. 180 mg of compound are obtained.
¹H NMR spectrum (CDCl₃, δ in ppm): 0 (s, 6H); 0.85 (s, 9H); 4.7 (s, 2H); 6.4 (m, 1H); 7.1 (m, 1H); from 7.2 to 7.35 (m, 4H); 7.4 (s, 1H); 7.55 (m, 2H); 7.8 (s, 1H); 8.05 (s, 1H); 8.15 (s, 1H) 8.35 (m, 1H) 11.5 (s, 1H); M+H=454.

4.5 {3-[2-(1H-Indol-6-yl)imidazo[1,2-a]pyridin-6-yl]phenyl}methanol 210 mg of tetrabutylammonium fluoride are introduced into a round-bottomed flask containing 180 mg of 6-[3-[(tert-butyldimethylsilanyloxy)methyl]phenyl]-2-(1H-indol-6-yl)imidazo[1,2-a]pyridine in 4 ml of tetrahydrofuran. The reaction mixture is stirred at ambient temperature for 48 h and is concentrated under reduced pressure. The residue is purified by silica gel chromatography, elution being carried out with a dichloromethane/methanol mixture. 117 mg of compound are obtained.
¹H NMR spectrum (DMSO-d6, δ in ppm): 4.65 (d, 2H); 5.3 (t, 1H); 6.5 (m, 1H); 7.4 (m, 2H); 7.5 (t, 1H); from 7.6 to 7.75 (m, 6H); 8.1 (s, 1H); 8.4 (s, 1H); 8.9 (s, 1H); 11.2 (s, 1H). M+H=340.

4.6 {3-[2-(1H-Indol-6-yl)imidazo[1,2-a]pyridin-6-yl]phenyl}methanol hydrochloride (1:1)

110 mg of {3-[2-(1H-indol-6-yl)imidazo[1,2-a]pyridin-6-yl]phenyl}methanol are suspended in dichloromethane and methanol; 3.2 ml of a 0.1N solution of hydrochloric acid in isopropanol are added thereto, dropwise. The reaction mixture is then concentrated under reduced pressure. The residual solid is taken up in diethyl ether, and the precipitate is recovered by filtration and oven-dried under reduced pressure.
Mp=251-254° C. ¹H NMR spectrum (DMSO-d6, δ in ppm): 4.65 (s, 2H); 6.55 (s, 1H); 7.45 (d, 1H); 7.55 (m, 2H); 7.65 (d, 1H); 7.7 (d, 1H); 7.75 (m, 2H); 8.0 (d, 1H); 8.1 (s, 1H); 8.25 (d, 1H); 8.7 (s, 1H); 9.25 (s, 1H); 11.6 (s, 1H). M+H=376.

EXAMPLE 5

[3-[2-(Benzofuran-3-yl)imidazo[1,2-a]pyridin-6-yl]phenyl]methanol (compound 23 of the table)

5.1 2-(Benzofuran-3-yl)-6-bromoimidazo[1,2-a]pyridine

In a glass tube, 250 mg of 1-(benzofuran-3-yl)-2-bromoethanone, 181 mg of 5-bromopyridin-2-ylamine and 105 mg of sodium hydrogencarbonate are dissolved in 15 ml of n-propanol. The tube is closed and heated at 80° C. for 20 h. After cooling, 20 ml of water are added and the reaction mixture is stirred for 1 hour at ambient temperature. A precipitate forms, and is recovered by filtration, washed with water and then with diisopropyl ether, and dried in a desiccator under reduced pressure. 250 mg of compound are obtained.
Mp=151-153° C. ¹H NMR (DMSO-d6, δ in ppm): from 7.31 to 7.43 (m, 3H); from 7.53 to 7.68 (m, 2H); 8.15 (m, 1H); 8.42 (s, 1H); 8.50 (s, 1H); 8.87 (m, 1H). M+H=314.

5.2 [3-(2-(Benzofuran-3-yl)imidazo[1,2-a]pyridin-6-yl)phenyl]methanol 100 mg of 2-(benzofuran-3-yl)-6-bromoimidazo[1,2-a]pyridine, 73 mg of 3-(hydroxymethyl)phenylboronic acid and 11 mg of tetrakis(triphenylphosphine)palladium are placed in a microwave tube. 2 ml of acetonitrile, 2 ml of toluene and 1.5 ml of a 2M solution of sodium carbonate are added thereto. The tube is placed in a microwave device and irradiated at 150° C. for 15 min. The organic phase is separated, dried, and then concentrated under reduced pressure. The oily residue is taken up with 3 ml of dichloromethane and triturated for 1 hour. The precipitate is recovered by filtration, washed with diisopropyl ether and dried in a desiccator under reduced pressure. 44 mg of compound are obtained.
Mp=150-152° C. ¹H NMR (DMSO-d6, δ in ppm): 4.6 (d, 2H); 5.25 (t, 1H); from 7.25 to 7.75 (m, 9H); 8.2 (m, 1H); 8.45 (s, 1H); 8.5 (s, 1H); 8.9 (t, 1H). M+H=341.

EXAMPLE 6

[3-(3-Methyl-2-thien-2-ylimidazo[1,2-a]pyridin-6-yl)phenyl]methanol hydrochloride (1:1) (compound 31 of the table)

6.1 [3-(6-Aminopyridin-3-yl)phenyl]methanol 2.0 g of tetrakis(triphenylphosphine)palladium and 75 ml of a 2M solution of sodium carbonate are added to a round-bottomed flask containing a solution of 5.0 g of 5-bromopyridin-2-ylamine and 5.7 g of 3-(hydroxymethyl)phenylboronic acid in 140 ml of toluene, and 70 ml of ethanol degassed beforehand. The mixture is heated at 80° C. for 16 h. After cooling, the reaction mixture is concentrated under reduced pressure. The residue is taken up between water and ethyl acetate. The organic phase is separated, dried and concentrated under reduced pressure. The residue is purified by silica gel chromatography, elution being carried out with a dichloromethane/methanol mixture. 4.99 g of compound are obtained.
¹H NMR (DMSO-d6, δ in ppm): 4.55 (d, 2H); 5.2 (t, 1H); 6.05 (s, 2H); 6.55 (d, 1H); 7.2 (d, 1H); from 7.3 to 7.55 (m, 3H); 7.7 (d, 1H); 8.25 (s, 1H); M+H=201.

6.2 5-[3-(tert-Butyldimethylsilanyloxymethyl)phenyl]pyridin-2-ylamine 4.99 g of [3-(6-aminopyridin-3-yl)phenyl]methanol are placed in a round-bottomed flask and dissolved in 240 ml of tetrahydrofuran. 2.2 g of 1H-imidazole are added thereto, followed by 4.51 g of tert-butyldimethylsilane chloride, and the mixture is left to stir at ambient temperature for 48 hours. The reaction mixture is then hydrolysed with water, and the organic phase, which has been extracted with ethyl acetate, is separated, dried over magnesium sulphate and concentrated under reduced pressure. The residue obtained is purified by silica gel chromatography, elution being carried out with a heptane/ethyl acetate mixture. 7.0 g of compound are obtained.

$^1$H NMR (DMSO-d6, δ in ppm): 0.09 (s, 6H); 0.91 (s, 9H); 4.75 (s, 2H); 6.02 (m, 2H); 6.52 (dd, 1H); 7.21 (d, 1H); 7.36 (t, 1H); 7.43 (d, 1H); 7.47 (s, 1H); 7.66 (dd, 1H); 8.21 (d, 1H). M+H=315; Mp=82-84° C.

6.3 6-[3-(tert-Butyldimethylsilanyloxymethyl)phenyl]-3-methyl-2-thien-2-ylimidazo[1,2-a]pyridine In a glass tube, 280 mg of 5-[3-(tert-butyldimethylsilanyloxymethyl)phenyl]pyridin-2-ylamine, 390 mg of 2-bromo-1-thiophen-2-ylpropan-1-one and 190 mg of sodium hydrogencarbonate are dissolved in 5 ml of ethanol. The tube is closed and heated at 100° C. for 20 h. After cooling, the mixture is concentrated under reduced pressure. The residue is purified by silica gel chromatography, elution being carried out with a heptane/ethyl acetate mixture. 260 mg of compound are obtained.

$^1$H NMR spectrum (CDCl$_3$, δ in ppm): 0 (s, 6H); 0.85 (s, 9H); 2.6 (s, 3H); 4.7 (s, 2H); 7 (m, 1H); from 7.2 to 7.6 (m, 8H); 7.45 (s, 1H); 7.9 (s, 1H); M+H=435.

6.4 [3-(3-Methyl-2-thien-2-ylimidazo[1,2-a]pyridin-6-yl)phenyl]methanol 310 mg of tetrabutylammonium fluoride are introduced into a round-bottomed flask containing 260 mg of 6-[3-(tert-butyldimethylsilanyloxymethyl)phenyl]-3-methyl-2-thien-2-ylimidazo[1,2-a]pyridine in 6 ml of tetrahydrofuran. The reaction mixture is stirred at ambient temperature for 48 h and is concentrated under reduced pressure. The residue is purified by silica gel chromatography, elution being carried out with a dichloromethane/methanol mixture. 140 mg of compound are obtained. M+H=321

6.5 [3-(3-Methyl-2-thien-2-ylimidazo[1,2-a]pyridin-6-yl)phenyl]methanol hydrochloride (1:1)

140 mg of [3-(3-methyl-2-thien-2-ylimidazo[1,2-a]pyridin-6-yl)phenyl]methanol are suspended in dichloromethane and methanol; 3.2 ml of a 0.1N solution of hydrochloric acid in isopropanol are added thereto, dropwise. The reaction mixture is then concentrated under reduced pressure. The residual solid is taken up in diethyl ether, and the precipitate is recovered by filtration and oven-dried under reduced pressure. 150 mg of compound are obtained.

$^1$H NMR spectrum (DMSO-d6, δ in ppm): 2.85 (s, 3H); 4.75 (s, 2H); 7.35 (m, 1H); 7.45 (d, 1H); 7.55 (t, 1H); 7.75 (d, 1H); 7.85 (m, 2H); 7.9 (d, 1H); 7.95 (d, 1H); 8.2 (d, 1H); 8.95 (s, 1H); M+H=321; Mp=279-283° C.

EXAMPLE 7

2-{3-[2-(1H-Indol-6-yl)imidazo[1,2-a]pyridin-6-yl]phenyl}propan-2-ol (compound 47 of the table)

7.1 2-(3-Bromophenyl)propan-2-ol

Under an argon stream, 6.5 g of 3-bromoacetophenone are placed in a round-bottomed flask and dissolved in 544 ml of diethyl ether and 272 ml of tetrahydrofuran. The mixture is cooled to 0° C. using an ice bath, and 100 ml of a 1M solution of methylmagnesium bromide in dibutyl ether are added thereto, dropwise. The mixture is stirred at 0° C. for 1 h and 400 ml of a saturated aqueous solution of ammonium chloride are added. The organic phase is separated, dried over magnesium sulphate and concentrated under reduced pressure. 10.0 g of compound are obtained. $^1$H NMR (DMSO-d6, δ in ppm): 1.45 (s, 6H); 5.15 (s, 1H); 7.25 (t, 1H); 7.4 (d, 1H); 7.45 (d, 1H); 7.65 (s, 1H).

7.2 2-[3-(2-Chloroimidazo[1,2-a]pyridin-6-yl)-phenyl]propan-2-ol 85.5 ml of tetrahydrofuran and 9.5 ml of water are placed in a round-bottomed flask, the mixture is degassed with argon for 10 min, and 5.8 g of the compound obtained in 7.1, 4.48 g of 2-chloro-6-(4,4,5,5-tetramethyl-1,2,3-dioxaborolan-2-yl)imidazo[1,2-a]pyridine obtained in 3.2, 20.35 g of caesium carbonate and 0.85 g of [1,1'-bis(diphenylphosphino)-ferrocene]dichloropalladium are successively added. The mixture is stirred for 2 hours at the reflux of tetrahydrofuran. After cooling to ambient temperature, the solvents are evaporated off under reduced pressure. The residue is taken up between water and ethyl acetate. The organic phase, washed twice with a saturated solution of sodium chloride, is then dried over magnesium sulphate and concentrated under reduced pressure. The residue obtained is purified by silica gel chromatography, elution being carried out with a dichloromethane/ethyl acetate mixture. The solid obtained is triturated with a diisopropyl ether, recovered by filtration, and then oven-dried under reduced pressure. 2.31 g of compound are obtained. 1H NMR (DMSO-d6, δ in ppm): 1.5 (s, 6H); 5.1 (s, 1H); 7.45 (m, 1H); 7.55 (m, 2H); from 7.6 to 7.7 (m, 2H); 7.8 (s, 1H); 8.05 (s, 1H); 8.85 (s, 1H).

7.3 2-{3-[2-(1H-Indol-6-yl)imidazo[1,2-a]pyridin-6-yl]phenyl}propan-2-ol 4 mg of palladium acetate, 14 mg of 2-(dicyclohexyl)phosphino-2',6'-dimethoxy-1,1'-biphenyl, 175 mg of indole-6-boronic acid, 355 mg of K$_3$PO$_4$ and a few drops of ethanol are placed in a reactor containing a mixture of 250 mg of compound obtained in stage 7.2 in 3.1 ml of anhydrous toluene degassed beforehand under an argon stream. The reactor is closed and heated at 115° C. for 16 hours. After cooling, the reaction mixture is filtered through celite and then concentrated under reduced pressure. The residue obtained is purified by silica gel chromatography, elution being carried out with a heptane/ethyl acetate mixture. 210 mg of compound are obtained. Mp=203-204° C.

$^1$H NMR (DMSO-d6, δ in ppm): 1.55 (s, 6H); 5.1 (s, 1H); 6.45 (s, 1H); from 7.4 to 7.75 (m, 8H); 7.85 (s, 1H); 8.05 (s, 1H); 8.4 (s, 1H); 8.85 (s, 1H); 11.2 (s, 1H).

EXAMPLE 8

2-[3-(2-Thien-3-ylimidazo[1,2-a]pyridin-6-yl)phenyl]propan-2-ol (compound 49 of the table)

8.1 2-[3-(6-Aminopyridin-3-yl)phenyl]propan-2-ol

Under an argon stream, the following are placed in a round-bottomed flask: 9.0 g of compound obtained in stage 7.1, 11.05 g of 5-(4,4,5,5-tetramethyl-1,3,2-dioxaborolan-2-yl)pyridin-2-ylamine, 83.7 ml of a 2M solution of sodium carbonate and 1.70 g of tetrakis(triphenylphosphine)palladium, and dissolved in 523 ml of N,N-dimethylformamide. The mixture is heated for 1 h 30 at 80° C. After cooling to ambient temperature, 1 l of ethyl acetate is added to the reaction medium, which is filtered through celite. The organic phase is then separated, washed three times with a saturated solution of sodium chloride, dried over magnesium sulphate and concentrated under reduced pressure. The residue is purified by silica gel chromatography, elution being carried out with a dichloromethane/methanol mixture. The solid obtained is triturated from diisopropyl ether, recovered by filtration and then oven-dried under reduced pressure. 2.35 g of compound are obtained.

$^1$H NMR (DMSO-d6, δ in ppm): 1.45 (s, 6H); 5.0 (s, 1H); 6.0 (s, 2H); 6.55 (d, 1H); from 7.3 to 7.4 (m, 3H); 7.65 (s, 1H); 7.7 (d, 1H); 8.25 (s, 1H).

8.2 2-[3-(2-Thien-3-ylimidazo[1,2-a]pyridin-6-yl)phenyl]propan-2-ol (compound 49 of the table)

58 mg (0.7 mmol) of sodium bicarbonate are weighed into a microwave tube. 57 mg (0.25 mmol) of the compound obtained in 8.1, in solution in 2 ml of propan-1-ol, are added thereto, followed by 92 mg (0.375 mmol) of 2-bromo-1-(thienyl-3-yl)ethanone in solution in 1 ml of propan-1-ol. The tube is sealed and then stirred at 80° C. for 16 hours. The reaction mixture is cooled to ambient temperature, 200 mg of propanethiol supported on silica (Biotage Si-Thiol) are added thereto, and the mixture is stirred for 6 h at ambient temperature and then filtered. The residue is washed with twice 2 ml of propan-1-ol, and then the filtrate is evaporated and purified by chromatography. 34.2 mg of compound are obtained.

$^1$H NMR (DMSO-d6, δ in ppm): 1.5 (s, 6H); 5.1 (s, 1H); 7.45 (t, 1H); from 7.5 to 7.55 (m, 2H); from 7.6 to 7.7 (m, 4H); 7.8 (s, 1H); 7.95 (d, 1H); 8.3 (s, 1H); 8.9 (s, 1H). M+H=335.

EXAMPLE 9

[2-(2-Benzothiazol-2-ylimidazo[1,2-a]pyridin-6-yl)-6-fluorophenyl]methanol (compound 69 of the table)

9.1 (2-Bromo-6-fluorophenyl)methanol 20.0 g (0098 mol) of 2-bromo-6-fluorobenzaldehyde are dissolved in 500 ml of methanol and cooled in an ice bath; 3.72 g (0.098 mol) of sodium borohydride are then added thereto, portionwise. The mixture is stirred under cold conditions for 1 hour and the solvent is then evaporated off under reduced pressure. The residue is taken up between water and dichloromethane, and the organic phase is separated, dried and concentrated under reduced pressure. The residue is crystallized from pentane. 18.1 g of compound are obtained.

$^1$H NMR (CDCl$_3$, δ in ppm): 2.15 (t, 1H); 4.95 (d, 2H); from 7.05 to 7.3 (m, 2H); 7.45 (d, 1H).

9.2 (2-Bromo-6-fluorobenzyloxy)-tert-butyldimethylsilane

In a 500 ml round-bottomed flask, 15.7 g (0.076 mol) of the compound obtained previously are dissolved in 230 ml of THF, and 7.8 g (0.115 mol) of imidazole are added, followed by 13.8 g (0.092 mol) of tert-butyldimethylsilane chloride, and the reaction mixture is stirred for 16 hours. The solvent is then evaporated off under reduced pressure, the residue is taken up between water and diethyl ether, the resulting product is separated by settling out, and the organic phase is washed with water and dried over sodium sulphate. After evaporation of the solvent, 25 g of oil are recovered.

$^1$H NMR (CDCl$_3$, δ in ppm): 0.0 (s, 6H); 0.8 (s, 9H); 4.7 (s, 2H); from 6.8 to 7.05 (m, 2H); 7.25 (d, 1H).

9.3 5-[2-(tert-Butyldimethylsilanyloxymethyl)-3-fluorophenyl]pyridin-2-ylamine 6.4 g of the compound obtained in 9.2, 4.40 g of 5-(4,4,5,5-tetramethyl-1,3,2-dioxaborolan-2-yl)pyridin-2-ylamine, 30 ml of a 2M solution of sodium carbonate and 816 mg of [1,1'-bis(diphenylphosphino)ferrocene]dichloropalladium are dissolved in 80 ml of N,N-dimethylformamide and placed in a round-bottomed flask under an argon stream. The mixture is heated for 2 h at 80° C. After cooling to ambient temperature, the solvents are evaporated off under reduced pressure and the residue is taken up between water and ethyl acetate and an insoluble material is removed by filtration through celite. The organic phase is separated by settling out, washed with a saturated aqueous solution of sodium chloride and dried over sodium sulphate. The compound is purified by chromatography, elution being carried out with a mixture of dichloromethane and methanol. 4.58 g of oil are obtained.

$^1$H NMR (DMSO-d6, δ in ppm): 0 (s, 6H); 0.85 (s, 9H); 4.5 (s, 2H); 6.05 (s, 2H); 6.45 (d, 1H); from 7.05 to 7.15 (m, 2H); from 7.3 to 7.4 (m, 1H); from 7.45 to 7.5 (m, 1H); 8.0 (d, 1H). M+H=333

9.4 2-{6-[2-(tert-Butyldimethylsilanyloxymethyl)-3-fluorophenyl]imidazo[1,2-a]pyridin-2-yl}benzothiazole 58 mg (0.7 mmol) of sodium bicarbonate are weighed into a microwave tube. 83 mg (0.25 mmol) of the compound obtained in 9.3, in solution in 2 ml of propan-1-ol, are added thereto, followed by 0.375 mmol of 1-(benzothiazol-2-yl)-2-bromoethanone in solution in 1 ml of propan-1-ol. The tube is sealed and then stirred at 80° C. for 16 hours. The reaction mixture is cooled to ambient temperature, 200 mg of propanethiol supported on silica (Biotage Si-Thiol) are added thereto, and the mixture is stirred for 6 h at ambient temperature and then filtered, and the filtrate is evaporated under reduced pressure. The compound is used as it is for the subsequent stage.

9.5 [2-(2-Benzothiazol-2-ylimidazo[1,2-a]pyridin-6-yl)-6-fluorophenyl]methanol The crude compound obtained in 9.4 is dissolved in 5 ml of THF containing 0.5 mmol of tetrabutylammonium fluoride hydrate. The mixture is stirred for 16 h at ambient temperature, and the solvent is then evaporated off under reduced pressure. The compound is purified by chromatography. 37.5 mg of compound are obtained.

$^1$H NMR (DMSO-d6, δ in ppm): 4.45 (d, 2H); 5.3 (t, 1H); from 7.25 to 7.35 (m, 2H); from 7.45 to 7.5 (m, 2H); from 7.5 to 7.6 (m, 2H); 7.75 (d, 1H); 8.05 (d, 1H); 8.15 (d, 1H); 8.7 (s, 1H); 8.75 (s, 1H). M+H=376.

EXAMPLE 10

[2,6-Difluoro-3-(3-methyl-2-thien-2-ylimidazo[1,2-a]pyridin-6-yl)phenyl]methanol (compound 75 of the table)

10.1 (3-bromo-2,6-difluorophenyl)methanol 20 g of 3-bromo-2,6-difluorobenzaldehyde are dissolved in 450 ml of methanol and cooled in an ice bath; 3.42 g of sodium borohydride are then added thereto, portionwise. The mixture is stirred at ambient temperature for 1 hour and the solvent is then evaporated off under reduced pressure. The residue is taken up between water and dichloromethane. The organic phase is separated, dried and concentrated under reduced pressure. The residue is crystallized from n-pentane. 14.6 g of compound are obtained.

¹H NMR spectrum (CDCl₃, δ in ppm): 2.0 (s, 1H); 4.9 (s, 2H); from 6.85 to 7.0 (m, 1H); from 7.5 to 7.65 (m, 1H).

10.2 (3-Bromo-2,6-difluorobenzyloxy)-tert-butyldimethylsilane 11.15 g of the compound obtained in 10.1 are dissolved in 150 ml of THF, 5.1 g of imidazole and then 9.04 g of tert-butyldimethylsilane chloride are added, and the mixture is stirred at ambient temperature for 24 hours. The solvent is then evaporated off, the residue is taken up with water and diethyl ether, and the organic phase is separated by settling out, washed with water and dried over sodium sulphate. The solvent is evaporated off under reduced pressure. 17.5 g of oil are obtained.
¹H NMR spectrum (CDCl₃, δ in ppm): 0.0 (s, 6H); 0.8 (s, 9H); 4.65 (s, 2H); from 6.65 to 6.7 (m, 1H); from 7.3 to 7.4 (m, 1H).

10.3 5-[3-(tert-Butyldimethylsilanyloxymethyl)-2,4-difluorophenyl]pyridin-2-ylamine 6.7 g of the compound obtained in 10.2, 4.40 g of 5-(4,4,5,5-tetramethyl-1,3,2-dioxaborolan-2-yl)pyridin-2-ylamine, 30 ml of a 2M solution of sodium carbonate and 816 mg of [1,1'-bis(diphenylphosphino)ferrocene]dichloropalladium are dissolved in 80 ml of N,N-dimethylformamide and placed in a round-bottomed flask under an argon stream. The mixture is heated for 2 h at 80° C. After cooling to ambient temperature, the solvents are evaporated off under reduced pressure and the residue is taken up between water and ethyl acetate and an insoluble material is removed by filtration through celite. The organic phase is separated by settling out, washed with a saturated aqueous solution of sodium chloride and dried over sodium sulphate. The compound is purified by chromatography, elution being carried out with a mixture of dichloromethane and methanol. 4.25 g of a white solid are obtained.
¹H NMR (DMSO-d6, δ in ppm): 0 (s, 6H); 0.8 (s, 9H); 4.4 (s, 2H); 6.05 (s, 2H); 6.45 (d, 1H); 7.05 (t, 1H); from 7.35 to 7.45 (m, 2H); 8.0 (s, 1H). M+H=351.

10.4 6-[3-(tert-Butyldimethylsilanyloxymethyl)-2,4-difluorophenyl]-3-methyl-2-thien-2-ylimidazo[1,2-a]pyridine 58.8 mg (0.7 mmol) of sodium bicarbonate are weighed into a microwave tube. 83 mg (0.25 mmol) of the compound obtained in 10.3, in solution in 2 ml of propan-1-ol, are added thereto, followed by 0.375 mmol of 2-bromo-1-(thien-2-yl)propan-1-one in solution in 1 ml of propan-1-ol. The tube is sealed and then irradiated for 10 min at 180° C. The reaction mixture is cooled to ambient temperature, 200 mg of propanethiol supported on silica (Biotage Si-Thiol) are added thereto, and the mixture is stirred for 6 h at ambient temperature and then filtered. The residue is washed with twice 2 ml of propan-1-ol, and the filtrate is then evaporated. The compound is used as it is for the subsequent stage.

10.5 [2,6-Difluoro-3-[3-methyl-2-(thien-2-yl)imidazo[1,2-a]pyridin-6-yl]phenyl]methanol The crude compound obtained in 10.4 is dissolved in 5 ml of THF containing 0.5 mmol of tetrabutylammonium fluoride hydrate. The mixture is stirred for 16 h at ambient temperature, and the solvent is then evaporated off under reduced pressure. The compound is purified by chromatography. 21.2 mg of compound are obtained.
¹H NMR (DMSO-d6, δ in ppm): 2.75 (s, 3H); 4.6 (d, 2H); 5.35 (t, 1H); 7.2 (d, 1H); 7.25 (t, 1H); 7.4 (d, 1H); 7.5 (s, 1H); 7.6 (d, 1H); from 7.65 to 7.75 (m, 2H); 8.45 (s, 1H). M+H=357.

EXAMPLE 11

2-[3-(2-Benzo[d]isoxazol-3-ylimidazo[1,2-a]pyridin-6-yl)phenyl]propan-2-ol (compound 100 of the table)

11.1 [1-(3-Bromophenyl)-1-(methyl)ethyl]oxytrimethylsilane 3.4 g of the compound prepared according to 7.1 in 80 ml of dichloromethane, at 0° C., are placed in a round-bottomed flask. 5.6 ml of triethylamine and 4.5 ml of trimethylsilane chloride are added. The mixture is stirred for one hour at 0° C. and 20 h at ambient temperature. 50 ml of water are added and the mixture is extracted with 30 ml of dichloromethane. The organic phase is washed with 20 ml of a saturated solution of sodium chloride, dried over magnesium sulphate and then concentrated under reduced pressure. The residue is purified by silica gel chromatography, elution being carried out with a heptane/ethyl acetate mixture. 2.5 g of compound are obtained.
¹H NMR (CDCl₃, δ in ppm): 0 (s, 9H); 1.45 (s, 6H); 7.15 to 7.25 (m, 3H); 7.45 (m, 1H).

11.2 5-[3-[1-Methyl-1-(trimethylsilanyloxy)ethyl]phenyl]pyridin-2-ylamine 0.74 g of the compound obtained in 11.1 are placed in 10 ml of tetrahydrofuran and 2 ml of water, and degassed under an argon stream for 10 min. 0.6 g of 5-(4,4,5,5-tetramethyl-1,3,2-dioxaborolan-2-yl)pyridin-2-ylamine, 180 mg of [1,1'-bis(diphenylphosphino)-ferrocene]dichloropalladium and 1.8 g of caesium carbonate are added thereto, and the mixture is heated at 80° C. for 4 hours. After cooling, the reaction mixture is concentrated under reduced pressure. The residue obtained is purified by silica gel chromatography, elution being carried out with a heptane/ethyl acetate mixture. 560 mg of compound are obtained.
¹H NMR (CDCl₃, δ in ppm): 0 (s, 9H); 1.5 (s, 6H); 4.35 (s, 2H); 6.45 (d, 1H); 7.25 (m, 3H); 7.5 (m, 1H); 7.55 (m, 1H); 8.2 (s, 1H). M+H=302.

11.3 N-Methoxy-N-methylbenzo[d]isoxazole-3-carboxamide 1.0 g of benzo[d]isoxazole-3-carboxylic acid, 0.7 g of N,O-dimethylhydroxylamine hydrochloride, 2.3 g of 1-(3-dimethylaminopropyl-3-ethylcarbodiimide) hydrochloride and 1 ml of pyridine in 40 ml of tetrahydrofuran are placed in a round-bottomed flask. The mixture is stirred at ambient temperature for 20 h. The mixture is concentrated and the residue is taken up in 40 ml of ethyl acetate and 20 ml of water. The organic phase is washed with 20 ml of a 1N solution of sodium hydroxide and 20 ml of a saturated solution of sodium chloride, dried over magnesium sulphate and then concentrated under reduced pressure. 1.1 g of compound are obtained.
¹H NMR (CDCl₃, δ in ppm): 3.4 (s, 3H); 3.8 (s, 3H); from 7.25 to 7.55 (m, 3H); 7.95 (d, 1H). M+H=207.

11.4 1-(Benzo[d]isoxazol-3-yl)ethanone 1.1 g of the compound obtained in 11.3 in 50 ml of tetrahydrofuran are placed in a round-bottomed flask, at 0° C. and under argon. 5 ml of methylmagnesium bromide (3M in ethyl ether) are added dropwise. The mixture is stirred for two hours at 0° C. and 20 h at ambient temperature. It is cooled to 0° C. and 25 ml of water and 10 ml of a saturated solution of ammonium chloride are added. The mixture is extracted with 30 ml of ethyl acetate. The organic phase is washed with 40 ml of a saturated 40 ml solution of sodium chloride, dried over magnesium sulphate and then concentrated under reduced pressure. The residue is purified by silica gel chromatography, elution being carried out with a heptane/ethyl acetate mixture. 0.6 g of compound is obtained.
$^1$H NMR (CDCl$_3$, δ in ppm): 2.8 (s, 3H); 7.45 (m, 1H); 7.65 (m, 2H); 8.25 (d, 1H). M+H=162.

11.5 1-(Benzo[d] isoxazol-3-yl)-2-bromoethanone 1.7 g of copper bromide in 75 ml of ethyl acetate are placed in a round-bottomed flask and the mixture is refluxed. 0.6 g of compound obtained in 11.4 is added. The mixture is stirred for 4 hours at reflux. The mixture is filtered through paper and then poured into 100 ml of a 20% solution of sodium thiosulphate. The mixture is extracted with 50 ml of ethyl acetate. The organic phase is washed with 40 ml of a saturated solution of sodium chloride, dried over magnesium sulphate and then concentrated under reduced pressure. 0.7 g of compound is obtained.
$^1$H NMR (CDCl$_3$, δ in ppm): 4.75 (s, 2H); 7.45 (m, 1H); 7.65 (m, 2H); 8.25 (d, 1H).

11.6 2-[3-(2-Benzo[d] isoxazol-3-ylimidazo[1,2-a]pyridin-6-yl)phenyl]propan-2-ol 0.22 g of compound obtained in 11.2 and 0.17 g of compound obtained in 11.5 in 7 ml of ethanol are placed in a round-bottomed flask. 61 mg of sodium hydrogencarbonate are added and the mixture is refluxed for 20 h. After cooling, the reaction mixture is concentrated under reduced pressure. The residue obtained is purified by silica gel chromatography, elution being carried out with a heptane/ethyl acetate mixture. 210 mg of compound are obtained.
$^1$H NMR (DMSO-d6, δ in ppm): 1.55 (s, 6H); 5.15 (s, 1H); 7.45 (t, 1H); 7.55 (m, 3H); 7.75 (m, 2H); 7.85 (m, 3H); 8.55 (d, 1H); 8.75 (s, 1H); 9.05 (s, 1H).

EXAMPLE 12

Process for preparing compounds 102 to 111

12.1
0.495 mmol of palladium acetate and 0.99 mmol of S-Phos are weighed into a 100 ml round-bottomed flask flushed with argon. 55 ml of degassed toluene are added thereto, and the mixture is stirred in an ultrasonic bath until complete dissolution has occurred.
12.2
0.3 mmol of heteroarylboronic acid is weighed into a reaction tube, 0.36 mmol of finely pulverized and dried potassium phosphate, 0.5 ml of degassed anhydrous ethanol and 0.18 mmol of the compound obtained in 7.2, in solution in 2 ml of toluene, are successively added thereto, and the tube is then flushed with argon. 1 ml of the solution prepared in 12.1 is then added. The tube is closed and stirred for 16 h at 75° C. 0.5 ml of solution prepared in 12.2.1 is again added, and the heating is sustained for 10 h. The cooled solution is diluted with 5 ml of ethyl acetate, 100 mg of silica-propanethiol (Biotage Si-Thiol) are added thereto, and the mixture is stirred for 4 h at ambient temperature. The solid is separated by filtration and washed with 2×2 ml of THF. The filtrate is evaporated to dryness and the compound is subjected to purification by chromatography.

EXAMPLE 13

Preparation of compounds 112 to 125

13.1 6-[2-(tert-Butyldimethylsilanyloxymethyl)-3-fluorophenyl]-2-chloroimidazo[1,2-a]pyridine 100 ml of an 85/15 mixture of THF and water are degassed under an argon stream, and then 5.3 g of the compound prepared in 9.2, 6.07 g of 2-chloro-6-(4,4,5,5,-tetramethyl-1,2,3-dioxaborolan-2-yl)imidazo[1,2-a]pyridine obtained as in 4.2, 18.6 g of caesium carbonate and 466 mg of [1,1'-bis(diphenylphosphino)ferrocene]dichloropalladium are added. The mixture is stirred for 2 hours in a thermostated bath at 80° C. After cooling to ambient temperature, the solvents are evaporated off under reduced pressure. The residue is taken up between water and diethyl ether. A solid is removed by filtration. The organic phase, washed twice with a saturated solution of sodium chloride, is then dried over sodium sulphate and concentrated under reduced pressure. The residue obtained is purified by silica gel chromatography, elution being carried out with a dichloromethane/methanol mixture. The solid obtained is triturated with pentane, recovered by filtration, and then oven-dried under reduced pressure. 4.74 g of compound are obtained. $^1$H NMR (CDCl$_3$, δ in ppm): 0 (s, 6H); 0.85 (s, 9H); 4.5 (s, 2H); from 7.05 to 7.1 (m, 2H); from 7.25 to 7.3 (m, 2H); 7.4 (s, 1H); 7.45 (s, 1H); 8.3 (s, 1H). M+H=391.

13.2 Process for preparing compounds 112 to 125

13.2.1
0.3 mmol of heteroarylboronic acid is weighed into a reaction tube, 0.36 mmol of finely pulverized and dried potassium phosphate, 0.5 ml of degassed anhydrous ethanol and 0.18 mmol of the compound obtained in 13.1, in solution in 2 ml of toluene, are successively added thereto, and the tube is then flushed with argon. 1 ml of the solution prepared in 12.1 is then added. The tube is closed and stirred for 16 h at 75° C. 0.5 ml of solution prepared in 12.2.1 is again added and the heating is sustained for 10 h. The cooled solution is diluted with 5 ml of ethyl acetate, 100 mg of silica-propanethiol (Biotage Si-Thiol) are added thereto, and the mixture is stirred for 4 h at ambient temperature. The solid is separated by filtration and washed with 2×2 ml of THF. The filtrate is evaporated to dryness and the residue is used as it is for the subsequent stage.
13.2.2
In a reaction tube, the compound obtained in 13.2.1, 0.36 mmol of caesium fluoride in solution in 3 ml of methanol and 21 µl of acetic acid are mixed. The solution is stirred for 16 hours at ambient temperature, and the solvents are then evaporated off. The residue is purified by HPLC, elution being carried out with an acetonitrile/water mixture.

EXAMPLE 14

Preparation of compounds 126 to 137

14.1 6-[3-(tert-Butyldimethylsilanyloxymethyl)-2,4-difluorophenyl]-2-chloroimidazo[1,2-a]pyridine 100 ml of an 85/15 mixture of THF and water are degassed under an argon stream and then 5.3 g of the compound prepared in 10.2, 6.07 g of 2-chloro-6-(4,4,5,5-tetramethyl-1,2,3-dioxaborolan-2-yl)imidazo[1,2-a]pyridine obtained as in 4.2, 18.6 g of caesium carbonate and 466 mg of [1,1'-bis(diphenylphosphino)ferrocene]dichloropalladium are added. The mixture is stirred for 2 hours in a thermostated bath at 80° C. After cooling to ambient temperature, the solvents are evaporated off under reduced pressure. The residue is taken up between water and diethyl ether. A solid is removed by filtration. The organic phase, washed twice with a saturated solution of sodium chloride, is then dried over sodium sulphate and concentrated under reduced pressure. The residue obtained is purified by silica gel chromatography, elution being carried out with a dichloromethane/methanol mixture. The solid obtained is triturated with pentane, recovered by filtration, and then oven-dried under reduced pressure. 4.74 g of compound are obtained. $^1$H NMR (DMSO-d6, δ in ppm): 0.0 (s, 6H); 0.8 (s, 9H); 4.7 (s, 2H); 7.15 (t, 1H); 7.4 (d, 1H); from 7.5 to 7.6 (m, 2H); 8.0 (s, 1H); 8.65 (s, 1H). M+H=409.

14.2 Preparation of compounds 126 to 137

14.2.1

By carrying out the process as described in 13.2.1, and starting from 0.3 mmol of heteroarylboronic acid and 0.18 mmol of the compound prepared in 14.1, the crude compound, used as it is for the subsequent stage, is obtained.

14.2.2

By carrying out the process as described in 13.2.2, and starting from the compound obtained in 14.2.1, the expected compound is obtained, said compound being purified by HPLC, elution being carried out with an acetonitrile/water mixture.

Table 2 hereinafter illustrates the chemical structures of general formula (I); Table 3 hereinafter illustrates the physicochemical characteristics of some examples of compounds according to the invention. In these tables:

the "Pos." column indicates the position of substitution of the group

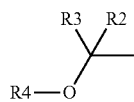

on the phenyl nucleus;

in the "salt/base" column, "-" represents a compound in free base form, whereas "HCl" or "oxalate" represents, respectively, a compound in hydrochloride or oxalate form, and the ratio between parentheses is the (acid:base) ratio;

in Table 3, the "Mp" column indicates the melting points of the products in degrees Celsius (° C.) or, when the products have been isolated in the form of an amorphous solid or of an oil, they are characterized by their mass [M+H];

"Ph" means phenyl; "Cl" means chlorine; "F" means fluorine; "Me" means methyl; "MeO" means methoxy; "(F$_2$CH)O" means difluoromethoxy; "t-Bu" means tent-butyl;

in the R column, the number before the substituent indicates the position of substitution of the R group on the phenyl nucleus;

in the X column, the number before the substituent indicates the position of substitution of the X group on the imidazo[1,2-a]pyridine nucleus;

N.D. means not determined;

TABLE 2

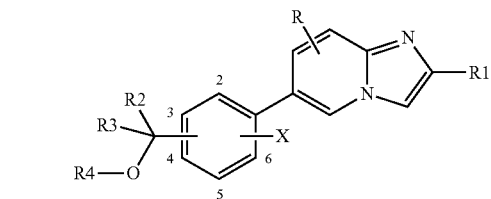

| Ex | R$_1$ | Pos. | R$_2$ | R$_3$ | R$_4$ | X | R | Salt |
|----|-------|------|-------|-------|-------|---|---|------|
| 1 | (5-methylisoxazol-3-yl) | 3 | H | H | H | H | H | — |
| 2 | (pyridin-4-yl) | 3 | H | H | H | H | H | HCl (2:1) |
| 3 | (pyridin-3-yl) | 3 | H | H | t-Bu | H | H | HCl (1:1) |
| 4 | (thiazol-2-yl) | 3 | H | H | H | H | H | — |

TABLE 2-continued

| Ex | R₁ | Pos. | R₂ | R₃ | R₄ | X | R | Salt |
|---|---|---|---|---|---|---|---|---|
| 5 | quinolin-3-yl | 3 | H | H | H | H | H | HCl (2:1) |
| 6 | benzo[1,3]dioxol-5-yl | 3 | H | H | H | H | H | HCl (1:1) |
| 7 | pyridin-3-yl | 3 | H | H | H | H | H | HCl (2:1) |
| 8 | 1H-indol-5-yl | 3 | H | H | H | H | H | HCl (1:1) |
| 9 | 2-oxo-1,2,3,4-tetrahydroquinolin-6-yl | 3 | H | H | H | H | H | HCl (1:1) |
| 10 | 5-bromo-2,3-dihydrobenzofuran-7-yl | 3 | H | H | t-Bu | H | H | — |
| 11 | furan-2-yl | 3 | H | H | H | H | H | HCl (1:1) |
| 12 | furan-3-yl | 2 | H | H | H | H | H | HCl (1:1) |
| 13 | 6-bromo-2,3-dihydrobenzofuran-7-yl | 3 | H | H | H | H | H | — |
| 14 | 5-chlorothiophen-2-yl | 3 | H | H | H | H | H | HCl (1:1) |

TABLE 2-continued

| Ex | R₁ | Pos. | R₂ | R₃ | R₄ | X | R | Salt |
|---|---|---|---|---|---|---|---|---|
| 15 | 5-(2-dimethylamino)pyridyl | 3 | H | H | H | H | H | HCl (2:1) |
| 16 | 4-indolyl (NH) | 3 | H | H | H | H | H | HCl (1:1) |
| 17 | 5-(2-amino)pyridyl | 3 | H | H | H | H | H | HCl (2:1) |
| 18 | 3-indolyl (NH) | 3 | H | H | H | H | H | HCl (1:1) |
| 19 | 3-(2-amino)pyridyl | 3 | H | H | H | H | H | HCl (2:1) |
| 20 | 5-(7-azaindolyl) | 3 | H | H | H | H | H | HCl (2:1) |
| 21 | 5-(3-phenyl)isoxazolyl | 3 | H | H | H | H | H | — |
| 22 | 2-benzofuranyl | 3 | H | H | H | H | H | — |
| 23 | 3-benzofuranyl | 3 | H | H | H | H | H | — |

TABLE 2-continued
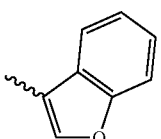
| Ex | R₁ | Pos. | R₂ | R₃ | R₄ | X | R | Salt |
|---|---|---|---|---|---|---|---|---|
| 24 | 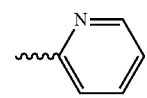 | 4 | H | H | H | H | H | — |
| 25 | 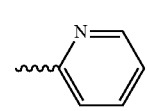 | 3 | H | H | H | H | H | — |
| 26 |  | 4 | H | H | H | H | H | — |
| 27 | 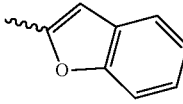 | 3 | H | H | H | H | H | — |
| 28 |  | 3 | H | H | (CH₂)₂OCH₃ | H | H | — |
| 29 |  | 3 | H | H | (CH₂)₂OCH₃ | H | H | oxalate (1:1) |
| 30 | 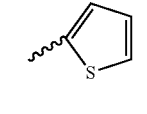 | 3 | H | H | H | H | H | — |
| 31 | 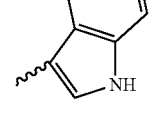 | 3 | H | H | H | H | 3-Me | HCl (1:1) |
| 32 | 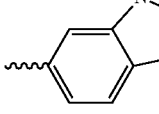 | 3 | H | H | H | H | 3-Me | HCl (1:1) |
| 33 | 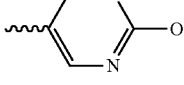 | 3 | H | H | H | H | H | HCl (1:1) |
| 34 |  | 3 | H | H | H | H | H | HCl (1:1) |

TABLE 2-continued

| Ex | R₁ | Pos. | R₂ | R₃ | R₄ | X | R | Salt |
|---|---|---|---|---|---|---|---|---|
| 35 | quinolin-3-yl | 2 | H | H | H | H | H | HCl (1:1) |
| 36 | 2-chloropyridin-5-yl | 3 | H | H | H | H | H | HCl (1:1) |
| 37 | benzothiazol-2-yl | 3 | H | H | H | H | H | HCl (1:1) |
| 38 | benzothiophen-2-yl | 3 | H | H | H | H | H | HCl (1:1) |
| 39 | benzothiophen-5-yl | 3 | H | H | H | H | H | HCl (1:1) |
| 40 | benzothiophen-3-yl | 3 | H | H | H | H | H | HCl (1:1) |
| 41 | 1H-indol-6-yl | 2 | H | H | H | H | H | HCl (1:1) |
| 42 | 2,3-dihydrobenzofuran-5-yl | 3 | H | H | H | H | H | HCl (1:1) |
| 43 | 1H-indol-5-yl | 2 | H | H | H | H | H | HCl (1:1) |
| 44 | benzofuran-5-yl | 3 | H | H | H | H | H | — |

TABLE 2-continued
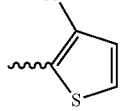
| Ex | R₁ | Pos. | R₂ | R₃ | R₄ | X | R | Salt |
|---|---|---|---|---|---|---|---|---|
| 45 | 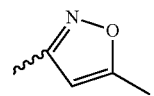 | 3 | H | H | H | H | H | — |
| 46 | 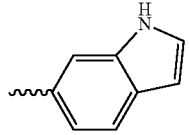 | 2 | H | H | H | 3-F | H | — |
| 47 |  | 3 | Me | Me | H | H | H | — |
| 48 |  | 3 | Me | Me | H | H | 3-Me | — |
| 49 | 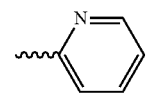 | 3 | Me | Me | H | H | H | — |
| 50 | 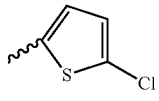 | 3 | Me | Me | H | H | H | — |
| 51 | 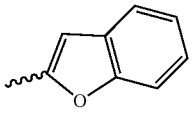 | 3 | Me | Me | H | H | H | — |
| 52 | 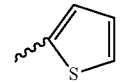 | 3 | Me | Me | H | H | H | — |
| 53 | 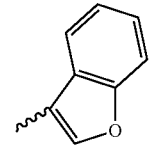 | 3 | Me | Me | H | H | H | — |
| 54 | 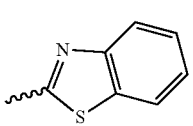 | 3 | Me | Me | H | H | H | — |
| 55 |  | 3 | Me | Me | H | H | H | — |

TABLE 2-continued

| Ex | R₁ | Pos. | R₂ | R₃ | R₄ | X | R | Salt |
|---|---|---|---|---|---|---|---|---|
| 56 | benzothiophen-2-yl | 3 | Me | Me | H | H | H | — |
| 57 | 1-methylbenzimidazol-2-yl | 3 | Me | Me | H | H | H | — |
| 58 | 2,3-dihydrobenzofuran-5-yl | 3 | Me | Me | H | H | H | — |
| 59 | furan-2-yl | 3 | Me | Me | H | H | H | — |
| 60 | benzofuran-5-yl | 3 | Me | Me | H | H | H | — |
| 61 | benzothiophen-5-yl | 3 | Me | Me | H | H | H | — |
| 62 | thiazol-2-yl | 3 | Me | Me | H | H | H | — |
| 63 | 1H-indazol-3-yl | 2 | H | H | H | 3-F | H | HCl (1:1) |
| 64 | 1H-indazol-3-yl | 3 | Me | Me | H | H | H | HCl (1:1) |
| 65 | 1H-indazol-3-yl | 2 | H | H | H | 2,4-diF | H | HCl (1:1) |

TABLE 2-continued
| Ex | R₁ | Pos. | R₂ | R₃ | R₄ | X | R | Salt |
|----|----|----|----|----|----|----|----|----|
| 66 | 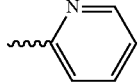 | 2 | H | H | H | 3-F | H | — |
| 67 | 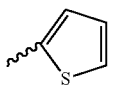 | 2 | H | H | H | 3-F | H | — |
| 68 | 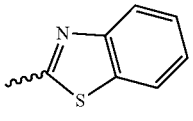 | 2 | H | H | H | 3-F | H | — |
| 69 | 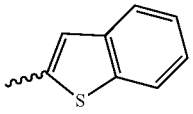 | 2 | H | H | H | 3-F | H | — |
| 70 | 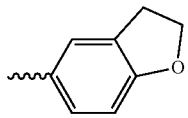 | 2 | H | H | H | 3-F | H | — |
| 71 | 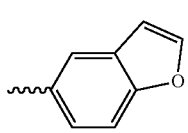 | 2 | H | H | H | 3-F | H | — |
| 72 | 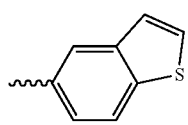 | 2 | H | H | H | 3-F | H | — |
| 73 | 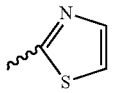 | 2 | H | H | H | 3-F | H | — |
| 74 | 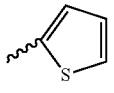 | 2 | H | H | H | 3-F | H | — |
| 75 |  | 3 | H | H | H | 2,4-diF | 3-Me | — |
| 76 | 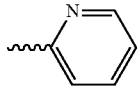 | 3 | H | H | H | 2,4-diF | H | — |
| 77 |  | 3 | H | H | H | 2,4-diF | H | — |

TABLE 2-continued

| Ex | R₁ | Pos. | R₂ | R₃ | R₄ | X | R | Salt |
|---|---|---|---|---|---|---|---|---|
| 78 | 5-chlorothiophen-2-yl | 3 | H | H | H | 2,4-diF | H | — |
| 79 | benzofuran-2-yl | 3 | H | H | H | 2,4-diF | H | — |
| 80 | thiophen-2-yl | 3 | H | H | H | 2,4-diF | H | — |
| 81 | benzofuran-3-yl | 3 | H | H | H | 2,4-diF | H | — |
| 82 | benzothiazol-2-yl | 3 | H | H | H | 2,4-diF | H | — |
| 83 | thiazol-2-yl | 3 | H | H | H | 2,4-diF | H | — |
| 84 | 1-methyl-1H-indol-6-yl | 3 | H | H | Me | H | H | HCl (1:1) |
| 85 | 1H-indol-6-yl | 3 | H | H | Me | H | H | HCl (1:1) |
| 86 | 5-methylisoxazol-3-yl | 3 | Me | Me | H | H | H | — |
| 87 | thiophen-2-yl | 2 | H | H | H | 3-F | 3-Me | — |
| 88 | 5-chlorothiophen-2-yl | 2 | H | H | H | 3-F | H | — |

TABLE 2-continued

| Ex | R₁ | Pos. | R₂ | R₃ | R₄ | X | R | Salt |
|---|---|---|---|---|---|---|---|---|
| 89 | benzofuran-2-yl | 2 | H | H | H | 3-F | H | — |
| 90 | benzofuran-3-yl | 2 | H | H | H | 3-F | H | — |
| 91 | 1-methylbenzimidazol-2-yl | 2 | H | H | H | 3-F | H | — |
| 92 | furan-2-yl | 2 | H | H | H | 3-F | H | — |
| 93 | benzothiophen-2-yl | 3 | H | H | H | 2,4-diF | H | — |
| 94 | 1-methylbenzimidazol-2-yl | 3 | H | H | H | 2,4-diF | H | — |
| 95 | 2,3-dihydrobenzofuran-5-yl | 3 | H | H | H | 2,4-diF | H | — |
| 96 | furan-2-yl | 3 | H | H | H | 2,4-diF | H | — |
| 97 | benzofuran-5-yl | 3 | H | H | H | 2,4-diF | H | — |
| 98 | benzothiophen-5-yl | 3 | H | H | H | 2,4-diF | H | — |

TABLE 2-continued

| Ex | R₁ | Pos. | R₂ | R₃ | R₄ | X | R | Salt |
|---|---|---|---|---|---|---|---|---|
| 99 | 6-indolyl (NH) | 3 | H | H | (CH₂)₂OCH₃ | H | H | — |
| 100 | benzo[d]isoxazol-3-yl | 3 | Me | Me | H | H | H | — |
| 101 | benzo[d]isoxazol-3-yl | 2 | H | H | H | 3-F | H | — |
| 102 | 5-indolyl (NH) | 3 | Me | Me | H | H | H | — |
| 103 | 4-indolyl (NH) | 3 | Me | Me | H | H | H | — |
| 104 | 2-methoxypyridin-3-yl | 3 | Me | Me | H | H | H | — |
| 105 | 4-methylthiophen-3-yl | 3 | Me | Me | H | H | H | — |
| 106 | 1-methylindol-5-yl | 3 | Me | Me | H | H | H | — |
| 107 | quinolin-4-yl | 3 | Me | Me | H | H | H | — |

TABLE 2-continued
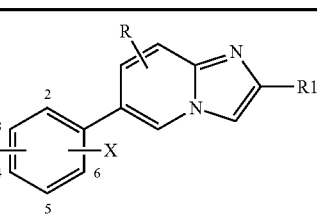
| Ex | R₁ | Pos. | R₂ | R₃ | R₄ | X | R | Salt |
|---|---|---|---|---|---|---|---|---|
| 108 | quinolin-5-yl | 3 | Me | Me | H | H | H | — |
| 109 | 2,6-difluoropyridin-4-yl | 3 | Me | Me | H | H | H | — |
| 110 | 1-(3-methylbutyl)-1H-pyrazol-4-yl | 3 | Me | Me | H | H | H | — |
| 111 | quinolin-3-yl | 3 | Me | Me | H | H | H | — |
| 112 | 1H-indol-5-yl | 2 | H | H | H | 3-F | H | — |
| 113 | 6-methoxypyridin-3-yl | 2 | H | H | H | 3-F | H | — |
| 114 | 3-fluoropyridin-4-yl | 2 | H | H | H | 3-F | H | — |
| 115 | 4-methylthiophen-2-yl | 2 | H | H | H | 3-F | H | — |
| 116 | pyrimidin-5-yl | 2 | H | H | H | 3-F | H | — |

TABLE 2-continued

| Ex | R₁ | Pos. | R₂ | R₃ | R₄ | X | R | Salt |
|---|---|---|---|---|---|---|---|---|
| 117 | 4-(1H-indolyl) | 2 | H | H | H | 3-F | H | — |
| 118 | 6-(1H-indolyl) | 2 | H | H | H | 3-F | H | — |
| 119 | 2-MeO-pyridin-3-yl | 2 | H | H | H | 3-F | H | — |
| 120 | 4-methylthiophen-3-yl | 2 | H | H | H | 3-F | H | — |
| 121 | 1-methyl-1H-indol-5-yl | 2 | H | H | H | 3-F | H | — |
| 122 | quinolin-5-yl | 2 | H | H | H | 3-F | H | — |
| 123 | isoquinolin-5-yl | 2 | H | H | H | 3-F | H | — |
| 124 | 2,6-difluoropyridin-4-yl | 2 | H | H | H | 3-F | H | — |

TABLE 2-continued

| Ex | R₁ | Pos. | R₂ | R₃ | R₄ | X | R | Salt |
|---|---|---|---|---|---|---|---|---|
| 125 | (1-isopentyl-pyrazol-4-yl) | 2 | H | H | H | 3-F | H | — |
| 126 | (1H-indol-5-yl) | 3 | H | H | H | 2,4-diF | H | — |
| 127 | (2-methoxy-pyridin-5-yl) | 3 | H | H | H | 2,4-diF | H | — |
| 128 | (4-methyl-thiophen-2-yl) | 3 | H | H | H | 2,4-diF | H | — |
| 129 | (1H-indol-6-yl) | 3 | H | H | H | 2,4-diF | H | — |
| 130 | (2-methoxy-pyridin-3-yl) | 3 | H | H | H | 2,4-diF | H | — |
| 131 | (3-methyl-thiophen-4-yl) | 3 | H | H | H | 2,4-diF | H | — |
| 132 | (1-methyl-indol-5-yl) | 3 | H | H | H | 2,4-diF | H | — |
| 133 | (quinolin-5-yl) | 3 | H | H | H | 2,4-diF | H | — |

TABLE 2-continued

| Ex | R₁ | Pos. | R₂ | R₃ | R₄ | X | R | Salt |
|---|---|---|---|---|---|---|---|---|
| 134 | isoquinolin-5-yl | 3 | H | H | H | 2,4-diF | H | — |
| 135 | 2,6-difluoropyridin-4-yl | 3 | H | H | H | 2,4-diF | H | — |
| 136 | 1-(3-methylbutyl)-1H-pyrazol-4-yl | 3 | H | H | H | 2,4-diF | H | — |
| 137 | N-tert-butyl-pyridine-3-carboxamid-5-yl | 3 | H | H | H | 2,4-diF | H | — |

TABLE 3

| Ex | Mp or [M + H] | NMR ¹H NMR spectrum (DMSO-d6, δ in ppm) |
|---|---|---|
| 1 | 176-178 | 2.8 (s, 3H); 4.6 (d, 2H); 5.3 (t, 1H); 7.4 (d, 1H); 7.5 (t, 1H); from 7.6 to 7.75 (m, 4H); 8.3 (s, 1H); 8.9 (s, 1H); 9.0 (s, 1H). |
| 2 | 325-330 | 4.6 (s, 2H); 7.4 (d, 1H); 7.5 (m, 1H); 7.65 (d, 1H); 7.75 (s, 1H); 7.85 (m, 2H); 8.55 (d, 2H); 8.85 (d, 2H); 9.05 (m, 2H). |
| 3 | 220-222 | 1.3 (s, 9H); 4.5 (s, 2H); 7.45 (d, 1H); 7.55 (t, 1H); from 7.65 to 7.75 (m, 2H); from 7.85 to 8.0 (m, 2H); 8.05 (d, 1H); from 8.75 to 8.90 (m, 3H); 9.15 (s, 1H); 9.4 (s, 1H). |
| 4 | 201-203 | 4.6 (d, 2H); 5.25 (t, 1H); 7.4 (d, 1H); 7.5 (t, 1H); from 7.55 to 7.75 (m, 4H); 8.1 (s, 1H); 8.35 (s, 1H); 8.95 (s, 1H); 9.25 (s, 1H). |
| 5 | 279-281 | 4.65 (s, 2H); 7.45 (d, 1H); 7.55 (t, 1H); 7.7 (d, 1H); 7.8 (m, 2H); 7.95 (m, 1H); 8.0 (m, 1H); 8.1 (m, 1H); 8.2 (m, 2H); 8.95 (s, 1H); 9.15 (s, 1H); 9.2 (s, 1H); 9.6 (s, 1H). |
| 6 | 264-266 | 4.65 (s, 2H); 6.15 (s, 2H); 7.15 (d, 1H); 7.45 (d, 1H); 7.55 (t, 1H); 7.6 (d, 1H); 7.7 (m, 2H); 7.75 (s, 1H); 8.0 (d, 1H); 8.2 (d, 1H); 8.65 (s, 1H); 9.2 (s, 1H). |
| 7 | 260-265 | 4.65 (s, 2H); 7.45 (d, 1H); 7.55 (t, 1H); 7.65 (d, 1H); 7.75 (s, 1H); from 7.85 to 8.0 (m, 2H); 8.05 (m, 1H); from 8.75 to 8.9 (m, 3H); 9.2 (s, 1H); 9.4 (s, 1H). |
| 8 | 270-272 | 4.65 (s, 2H); 6.6 (s, 1H); 7.45 (d, 1H); from 7.5 to 7.6 (m, 2H); 7.65 (d, 1H); 7.7 (d, 1H); from 7.75 to 7.85 (m, 2H); 8.05 (d, 1H); 8.2 (d, 1H); 8.3 (s, 1H); 8.65 (s, 1H); 9.2 (s, 1H); 11.5 (s, 1H). |

TABLE 3-continued

| Ex | Mp or [M + H] | NMR $^1$H NMR spectrum (DMSO-d6, δ in ppm) |
|---|---|---|
| 9 | 340-345 | 2.55 (m, 2H); 3.0 (t, 2H); 4.65 (s, 2H); 7.05 (d, 1H); 7.45 (d, 1H); 7.55 (t, 1H); 7.65 (d, 1H); 7.75 (s, 1H); from 7.8 to 7.9 (m, 2H); 8.0 (d, 1H); 8.2 (d, 1H); 8.65 (s, 1H); 9.2 (s, 1H). |
| 10 | 277-279 | 1.3 (s, 9H); from 3.25 to 3.35 (m, 2H); 4.5 (s, 2H); 4.9 (t, 2H); from 7.3 to 7.4 (m, 2H); 7.5 (t, 1H); from 7.55 to 7.70 (m, 4H); 8.1 (s, 1H); 8.45 (s, 1H); 9.0 (s, 1H). |
| 11 | 340-345 | 4.65 (s, 2H); 7.35 (d, 1H); 7.45 (d, 1H); 7.55 (t, 1H); 7.65 (d, 1H); 7.75 (s, 1H); 7.85 (d, 1H); from 7.9 to 8.0 (m, 2H); 8.15 (d, 1H); 8.65 (s, 1H); 9.15 (s, 1H); 12.0 (s, 1H). |
| 12 | 205-208 | 4.45 (s, 2H); 7.1 (m, 1H); 7.4 (m, 1H); 7.45 (t, 1H); 7.5 (t, 1H); 7.65 (d, 1H); from 7.9 to 8.0 (m, 3H); 8.45 (s, 1H); 8.55 (s, 1H); 8.95 (s, 1H). |
| 13 | 239-240 | 3.3 (m, 2H); 4.6 (d, 2H); 4.8 (t, 2H); 5.25 (t, 1H); from 7.35 to 7.45 (m, 2H); 7.5 (t, 1H); from 7.55 to 7.7 (m, 4H); 8.1 (s, 1H); 8.45 (s, 1H); 9.0 (s, 1H). |
| 14 | 232-236 | 4.65 (s, 2H); 7.25 (d, 1H); 7.4 (m, 1H); 7.5 (t, 1H); 7.65 (m, 2H); 7.75 (s, 1H); 7.85 (d, 1H); 7.95 (d, 1H); 8.5 (s, 1H); 9.05 (s, 1H). |
| 15 | 280-285 | 3.2 (s, 6H); 4.6 (s, 2H); 7.15 (m, 1H); 7.45 (d, 1H); 7.55 (t, 1H); 7.65 (d, 1H); 7.75 (s, 1H); 8.0 (d, 1H); 8.15 (m, 1H); 8.35 (m, 1H); 8.7 (s, 1H); 8.8 (s, 1H); 9.20 (s, 1H). |
| 16 | 285-290 | 4.65 (s, 2H); 6.9 (m, 1H); 7.35 (t, 1H); 7.45 (d, 1H); 7.55 (t, 1H); from 7.65 to 7.75 (m, 4H); 7.8 (s, 1H); 8.05 (d, 1H); 8.25 (d, 1H); 8.9 (s, 1H); 9.25 (s, 1H); 11.65 (s, 1H). |
| 17 | 375-380 | 4.65 (s, 2H); 7.15 (d, 1H); 7.45 (d, 1H); 7.55 (t, 1H); 7.65 (d, 1H); 7.75 (s, 1H); 7.9 (d, 1H); 8.0 (d, 1H); 8.35 (m, 2H); 8.5 (m, 1H); 8.6 (s, 1H); 8.7 (s, 1H); 9.15 (s, 1H). |
| 18 | 250-254 | 4.65 (s, 2H); 7.1 (m, 1H); 7.25 (m, 2H); from 7.4 to 7.6 (m, 3H); 7.65 (m, 2H); 7.8 (s, 1H); 7.95 (d, 1H); 8.15 (d, 1H); 8.6 (s, 1H); 9.35 (s, 1H); 12.15 (s, 1H). |
| 19 | 340-345 | 4.6 (s, 2H); 7.05 (t, 1H); 7.4 (d, 1H); 7.5 (t, 1H); 7.65 (d, 1H); 7.7 (s, 1H); 7.8 (m, 2H); 8.05 (d, 1H); 8.55 (s, 1H); 8.7 (s, 1H); 9.05 (s, 1H). |
| 20 | 380-385 | 4.65 (s, 2H); 6.65 (d, 1H); 7.45 (d, 1H); 7.55 (t, 1H); 7.65 (s, 1H); 7.7 (d, 1H); 7.8 (s, 1H); 8.05 (d, 1H); 8.3 (d, 1H); 8.7 (s, 1H); 8.8 (s, 1H); 8.95 (s, 1H); 9.3 (s, 1H); 12.05 (s, 1H). |
| 21 | 285-287 | 4.6 (d, 2H); 5.25 (t, 1H); from 7.3 to 7.75 (m, 10H); 7.95 (m, 2H); 8.5 (s, 1H); 8.95 (t, 1H). |
| 22 | 144-146 | 4.6 (d, 2H); 5.25 (t, 1H); from 7.15 to 7.75 (m, 11H); 8.40 (s, 1H); 8.9 (t, 1H). |
| 23 | 150-152 | 4.6 (d, 2H); 5.25 (t, 1H); from 7.25 to 7.75 (m, 9H); 8.2 (m, 1H); 8.45 (s, 1H); 8.5 (s, 1H); 8.9 (t, 1H). |
| 24 | 178-180 | 4.55 (d, 2H); 5.2 (t, 1H); from 7.3 to 7.5 (m, 4H); from 7.55 to 7.75 (m, 5H); 8.2 (m, 1H); 8.45 (s, 1H); 8.5 (s, 1H); 8.9 (m, 1H). |
| 25 | 208-210 | 4.6 (d, 2H); 5.25 (t, 1H); from 7.25 to 7.4 (m, 2H); 7.45 (t, 1H); from 7.5 to 7.7 (m, 4H); 7.85 (t, 1H); 8.1 (d, 1H); 8.5 (s, 1H); 8.6 (m, 1H); 8.9 (m, 1H). |
| 26 | 226-228 | 4.55 (d, 2H); 5.2 (t, 1H); 7.3 (m, 1H); 7.4 (m, 2H); 7.7 (m, 4H); 7.85 (t, 1H); 8.1 (d, 1H); 8.45 (s, 1H); 8.6 (m, 1H); 8.95 (s, 1H). |
| 27 | 162-164 | 4.6 (d, 2H); 5.25 (t, 1H); 7.1 (m, 1H); from 7.25 to 7.65 (m, 8H); 8.25 (s, 1H); 8.85 (t, 1H). |
| 28 | 81-83 | 3.25 (s, 3H); 3.55 (m, 4H); 4.55 (s, 2H); from 7.2 to 7.4 (m, 4H); 7.5 (t, 1H); from 7.68 to 7.75 (m, 6H); 8.4 (s, 1H); 8.95 (t, 1H). |
| 29 | 126-128 | 3.25 (s, 3H); 3.55 (m, 4H); 4.55 (s, 2H); 7.1 (m, 1H); from 7.3 to 7.7 (m, 8H); 8.3 (s, 1H); 8.85 (t, 1H). |
| 30 | 173-175 | 4.6 (d, 2H); 5.2 (t, 1H); 7.3 (d, 1H); 7.45 (t, 1H); from 7.5 to 7.65 (m, 6H); 7.9 (m, 1H); 8.25 (s, 1H); 8.85 (t, 1H). |
| 31 | 279-283 | 2.85 (s, 3H); 4.65 (s, 2H); 7.35 (m, 1H); 7.45 (d, 1H); 7.55 (t, 1H); 7.75 (d, 1H); 8.8 (m, 2H); 8.9 (m, 1H); 8.95 (d, 1H); 8.15 (d, 1H); 8.95 (s, 1H). |
| 32 | 255-258 | 3.75 (s, 3H); 4.65 (s, 2H); 7.2 (t, 1H); 7.3 (t, 1H); 7.45 (d, 1H); from 7.55 to 7.65 (m, 2H); from 7.75 to 7.9 (m, 3H); 7.95 (d, 1H); 8.05 (d, 1H); 8.25 (d, 1H); 9.0 (s, 1H); 11.95 (s, 1H); 14.55 (m, 1H). |
| 33 | 251-254 | 4.65 (s, 2H); 6.55 (s, 1H); 7.45 (d, 1H); 7.55 (m, 2H); 7.65 (d, 1H); 7.7 (d, 1H); 7.75 (m, 2H); 8.0 (d, 1H); 8.1 (s, 1H); 8.25 (d, 1H); 8.7 (s, 1H); 9.25 (s, 1H); 11.6 (s, 1H). |
| 34 | 204-208 | 1.4 (t, 3H); 4.45 (q, 2H); 4.65 (s, 2H); 7.45 (d, 1H); 7.55 (t, 1H); 7.65 (d, 1H); 7.75 (s, 1H); 7.95 (d, 1H); 8.05 (d, 1H); 8.65 (s, 1H); 9.2 (s, 1H); 9.25 (s, 2H). |
| 35 | 290-294 | 4.5 (s, 2H); 7.4 to 7.55 (m, 3H); 7.65 (d, 1H); 7.8 (t, 1H); 7.95 (m, 2H); 8.0 (d, 1H); 8.2 (m, 2H); 9.0 (m, 2H); 9.2 (s, 1H); 9.65 (s, 1H). |
| 36 | 244-248 | 4.6 (s, 2H); 7.4 (d, 1H); 7.5 (t, 1H); 7.65 (d, 1H); 7.75 (s, 1H); 7.9 (d, 1H); 7.95 (d, 1H); 8.05 (m, 1H); 8.15 (s, 1H); 8.55 (d, 1H); 8.85 (s, 1H); 9.05 (s, 1H). |
| 37 | 220-224 | 4.6 (s, 2H); 7.4 (d, 1H); 7.45 to 7.65 (m, 4H); 7.75 (s, 1H); 7.8 (m, 2H); 8.1 (d, 1H); 8.2 (d, 1H); 8.75 (s, 1H); 9.05 (s, 1H). |
| 38 | 261-263 | 4.65 (s, 2H); 7.4 to 7.5 (m, 3H); 7.55 (t, 1H); 7.65 (d, 1H); 7.75 (s, 1H); 7.9 (d, 1H); 7.95 (d, 1H); 8.05 to 8.15 (m, 3H); 8.65 (s, 1H); 9.1 (s, 1H). |

TABLE 3-continued

| Ex | Mp or [M + H] | NMR $^1$H NMR spectrum (DMSO-d6, δ in ppm) |
|---|---|---|
| 39 | 277-279 | 4.6 (s, 2H); 7.4 (d, 1H); 7.45 (t, 1H); 7.55 (d, 1H); 7.65 (d, 1H); 7.7 (s, 1H); 7.85 (d, 1H); 7.95 (m, 2H); 8.15 (d, 1H); 8.2 (d, 1H); 8.5 (s, 1H); 8.7 (s, 1H); 9.15 (s, 1H). |
| 40 | 285-288 | 4.55 (s, 2H); 7.35 (d, 1H); 7.45 (m, 2H); 7.55 (m, 1H); 7.6 (d, 1H); 7.7 (s, 1H); 7.95 (d, 1H); 8.15 (m, 2H); 8.25 (d, 1H); 8.45 (s, 1H); 8.8 (s, 1H); 9.15 (s, 1H). |
| 41 | 310-315 | 4.5 (s, 2H); 6.55 (s, 1H); 7.4 to 7.55 (m, 4H); 7.65 (m, 2H); 7.75 (d, 1H); 7.95 (m, 2H); 8.1 (s, 1H); 8.7 (s, 1H); 8.95 (s, 1H). |
| 42 | 270-271 | 3.35 (t, 2H); from 4.6 to 4.7 (m, 4H); 7.0 (d, 1H); 7.5 (d, 1H); 7.55 (t, 1H); 7.7 (d, 1H); 7.75 (s, 1H); 7.85 (d, 1H); 7.95 (s, 1H); 8.0 (d, 1H); 8.2 (d, 1H); 8.6 (s, 1H); 8.2 (s, 1H). |
| 43 | 310-315 | 4.5 (s, 2H); 6.6 (s, 1H); 7.4 to 7.55 (m, 4H); 7.65 (m, 2H); 7.75 (d, 1H); 8.0 (m, 2H); 8.3 (s, 1H); 8.7 (s, 1H); 8.95 (s, 1H). |
| 44 | 181-183 | 4.65 (d, 2H); 5.3 (t, 1H); 7.1 (s, 1H); 7.4 (t, 1H); 7.55 (t, 1H); 7.65 (m, 1H); 7.75 (m, 4H); 8.0 (d, 1H); 8.1 (s, 1H); 8.35 (s, 1H); 8.5 (s, 1H); 8.95 (s, 1H). |
| 45 | 178-180 | 4.65 (d, 2H); 5.3 (t, 1H); 7.2 (s, 1H); 7.4 (d, 1H); 7.5 (t, 1H); 7.65 (d, 1H); 7.75 (m, 4H); 8.65 (s, 1H); 9.05 (s, 1H). |
| 46 | 277-279 | 2.5 (s, 3H); 4.45 (d, 2H); 5.3 (t, 1H); 6.75 (s, 1H); 7.3 (m, 2H); 7.5 (m, 2H); 7.75 (d, 1H); 8.5 (s, 1H); 8.75 (s, 1H). |
| 47 | 203-204 | 1.55 (s, 6H); 5.1 (s, 1H); 6.45 (s, 1H); from 7.4 to 7.75 (m, 8H).; 7.85 (s, 1H); 8.05 (s, 1H); 8.4 (s, 1H); 8.85 (s, 1H); 11.2 (s, 1H). |
| 48 | [349] | 1.5 (s, 6H); 2.8 (s, 3H); 5.1 (s, 1H); 7.2 (d, 1H); 7.45 (t, 1H); 7.55 (d, 2H); from 7.6 to 7.7 (m, 4H); 7.85 (s, 1H); 8.55 (s, 1H). |
| 49 | [335] | 1.5 (s, 6H); 5.1 (s, 1H); 7.45 (t, 1H); from 7.5 to 7.55 (m, 2H); from 7.6 to 7.7 (m, 4H); 7.8 (s, 1H); 7.95 (d, 1H); 8.3 (s, 1H); 8.9 (s, 1H). |
| 50 | [330] | 1.5 (s, 6H); 5.1 (s, 1H); from 7.3 to 7.35 (m, 1H); 7.45 (t, 1H); 7.5 (d, 1H); 7.55 (d, 1H); 7.65 (d, 1H); 7.7 (d, 1H); 7.8 (s, 1H); 7.9 (t, 1H); 8.15 (d, 1H); 8.55 (s, 1H); 8.65 (d, 1H); 9.0 (s, 1H). |
| 51 | [369] | 1.5 (s, 6H); 5.1 (s, 1H); 7.15 (d, 1H); from 7.4 to 7.45 (m, 2H); from 7.5 to 7.55 (m, 2H); from 7.6 to 7.65 (m, 2H); 7.8 (s, 1H); 8.35 (s, 1H); 8.9 (s, 1H). |
| 52 | [369] | 1.5 (s, 6H); 5.15 (s, 1H); from 7.25 to 7.4 (m, 3H); 7.45 (t, 1H); 7.5 (d, 1H); 7.55 (d, 1H); from 7.65 to 7.75 (m, 4H); 7.85 (s, 1H); 8.45 (s, 1H) 8.95 (s, 1H). |
| 53 | [335] | 1.5 (s, 6H); 5.15 (s, 1H); 7.15 (d, 1H); from 7.5 to 7.6 (m, 4H); from 7.6 to 7.65 (m, 2H); 7.8 (s, 1H); 8.3 (s, 1H); 8.85 (s, 1H). |
| 54 | [369] | 1.5 (s, 6H); 5.1 (s, 1H); from 7.4 to 7.45 (m, 3H); 7.5 (d, 1H); 7.55 (d, 1H); from 7.65 to 7.75 (m, 3H); 7.85 (s, 1H); 8.2 (m, 1H); 8.55 (s, 2H); 8.98 (s, 1H). |
| 55 | [386] | 1.5 (s, 6H); 5.15 (s, 1H); 7.45 (t, 2H); from 7.5 to 7.6 (m, 3H); 7.65 (d, 1H); 7.7 (d, 1H); 7.85 (s, 1H); 8.05 (d, 1H); 8.15 (d, 1H); 8.7 (s, 1H); 9.0 (s, 1H). |
| 56 | [385] | 1.5 (s, 6H); 5.15 (s, 1H); from 7.35 to 7.45 (m, 3H); 7.5 (d, 1H); 7.55 (d, 1H); 7.65 (d, 1H); 7.7 (d, 1H); 7.8 (s, 1H); from 7.85 to 7.9 (m, 2H); 8.0 (d, 1H); 8.55 (s, 1H); 8.9 (s, 1H). |
| 57 | [383] | 1.5 (s, 6H); 4.35 (s, 3H); 5.15 (s, 1H); from 7.25 to 7.35 (m, 2H); 7.45 (t, 1H); 7.5 (d, 1H); 7.6 (d, 1H); from 7.65 to 7.75 (m, 3H); 7.8 (d, 1H); 7.85 (s, 1H); 8.7 (s, 1H); 9.05 (s, 1H). |
| 58 | [371] | 1.5 (s, 6H); from 3.2 to 3.3 (m, 2H); from 4.55 to 4.6 (m, 2H); 5.1 (s, 1H); 6.85 (d, 1H); from 7.4 to 7.55 (m, 4H); 7.6 (d, 1H); 7.7 (d, 1H); 7.8 (s, 1H); 7.85 (s, 1H); 8.3 (s, 1H); 8.85 (s, 1H). |
| 59 | [319] | 1.5 (s, 6H); 5.15 (s, 1H); 6.6 (d, 1H); 6.85 (d, 1H); 7.4 (t, 1H); from 7.45 to 7.55 (m, 2H); 7.65 (m, 2H); 7.75 (s, 1H); 7.8 (s, 1H); 8.2 (s, 1H); 8.9 (s, 1H). |
| 60 | [369] | 1.5 (s, 6H); 5.15 (s, 1H); 7.05 (s, 1H); 7.45 (t, 1H);. 7.5 (d, 1H); 7.55 (d, 1H); 7.6 (d, 1H); from 7.6 to 7.7 (d, 2H); 7.8 (s, 1H); 7.95 (d, 1H); 8.0 (d, 1H); 8.3 (s, 1H); 8.45 (s, 1H); 8.9 (s, 1H). |
| 61 | [385] | 1.5 (s, 6H); 5.15 (s, 1H); from 7.45 to 7.5 (m, 2H); from 7.55 to 7.6 (m, 2H); 7.65 (d, 1H); 7.7 (d, 1H); from 7.8 to 7.85 (m, 2H); 8.0 (d, 1H); 8.05 (d, 1H); 8.5 (s, 1H); 8.55 (s, 1H); 8.9 (s, 1H). |
| 62 | [336] | 1.5 (s, 6H); 5.15 (s, 1H); 7.45 (t, 1H); from 7.45 to 7.55 (m, 2H); from 7.65 to 7.7 (m, 2H); 7.75 (d, 1H); 7.8 (s, 1H); 7.9 (sd, 1H); 8.5 (s, 1H); 8.95 (s, 1H). |
| 63 | 330-335 | 4.5 (s, 2H); 7.4 (m, 3H); 7.55 (m, 2H); 7.75 (d, 1H); 8.05 (m, 2H); 8.3 (d, 1H); 9.0 (s, 1H); 9.15 (s, 1H); 14.0 (s, 1H). |
| 64 | 190-195 | 1.55 (s, 6H); 7.4 (t, 1H); 7.6 (m, 4H); 7.75 (d, 1H); 7.9 (s, 1H); 8.0 (d, 1H); 8.25 (m, 2H); 9.05 (s, 1H); 9.2 (s, 1H); 14.0 (s, 1H) |
| 65 | 350-355 | 4.65 (s, 2H); 7.35 (m, 2H); 7.55 (s, 1H); 7.75 (m, 2H); 8.05 (m, 2H); 8.25 (d, 1H); 9.05 (s, 1H); 9.1 (s, 1H); 13.9 (s, 1H). |
| 66 | [325] | 4.45 (d, 2H); 5.3 (t, 1H); from 7.25 to 7.3 (m, 2H); from 7.4 to 7.5 (m, 2H); from 7.5 to 7.55 (m, 3H); 7.95 (s, 1H); 8.3 (s, 1H); 8.65 (s, 1H). |
| 67 | [320] | 4.45 (s, 2H); 5.25 (s, 1H); from 7.25 to 7.35 (m, 3H); 7.45 (m, 2H); 7.7 (d, 1H); 7.9 (t, 1H); 8.25 (d, 1H); 8.5 (s, 1H); 8.65 (s, 1H); 8.75 (s, 1H). |
| 68 | [325] | 4.45 (d, 2H); 5.3 (t, 1H); 7.15 (m, 1H); from 7.2 to 7.3 (m, 2H); from 7.4 to 7.5 (m, 2H); from 7.5 to 7.6 (m, 2H); 7.65 (d, 1H); 8.3 (s, 1H); 8.65 (s, 1H). |

TABLE 3-continued

| Ex | Mp or [M + H] | NMR $^1$H NMR spectrum (DMSO-d6, δ in ppm) |
|---|---|---|
| 69 | [376] | 4.45 (d, 2H); 5.3 (t, 1H); from 7.25 to 7.35 (m, 2H); from 7.45 to 7.5 (m, 2H); from 7.5 to 7.6 (m, 2H); 7.75 (d, 1H); 8.05 (d, 1H); 8.15 (d, 1H); 8.7 (s, 1H); 8.75 (s, 1H). |
| 70 | [375] | 4.45 (d, 2H); 5.3 (t, 1H); from 7.25 to 7.4 (m, 4H); from 7.45 to 7.5 (m, 2H); 7.7 (d, 1H); 7.85 (d, 1H); 7.9 (s, 1H); 8.0 (d, 1H); 8.5 (s, 1H); 8.7 (s, 1H). |
| 71 | [361] | 3.25 (t, 2H); 4.45 (d, 2H); 4.55 (t, 2H); 5.3 (t, 1H); 6.85 (d, 1H); 7.25 (m, 2H); 7.4 (d, 1H); 7.45 (m, 1H); 7.6 (d, 1H); 7.75 (d, 1H); 7.85 (s, 1H); 8.3 (s, 1H); 8.65 (s, 1H). |
| 72 | [359] | 4.45 (d, 2H); 5.3 (t, 1H); 7.05 (s, 1H); 7.3 (m, 2H); from 7.4 to 7.5 (m, 2H); 7.65 (d, 2H); 7.95 (d, 1H); 8.05 (s, 1H); 8.3 (s, 1H); 8.45 (s, 1H); 8.65 (s, 1H). |
| 73 | [375] | 4.45 (d, 2H); 5.35 (t, 1H); 7.3 (m, 2H); from 7.4 to 7.5 (m, 2H); 7.55 (d, 1H); 7.65 (d, 1H); 7.8 (d, 1H); 8.0 (d, 1H); 8.05 (d, 1H); 8.5 (s, 1H); 8.55 (s, 1H); 8.7 (s, 1H). |
| 74 | [326] | 4.45 (d, 2H); 5.3 (t, 1H); from 7.25 to 7.35 (m, 2H); from 7.45 to 7.55 (m, 2H); 7.7 (d, 1H); 7.75 (s, 1H); 7.95 (s, 1H); 8.5 (s, 1H); 8.75 (s, 1H). |
| 75 | [357] | 2.75 (s, 3H); 4.6 (d, 2H); 5.35 (t, 1H); 7.2 (d, 1H); 7.25 (t, 1H); 7.4 (d, 1H); 7.5 (s, 1H); 7.6 (d, 1H); from 7.65 to 7.75 (m, 2H); 8.45 (s, 1H). |
| 76 | [343] | 4.6 (d, 2H); 5.35 (t, 1H); 7.25 (t, 1H); 7.4 (d, 1H); from 7.55 to 7.65 (m, 4H); 7.95 (s, 1H); 8.35 (s, 1H); 8.75 (s, 1H). |
| 77 | [338] | 4.6 (s, 2H); 5.35 (s, 1H); 7.25 (t, 1H); 7.35 (m, 1H); 7.45 (d, 1H); 7.6 (m, 1H); 7.75 (d, 1H); 7.9 (t, 1H); 8.15 (d, 1H); 8.55 (s, 1H); 8.65 (d, 1H); 8.85 (s, 1H). |
| 78 | [377] | 4.6 (d, 2H); 5.35 (t, 1H); 7.15 (s, 1H); 7.25 (t, 1H); from 7.4 to 7.45 (m, 2H); from 7.55 to 7.65 (m, 2H); 8.35 (s, 1H); 8.75 (s, 1H). |
| 79 | [377] | 4.6 (d, 2H); 5.35 (t, 1H); from 7.2 to 7.3 (m, 2H); 7.35 (m, 2H); 7.5 (d, 1H); from 7.6 to 7.75 (m, 4H); 8.5 (s, 1H); 8.85 (s, 1H). |
| 80 | [343] | 4.6 (s, 2H); 5.35 (s, 1H); 7.15 (d, 1H); 7.35 (t, 1H); 7.45 (d, 1H); 7.55 (m, 2H); from 7.6 to 7.7 (m, 2H); 8.35 (s, 1H); 8.75 (s, 1H). |
| 81 | [377] | 4.6 (d, 2H); 5.35 (t, 1H); 7.25 (t, 1H); from 7.4 to 7.5 (m, 3H); from 7.6 to 7.75 (m, 3H); 8.25 (m, 1H); 8.55 (d, 2H); 8.8 (s, 1H). |
| 82 | [394] | 4.6 (d, 2H); 5.35 (t, 1H); 7.25 (t, 1H); 7.45 (t, 1H); 7.55 (m, 2H); 7.65 (m, 1H); 7.8 (d, 1H); 8.05 (d, 1H); 8.15 (d, 1H); 8.75 (s, 1H); 8.9 (s, 1H). |
| 83 | [344] | 4.6 (s, 2H); 5.35 (s, 1H); from 7.25 to 7.3 (m, 2H); from 7.4 to 7.5 (m, 2H); from 7.5 to 7.55 (m, 3H); 7.95 (s, 1H); 8.3 (s, 1H); 8.65 (s, 1H). |
| 84 | 247-252 | 3.4 (s, 3H); 3.9 (s, 3H); 4.55 (s, 2H); 6.55 (s, 1H); from 7.45 to 7.8 (m, 7H); 8.0 (d, 1H); 8.25 (m, 2H); 8.7 (s, 1H); 9.25 (s, 1H). |
| 85 | 88-92 | 3.35 (s, 3H); 4.55 (s, 2H); 6.55 (s, 1H); 7.45 (d, 1H); from 7.55 to 7.65 (m, 3H); 7.75 (m, 3H); 8.0 (d, 1H); 8.1 (s, 1H); 8.25 (d, 1H); 8.7 (s, 1H); 9.25 (s, 1H); 11.6 (s, 1H). |
| 86 | 205-208 | 1.5 (s, 6H); 2.5 (s, 3H); 5.1 (s, 1H); 6.7 (s, 1H); 7.45 (m, 1H); 7.55 (m, 2H); 7.7 (m, 2H); 7.8 (s, 1H); 8.45 (s, 1H); 8.95 (s, 1H). |
| 87 | [339] | 2.70 (s, 3H); 4.45 (d, 2H); 5.35 (t, 1H); 7.20 (m, 1H); 7.32 (m, 2H); 7.47 (m, 3H); 7.58 (m, 1H); 7.64 (d, 1H); 8.50 (s, 1H). |
| 88 | [359] | 4.43 (d, 2H); 5.30 (t, 1H); 7.18 (s, 1H); 7.30 (m, 2H); 7.46 (m, 3H); 7.65 (d, 1H); 8.39 (s, 1H); 8.68 (s, 1H). |
| 89 | [359] | 4.45 (d, 2H); 5.30 (t, 1H); 7.32 (m, 5H); 7.48 (m, 2H); 7.65 (d, 1H); 7.70 (m, 2H); 8.47 (s, 1H); 8.72 (s, 1H). |
| 90 | [359] | 4.45 (d, 2H); 5.32 (t, 1H); 7.30 (m, 2H); 7.41 (m, 2H); 7.48 (m, 2H); 7.70 (m, 2H); 8.25 (m, 1H); 8.54 (m, 2H); 8.72 (s, 1H). |
| 91 | [373] | 4.35 (s, 3H); 4.47 (d, 2H); 5.31 (t, 1H); 7.28 (m, 4H); 7.49 (m, 1H); 7.55 (d, 1H); 7.65 (dd 2H); 7.78 (d, 1H); 8.66 (s, 1H); 8.78 (s, 1H). |
| 92 | [309] | 4.45 (d, 2H); 5.30 (t, 1H); 6.63 (s, 1H); 6.88 (s, 1H); 7.29 (m, 2H); 7.47 (m, 2H); 7.62 (d, 1H); 7.78 (s, 1H); 8.23 (s, 1H); 8.69 (s, 1H). |
| 93 | [393] | 4.61 (d, 2H); 5.34 (t, 1H); 7.25 (t, 1H); 7.40 (m, 2H); 7.48 (d, 1H); 7.65 (m, 1H); 7.72 (d, 1H); 7.88 (d, 1H); 7.91 (s, 1H); 8.00 (d, 1H); 8.52 (s, 1H); 8.81 (s, 1H). |
| 94 | [391] | 4.35 (s, 3H); 4.62 (d, 2H); 5.32 (t, 1H); 7.29 (m, 3H); 7.53 (d, 1H); 7.67 (m, 3H); 7.82 (d, 1H); 8.70 (s, 1H); 8.94 (s, 1H). |
| 95 | [379] | 3.25 (t, 2H); 4.58 (m, 4H); 5.34 (t, 1H); 6.83 (d, 1H); 7.25 (t, 1H); 7.40 (d, 1H); 7.62 (m, 2H); 7.74 (d, 1H); 7.86 (s, 1H); 8.30 (s, 1H); 8.74 (s, 1H). |
| 96 | [327] | 4.60 (d, 2H); 5.33 (t, 1H); 6.62 (s, 1H); 6.88 (s, 1H); 7.25 (t, 1H); 7.42 (d, 1H); 7.63 (m, 2H); 7.79 (s, 1H); 8.24 (s, 1H); 8.80 (s, 1H). |
| 97 | [377] | 4.62 (d, 2H); 5.35 (t, 1H); 7.05 (s, 1H); 7.25 (t, 1H); 7.41 (d, 1H); 7.68 (m, 3H); 7.97 (d, 1H); 8.05 (s, 1H); 8.30 (s, 1H); 8.47 (s, 1H); 8.78 (s, 1H). |
| 98 | [393] | 4.61 (d, 2H); 5.34 (t, 1H); 7.25 (t, 1H); 7.43 (d, 1H); 7.57 (d, 1H); 7.64 (m, 1H); 7.72 (d, 1H); 7.81 (d, 1H); 7.99 (d, 1H); 8.08 (d, 1H); 8.52 (d, 2H); 8.79 (s, 1H). |
| 99 | 67-70 | 3.3 (s, 3H); 3.55 (m, 2H); 3.65 (m, 2H); 4.6 (s, 2H); 6.45 (m, 1H); 7.4 (m, 2H); 7.5 (t, 1H); from 7.55 to 7.7 (m, 6H); 8.05 (s, 1H); 8.35 (s, 1H); 8.9 (s, 1H); 11.15 (s, 1H). |
| 100 | 206-210 | 1.55 (s, 6H); 5.15 (s, 1H); 7.45 (t, 1H); 7.55 (m, 3H); 7.75 (m, 2H); 7.85 (m, 3H); 8.55 (d, 1H); 8.75 (s, 1H); 9.05 (s, 1H). |

TABLE 3-continued

| Ex | Mp or [M + H] | NMR ¹H NMR spectrum (DMSO-d6, δ in ppm) |
|---|---|---|
| 101 | 275-277 | 4.45 (d, 2H); 5.35 (t, 1H); 7.35 (m, 2H); 7.45 to 7.6 (m, 3H); 7.75 to 7.9 (m, 3H); 8.55 (d, 1H); 8.8 (m, 2H). |
| 102 | [368] | 1.5 (s, 6H); 5.15 (s, 1H); 6.5 (m, 1H); 7.5 (m, 7H); 7.72 (d, 1H); 7.8 (s, 1H); 8.19 (s, 1H); 8.32 (s, 1H); 8.85 (s, 1H); 11.2 (s, 1H). |
| 103 | [368] | 1.5 (s, 6H); 5.15 (s, 1H); 6.4 (m, 1H); 7.0 (m, 1H); 7.05 (m, 2H); 7.2 (m, 1H); 7.35 (m, 1H); 7.5 (m, 3H); 7.75 (m, 1H); 7.85 (s, 1H); 8.6 (s, 1H); 8.95 (s, 1H); 11.0 (s, 1H). |
| 104 | [360] | 1.5 (s, 6H), 4.1 (s, 3H), 5.1 (s, 1H), 7.15 (m, 1 H), 7.45 (m, 1H), 7.55 (m, 2H), 7.7 (s, 2H), 7.8 (s, 1H), 8.2 (d, 1H), 8.55 (s, 1H), 8.6 (d, 1H), 9.0 (s, 1H) |
| 105 | [346] | 1.5 (s, 6H), 2.5 (s, 3H), 5.15 (s, 1H), 7.3 (m, 1H), 7.45 (m, 1H), 7.5 (m, 2H), 7.65 (m, 2H), 7.8 (s, 1H), 7.9 (d, 1H), 8.25 (s, 1H), 8.9 (s, 1H) |
| 106 | [382] | 1.5 (s, 6H), 3.85 (s, 3H), 5.1 (s, 1H), 6.5 (d, 1H), 7.35 (d, 1H), 7.45 (m, 1H), 7.55 (m, 3H), 7.65 (m, 2H), 7.8 (m, 2H), 8.2 (s, 1H), 8.4 (s, 1H), 8.9 (s, 1H) |
| 107 | [380] | 1.5 (s, 6H); 5.15 (m, 1H); 7.45 (m, 1H); 7.6 (m, 2H); 7.8 (m, 4H); 8.0 (d, 1H); 8.2 (d, 1H); 8.5 (s, 1H); 8.95 (m, 1H); 9.0 (m, 1H); 9.05 (s, 1H); 9.35 (d, 1H). |
| 108 | [380] | 1.5 (s, 6H); 5.15 (s, 1H); 7.6 (m, 3H); 7.85 (m, 4H); 8.2 (m, 2H); 8.5 (s, 1H); 8.6 (d, 1H); 8.8 (d, 1H); 9.0 (s, 1H); 9.4 (s, 1H). |
| 109 | [357] | 1.5 (s, 6H), 5.1 (s, 1H), 7.45 (t, 1H), 7.55 (d, 1H), 7.6 (d, 1H), 7.7 (s, 2H), 7.75 (m, 1H), 7.8 (m, 2H), 8.75 (s, 1H), 8.95 (s, 1H) |
| 110 | [366] | 0.95 (d, 6H), 1.5 (m, 7H), 1.7 (m, 2H), 4.2 (t, 2H), 5.1 (s, 1H), 7.45 (m, 1H), 7.55 (m, 2H), 7.65 (m, 2H), 7.8 (s, 1H), 7.9 (s, 1H), 8.15 (s, 1H), 8.25 (s, 1H), 8.9 (s, 1H) |
| 111 | [380] | 1.5 (s, 6H), 5.15 (s, 1H), 7.65 (m, 8H), 8.05 (m, 1H), 8.1 (m, 1H), 8.7 (s, 1H), 8.9 (m, 1H), 8.95 (s, 1H), 9.95 (s, 1H) |
| 112 | [358] | 4.45 (d, 2H); 5.30 (t, 1H); 6.5 (s, 1H); 7.3 (m, 2H); 7.4 (m, 1H); 7.45 (m, 3H); 7.65 (d, 1H); 7.75 (d, 1H); 8.2 (s, 1H); 8.4 (s, 1H); 8.7 (s, 1H); 11.2 (s, 1H). |
| 113 | [350] | 3.9 (s, 3H); 4.4 (s, 2H); 5.35 (s, 1H); 6.9 (d, 1H,);7.4 (m, 3H) 7.65 (d, 2H); 8.25 (d, 1H); 8.45 (s 1H); 8.70 (s, 1H); 8.75 (s, 1H). |
| 114 | [338] | 4.45 (m, 2H); 5.3 (m, 1H); 7.3 (m, 2H); 7.5 (m, 2H); 7.75 (d, 1H); 8.25 (m, 1H); 8.55 (d, 1H); 8.6 (d, 1H); 8.7 (m, 1H); 8.75 (m, 1H). |
| 115 | [339] | 2.25 (s, 3H); 4.44 (s, 2H); 5.3 (s, 1H); 7.1 (s, 1H); 7.3 (m, 2H); 7.45 (m, 3H); 7.6 (d, 1H); 8.3 (s, 1H); 8.65 (s, 1H). |
| 116 | [321] | 4.45 (d, 2H); 5.35 (t, 1H); 7.3 (m, 2H); 7.5 (m, 2H); 7.75 (d, 1H); 8.7 (s, 1H); 8.78 (s, 1H); 9.18 (s, 1H); 9.4 (s, 2H). |
| 117 | [358] | 4.45 (m, 2H); 5.25 (m, 1H); 7.05 (s, 1H); 7.2 (m, 1H); 7.25 (m, 2H); 7.45 (m, 4H); 7.75 (m, 2H); 8.6 (s, 1H); 8.75 (s, 1H); 11.0 (s, 1H). |
| 118 | [358] | 4.45 (m, 2H); 5.3 (m, 1H); 6.45 (s, 1H); 7.3 (m, 2H); 7.45 (m, 4H); 7.6 (m, 2H); 8.05 (s, 1H); 8.4 (s, 1H); 8.7 (s, 1H); 11.2 (s, 1H). |
| 119 | [350] | 4.1 (s, 3H); 4.45 (m, 2H); 5.3 (m, 1H); 7.2 (m, 1H); 7.3 (d, 2H); 7.5 (m, 2H); 7.7 (d, 1H); 8.2 (m, 1H); 8.5 (s, 1H); 8.6 (d, 1H); 8.75 (s, 1H). |
| 120 | [339] | 3.15 (s, 3H); 4.45 (m, 2H); 5.3 (m, 1H); 7.3 (m, 3H); 7.45 (m, 2H); 7.65 (d, 1H); 7.9 (d, 1H); 8.25 (s, 1H); 8.7 (s, 1H). |
| 121 | [372] | 3.8 (s, 3H); 4.45 (m, 2H); 5.35 (m, 1H); 6.55 (d, 1H); 7.3 (d, 2H); 7.4 (d, 1H); 7.5 (m, 1H); 7.6 (m, 2H); 7.75 (d, 1H); 7.8 (d, 1H); 8.2 (s, 1H); 8.5 (s, 1H); 8.75 (s, 1H). |
| 122 | [370] | 4.45 (m, 2H); 5.3 (m, 1H); 7.3 (m, 2H); 7.5 (m, 2H); 7.65 (m, 1H); 7.75 (d, 1H); 7.85 (m, 1H); 8.0 (d, 1H); 8.1 (m, 1H); 8.45 (s, 1H); 8.8 (s, 1H); 8.95 (m, 1H); 9.35 (m, 1H). |
| 123 | [370] | 4.45 (s, 2H); 5.3 (m, 1H); 7.3 (m, 2H); 7.55 (m, 2H); 7.9 (m, 3H); 8.25 (m, 2H); 8.55 (s, 1H); 8.6 (d, 1H); 8.85 (d, 1H); 9.45 (s, 1H). |
| 124 | [356] | 4.45 (m, 2H); 5.35 (m, 1H); 7.3 (d, 2H); 7.5 (m, 2H); 7.7 (m, 3H); 8.75 (s, 1H); 8.85 (s, 1H). |
| 125 | [379] | 0.9 (d, 6H); 1.5 (m, 1H); 1.7 (m, 2H); 4.2 (t, 2H); 4.4 (s, 2H); 5.25 (s, 1H); 7.25 (m, 3H); 7.5 (m, 3H); 7.6 (d, 1H); 8.1 (s, 1H); 8.65 (s, 1H). |
| 126 | [376] | 4.6 (s, 2H); 5.35 (s, 1H); 6.5 (s, 1H); 7.25 (t, 1H); 7.4 (s, 1H); 7.45 (m, 2H); 7.65 (m, 3H); 8.2 (s, 1H); 8.4 (s, 1H); 8.75 (s, 1H); 11.2 (s, 1H). |
| 127 | [368] | 3.9 (s, 3H); 4.6 (d, 2H); 5.3 (t, 1H); 6.9 (d, 1H); 7.2 (t, 1H); 7.4 (m, 1H); 7.6 (m, 1H); 7.7 (d, 1H); 8.25 (d, 1H); 8.4 (s, 1H); 8.75 (d, 2H). |
| 128 | [389] | 2.25 (s, 3H); 4.6 (s, 2H); 5.3 (s, 1H); 7.1 (s, 1H); 7.25 (t, 1H); 7.4 (m, 2H); 7.6 (m, 2H); 8.3 (s, 1H); 8.7 (s, 1H). |
| 129 | [376] | 4.6 (d, 2H); 5.35 (t, 1H); 6.45 (s, 1H); 7.25 (m, 1H); 7.45 (m, 2H); 7.65 (m, 4H); 8.05 (s, 1H); 8.45 (s, 1H); 8.75 (s, 1H); 11.2 (s, 1H). |
| 130 | [368] | 4.1 (s, 3H); 4.6 (d, 2H); 5.3 (t, 1H); 7.15 (m, 1H); 7.25 (t, 1H); 7.45 (m, 1H); 7.65 (m, 2H); 8.15 (m, 1H); 8.55 (s, 1H); 8.6 (d, 1H); 8.85 (s, 1H). |
| 131 | [357] | 2.45 (s, 3H); 4.6 (s, 2H); 5.35 (s, 1H); 7.25 (m, 2H); 7.4 (m, 1H); 7.65 (m, 2H); 7.9 (d, 1H); 8.25 (s, 1H); 8.8 (s, 1H). |
| 132 | [390] | 3.85 (s, 3H); 4.6 (d, 2H); 5.35 (t, 1H); 6.5 (d, 1H); 7.25 (t, 1H); 7.45 (d, 1H); 7.5 (m, 2H); 7.65 (m, 2H); 7.8 (d, 1H); 8.2 (s, 1H); 8.45 (s, 1H); 8.8 (s, 1H). |
| 133 | [388] | 4.6 (d, 2H); 5.35 (t, 1H); 7.25 (t, 1H); 7.5 (d, 1H); 7.65 (m, 2H); 7.85 (m, 2H); 8.0 (d, 1H); 8.1 (m, 1H); 8.5 (s, 1H); 8.85 (s, 1H); 9.0 (m, 1H); 9.35 (d, 1H). |

TABLE 3-continued

| Ex | Mp or [M + H] | NMR $^1$H NMR spectrum (DMSO-d6, δ in ppm) |
|---|---|---|
| 134 | [388] | 4.6 (s, 2H); 5.35 (s, 1H); 7.25 (m, 1H); 7.7 (m, 4H); 8.2 (m, 2H); 8.55 (s, 1H); 8.6 (d, 1H); 8.8 (d 1H); 8.85 (s, 1H); 9.45 (s, 1H) |
| 135 | [374] | 455 (s, 2H); 5.35 (s, 1H); 7.25 (t, 1H); 7.50 (d, 1H); 7.65 (m, 1H); 7.7 (s, 2H); 7.75 (d, 1H); 8.80 (d, 1H); 8.85 (s, 1H) |
| 136 | [397] | 0.9 (d, 6H); 1.5 (m, 1H); 1.7 (m, 2H); 4.15 (t, 2H); 4.6 (s, 2H); 5.35 (s, 1H); 7.25 (t, 1H); 7.45 (m, 1H); 7.55 (m, 2H); 7.9 (s, 1H); 8.15 (s, 1H); 8.25 (s, 1H); 8.8 (s, 1H); |
| 137 | [437] | 1.4 (s, 9H); 4.6 (m, 2H); 5.35 (m, 1H); 7.75 (d, 1H); 8.15 (s, 1H); 8.2 (s, 1H); 8.55 (m, 1H); 8.65 (m, 1H); 8.8 (m, 1H); 8.9 (m, 1H); 9.0 (s, 1H); 9.15 (s, 1H); 9.3 (s, 1H); |

The compounds according to the invention were the subject of pharmacological tests for determining their modulatory effect on NOT.

Evaluation of the In Vitro Activity on N2A Cells

The activity of the compounds according to the invention was evaluated on a cell line (N2A) endogenously expressing the mouse Nurr1 receptor and stably transfected with the NOT binding response element (NBRE) coupled to the luciferase reporter gene. The $EC_{50}$ values are between 0.01 and 10 μM. The tests were carried out according to the procedure described below.

The Neuro-2A cell line comes from a standard commercial source (ATCC). The Neuro-2A clone was obtained from a spontaneous tumour originating from a mouse A albino strain, by R. J Klebe et el. This Neuro-2A line is then stably transfected with 8NBRE-luciferase. The N2A-8NBRE cells are cultured to confluence in 75 cm$^2$ culture flasks containing DMEM supplemented with 10% of foetal calf serum, 4.5 g/l of glucose and 0.4 mg/ml of geneticin. After one week of culture, the cells are recovered with 0.25% trypsin for 30 seconds, and then resuspended in DMEM without phenol red, containing 4.5 g/l of glucose and 10% of Hyclone defatted serum, and deposited in white, transparent-bottom 96-well plates. The cells are deposited at a rate of 60 000 per well in 75 μl for 24 hours before the addition of the products. The products are applied in 25 μl and incubated for a further 24 hours. On the day of the measurement, an equivalent volume (100 μl) of Steadylite is added to each well, followed by a waiting period of 30 minutes in order to obtain complete lysis of the cells and maximum production of the signal. The plates are then measured in a microplate luminescence counter after having been sealed with an adhesive film. The products are prepared in the form of a stock solution at $10^{-2}$ M, and then diluted in 100% of DMSO. Each product concentration is diluted beforehand in culture medium before incubation with the cells thus containing a final concentration of 0.625% of DMSO.

For example, compounds No. 6, 7, 24, 50, 68, 79 and 86 showed an $EC_{50}$ of 0.9, 1.6, 50, 202, 20, 5 and 71 nM, respectively. It therefore appears that the compounds according to the invention have a NOT-modulating effect.

The compounds according to the invention can therefore be used for the preparation of medicaments for their therapeutic use in the treatment or prevention of diseases involving NOT receptors.

Thus, according to another of its aspects, a subject of the invention is medicaments which comprise a compound of formula (I), or an addition salt of the latter with a pharmaceutically acceptable acid.

These medicaments are of use in therapeutics, in particular in the treatment and prevention of neurodegenerative diseases such as, for example, Parkinson's disease, Alzheimer's disease, tauopathies (for example, progressive supranuclear palsy, frontotemporal dementia, corticobasal degeneration, Pick's disease); cerebral traumas such as ischaemia and cranial traumas and epilepsy; psychiatric diseases such as schizophrenia, depression, substance dependence, attention deficit hyperactivity disorders; inflammatory diseases of the central nervous system, such as multiple sclerosis, encephalitis, myelitis and encephalomyelitis and other inflammatory diseases such as vascular pathologies, atherosclerosis, joint inflammations, arthrosis, rheumatoid arthritis; osteoarthritis, Crohn's disease, ulcerous colitis; allergic inflammatory diseases such as asthma, autoimmune diseases such as type 1 diabetes, lupus, scleroderma, Guillain-Barre syndrome, Addison's disease and other immunomediated diseases; osteoporosis; cancers.

These compounds could also be used as a treatment combined with stem cell transplantations and/or grafts.

According to another of its aspects, the present invention relates to pharmaceutical compositions comprising, as active ingredient, a compound according to the invention. These pharmaceutical compositions contain an effective dose of at least one compound according to the invention, or a pharmaceutically acceptable salt of said compound, and also at least one pharmaceutically acceptable excipient.

Said excipients are chosen, according to the pharmaceutical form and the method of administration desired, from the usual excipients which are known to those skilled in the art.

In the pharmaceutical compositions of the present invention for oral, sublingual, subcutaneous, intramuscular, intravenous, topical, local, intratracheal, intranasal, transdermal or rectal administration, the active ingredient of formula (I) above, or salt thereof, may be administered in unit administration form, as a mixture with conventional pharmaceutical excipients, to animals and to humans for the prophylaxis or the treatment of the disorders or diseases above.

The suitable unit administration forms comprise oral administration forms such as tablets, soft or hard gel capsules, powders, granules and oral solutions or suspensions, sublingual, buccal, intratracheal, intraocular and intranasal administration forms, forms for administration by inhalation, topical, transdermal, subcutaneous, intramuscular or intravenous administration forms, rectal administration forms, and implants. For topical application, the compounds according to the invention may be used in creams, gels, ointments or lotions.

By way of example, a unit administration form of a compound according to the invention in tablet form may comprise the following components:

| | |
|---|---|
| Compound according to the invention | 50.0 mg |
| Mannitol | 223.75 mg |
| Sodium croscarmellose | 6.0 mg |
| Maize starch | 15.0 mg |
| Hydroxypropylmethylcellulose | 2.25 mg |
| Magnesium stearate | 3.0 mg |

There may be particular cases where higher or lower dosages are appropriate; such dosages do not depart from the context of the invention. According to the usual practice, the dosage appropriate for each patient is determined by the physician according to the method of administration and the weight and response of said patient.

According to another of its aspects, the present invention also relates to a method for treating the pathologies indicated above, which comprises the administration, to a patient, of an effective dose of a compound according to the invention, or a pharmaceutically acceptable salt thereof.

What is claimed is:
1. A compound of formula (I):

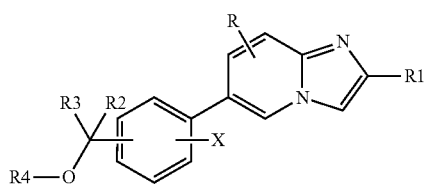

wherein:
$R_1$ represents:
  a heteroaryl or heterocyclic group, wherein this group is optionally substituted with one or more atoms or groups chosen, independently of one another, from the following atoms or groups: halogen, $(C_1$-$C_{10})$alkyl, halo$(C_1$-$C_{10})$alkyl, $(C_1$-$C_{10})$alkoxy, halo$(C_1$-$C_{10})$alkoxy, oxo, $(C_1$-$C_{10})$thioalkyl, —S(O)$(C_1$-$C_{10})$ alkyl, -S(O)$_2(C_1$-$C_{10}$-alkyl), hydroxyl, cyano, nitro, hydroxy$(C_1$-$C_{10})$alkylene, NRaRb$(C_1$-$C_{10})$alkylene, $(C_1$-$C_{10})$alkoxy$(C_1$-$C_{10})$alkyleneoxy, NRaRb, CONRaRb, SO$_2$NRaRb, NRcCORd, OC(O)NRaRb, OCO$(C_1$-$C_{10})$alkyl, NRcC(O)ORe, NRcSO$_2$Re, aryl$(C_1$-$C_{10})$alkylene, monocyclic heteroaryl and aryl, wherein the monocyclic heteroaryl and aryl are optionally substituted with one or more substituents chosen from a halogen, and a $(C_1$-$C_{10})$alkyl, halo$(C_1$-$C_{10})$alkyl, $(C_1$-$C_{10})$alkoxy, halo$(C_1$-$C_{10})$alkoxy, NRaRb, hydroxyl, oxo, nitro, cyano or OCO$(C_1$-$C_{10})$ alkyl group, and R1 is linked to the imidazo[1,2-a] pyridine by an aromatic carbon;
X represents from 1 to 4 substituents, which may be identical to or different from one another, chosen from hydrogen, a halogen, $(C_1$-$C_{10})$alkyl, $(C_1$-$C_{10})$alkoxy, NRaRb, nitro, and cyano, wherein the $(C_1$-$C_{10})$alkyl group is optionally substituted with one or more groups chosen from a halogen, $(C_1$-$C_{10})$alkoxy, $(C_1$-$C_{10})$haloalkoxy, NRaRb and hydroxyl;
R represents, at position 3, 5, 7 or 8 of the imidazo[1,2-a] pyridine, from 1 to 4 substituents, which may be identical to or different from one another, chosen from a hydrogen, a halogen, $(C_1$-$C_{10})$alkyl, halo$(C_1$-$C_{10})$alkyl, and $(C_1$-$C_{10})$alkoxy;
$R_2$ and $R_3$ represent, independently of one another,
  a hydrogen atom,
  a $(C_1$-$C_{10})$alkyl group, optionally substituted with an Rf group; or
  an aryl group, optionally substituted with one or more substituents chosen from a halogen, and a $(C_1$-$C_{10})$ alkyl, halo$(C_1$-$C_{10})$alkyl, $(C_1$-$C_{10})$alkoxy, halo$(C_1$-$C_{10})$alkoxy, NRaRb, hydroxyl, nitro or cyano group;
$R_2$ and X can form, together with the carbon atoms which bear them, a carbon-based ring containing from 5 to 7 carbon atoms;
$R_4$ represents:
  a hydrogen atom;
  a $(C_1$-$C_{10})$alkyl group, optionally substituted by an Rf group; or
  an aryl group, optionally substituted with one or more substituents chosen from a halogen, and a $(C_1$-$C_{10})$ alkyl, halo$(C_1$-$C_{10})$alkyl, $(C_1$-$C_{10})$alkoxy, halo$(C_1$-$C_{10})$alkoxy, NRaRb, hydroxyl, nitro, cyano, $(C_1$-$C_{10})$ alkyl(CO)—, CONRaRb, NRcCORd, OC(O) NRaRb, OCO$(C_1$-$C_{10})$alkyl, NRcC(O)ORe or aryl group, wherein the aryl is optionally substituted with one or more substituents chosen from a halogen, and a $(C_1$-$C_{10})$alkyl, halo$(C_1$-$C_{10})$alkyl, $(C_1$-$C_{10})$alkoxy, halo$(C_1$-$C_{10})$alkoxy, NRaRb, hydroxyl, nitro or cyano group;
Ra and Rb represent, independently of one another, a hydrogen atom or a $(C_1$-$C_{10})$alkyl, aryl$(C_1$-$C_{10})$alkylene or aryl group;
or Ra and Rb form, together with the nitrogen atom which bears them, an azetidine, pyrrolidine, piperidine, azepine, morpholine, thiomorpholine, piperazine or homopiperazine group, this group being optionally substituted with a $(C_1$-$C_{10})$alkyl, aryl or aryl$(C_1$-$C_{10})$alkylene group;
Rc and Rd represent, independently of one another, a hydrogen atom or a $(C_1$-$C_{10})$alkyl, aryl$(C_1$-$C_{10})$alkylene or aryl group,
or Rc and Rd together form a $(C_2$-$C_5)$alkylene group;
Re represents a $(C_1$-$C_{10})$alkyl, aryl$(C_1$-$C_{10})$alkylene or aryl group,
or Rc and Re together form a $(C_2$-$C_5)$alkylene group; and
Rf represents a halogen atom, or a $(C_1$-$C_{10})$alkoxy, halo $(C_1$-$C_{10})$alkoxy, hydroxyl, cyano, NRaRb, C(O) NRaRb, NRcCORd, OC(O)NRaRb, OCO$(C_1$-$C_{10})$ alkyl, NRcCOORe, SO$_2$NRaRb, NRcSO$_2$Re, aryl$(C_1$-$C_{10})$alkylene or aryl group, wherein the aryl is optionally substituted with one or more substituents chosen from a halogen, and a $(C_1$-$C_{10})$alkyl, halo$(C_1$-$C_{10})$alkyl, $(C_1$-$C_{10})$alkoxy, halo$(C_1$-$C_{10})$alkoxy, NRaRb, hydroxyl, nitro, cyano or OCO$(C_1$-$C_{10})$alkyl group;
or an acid addition salt thereof.
2. The compound of formula (I) according to claim 1, wherein:
$R_1$ represents an isoxazolyl, pyridinyl, thiazolyl, quinolinyl, benzo[1,3]dioxolyl, indolyl, 1,2,3,4-tetrahydroquinolinyl, benzofuranyl, dihydrobenzofuranyl, dihydrobenzoxazolyl, furyl, thienyl, pyrrolo[2,3-b] pyridinyl, pyrimidinyl, benzothiazolyl, benzothiophenyl, benzimidazolyl, indazolyl, benzisoxazolyl, isoquinolinyl or pyrazolyl group;
wherein these groups are optionally substituted with one or more atoms or groups chosen, independently of one another, from halogen, $(C_1-C_{10})$alkyl, oxo, NRaRb, $(C_1-C_{10})$alkoxy, aryl and CONRaRb; and Ra and Rb represent, independently of one another, a hydrogen atom or a $(C_1-C_{10})$alkyl group;

or an acid addition salt thereof.

3. The compound of formula (I) according to claim 1, wherein X represents 1 or 2 hydrogen or halogen atoms;
or an acid addition salt thereof.

4. The compound of formula (I) according to claim 1, wherein R represents, at position 3, 5, 7 or 8 of the imidazo[1,2-a]pyridine, a hydrogen atom or a $(C_1-C_{10})$alkyl group;
or an acid addition salt thereof.

5. The compound of formula (I) according to claim 1, wherein $R_2$ and $R_3$ represent, independently of one another, a hydrogen atom or a $(C_1-C_{10})$alkyl group;
or an acid addition salt thereof.

6. The compound of formula (I) according to claim 1, wherein:
$R_4$ represents a hydrogen atom, or a $(C_1-C_{10})$alkyl group optionally substituted with an Rf group; and
Rf represents a $(C_1-C_{10})$alkoxy group;
or an acid addition salt thereof.

7. The compound of formula (I) according to claim 1, wherein:
the group

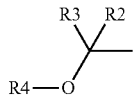

is at position 2, 3 or 4 of the phenyl which bears it;
or an acid addition salt thereof.

8. The compound of formula (I) according to claim 1, wherein:
$R_1$ represents an isoxazolyl, pyridinyl, thiazolyl, quinolinyl, benzo[1,3]dioxolyl, indolyl, 1,2,3,4-tetrahydroquinolinyl, benzofuranyl, dihydrobenzofuranyl, dihydrobenzoxazolyl, furyl, thienyl, pyrrolo[2,3-b]pyridinyl, pyrimidinyl, benzothiazolyl, benzothiophenyl, benzimidazolyl, indazolyl, benzisoxazolyl, isoquinolinyl or pyrazolyl group;
wherein these groups are optionally substituted with one or more atoms or groups chosen, independently of one another, from halogen, $(C_1-C_{10})$alkyl, oxo, NRaRb, $(C_1-C_{10})$alkoxy, aryl and CONRaRb;
Ra and Rb represent, independently of one another, a hydrogen atom or a $(C_1-C_{10})$alkyl group;
X represents 1 or 2 hydrogen or halogen atoms;
R represents, at position 3, 5, 7 or 8 of the imidazo[1,2-a]pyridine, a hydrogen atom or a $(C_1-C_{10})$alkyl group;
$R_2$ and $R_3$ represent, independently of one another, a hydrogen atom or a $(C_1-C_{10})$alkyl group;
$R_4$ represents a hydrogen atom, or a $(C_1-C_{10})$alkyl group optionally substituted with an Rf group; and
Rf represents a $(C_1-C_{10})$alkoxy group;
or an acid addition salt thereof.

9. The compound of formula (I) according to claim 1, wherein:
$R_1$ represents an isoxazolyl, pyridinyl, thiazolyl, quinolinyl, benzo[1,3]dioxolyl, indolyl, 1,2,3,4-tetrahydroquinolinyl, benzofuranyl, dihydrobenzofuranyl, dihydrobenzoxazolyl, furyl, thienyl, pyrrolo[2,3-b]pyridinyl, pyrimidinyl, benzothiazolyl, benzothiophenyl, benzimidazolyl, indazolyl, benzisoxazolyl, isoquinolinyl or pyrazolyl group;
wherein these groups are optionally substituted with one or more atoms or groups chosen, independently of one another, from halogen, $(C_1-C_{10})$alkyl, oxo, NRaRb, $(C_1-C_{10})$alkoxy, aryl and CONRaRb;
Ra and Rb represent, independently of one another, a hydrogen atom or a $(C_1-C_{10})$alkyl group;
X represents 1 or 2 hydrogen or halogen atoms;
R represents, at position 3, 5, 7 or 8 of the imidazo[1,2-a]pyridine, a hydrogen atom or a $(C_1-C_{10})$alkyl group;
$R_2$ and $R_3$ represent, independently of one another, a hydrogen atom or a $(C_1-C_{10})$alkyl group;
$R_4$ represents a hydrogen atom, or a $(C_1-C_{10})$alkyl group optionally substituted with an Rf group;
Rf represents a $(C_1-C_{10})$alkoxy group; and
the group

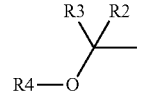

being at position 2, 3 or 4 of the phenyl which bears it;
or an acid addition salt thereof.

10. The compound of formula (I)according to claim 1 wherein:
$R_1$ represents an isoxazolyl, pyridinyl, thiazolyl, quinolinyl, benzo[1,3]dioxolyl, indolyl, 1,2,3,4-tetrahydroquinolinyl, benzofuranyl, dihydrobenzofuranyl, dihydrobenzoxazolyl, furyl, thienyl or pyrrolo[2,3-b]pyridinyl group, wherein these groups are optionally substituted with one or more atoms or groups chosen, independently of one another, from halogen, $(C_1-C_{10})$alkyl, oxo, NRaRb and aryl;
X represents a hydrogen;
R represents a hydrogen or a $(C_1-C_{10})$alkyl group;
$R_2$ and $R_3$ represent, independently of one another, a hydrogen atom;
$R_4$ represents a hydrogen atom or a $(C_1-C_{10})$alkyl group, this group being optionally substituted with an Rf group;
Ra and Rb represent, independently of one another, a hydrogen atom or a $(C_1-C_{10})$alkyl group; and
Rf represents a $(C_1-C_{10})$alkoxy group;
or an acid addition salt thereof.

11. A compound selected from the group consisting of:
{3]2-(5-methylisoxazol-4-yl)imidazo[1,2-a]pyridin-6-yl]phenyl}methanol;
[3-[2-(pyridin-4-yl)imidazo[1,2-a]pyridin-6-yl]phenyl]methanol and the hydrochloride thereof;
6-(3-tert-butoxymethylphenyl)-2-(pyridin-3-yl)imidazo[1,2-a]pyridine hydrochloride (1:2);
[3-[2-(thiazol-4-yl)imidazo[1,2-a]pyridin-6-yl]phenyl]methanol;
[3-[2-(quinolin-3-yl)imidazo[1,2-a]pyridin-6-yl]phenyl]methanol and the hydrochloride thereof;
{3-[2-(1,3-benzodioxol-5-yl)imidazo[1,2-a]pyridin-6-yl]phenyl}methanol and the hydrochloride thereof;
[3-[2-(pyridin-3-yl)imidazo[1,2-a]pyridin-6-yl]phenyl]methanol and the hydrochloride thereof;
{3-[2-[(1H-indol5-yl)imidazo[1,2-a]pyridin-6-yl]phenyl}methanol and the hydrochloride thereof;
6-[6-(3-hydroxymethylphenyl)imidazo[1,2-a]pyridin-2-yl]-3,4-dihydro-1H-quinolin-2-one and the hydrochloride thereof;
2-(5-bromo-2,3-dihydrobenzofuran-7-yl)-6-(3-tert-butoxymethylphenyl)imidazo[1,2-a]pyridine;

6-[6-(3-hydroxymethylphenyl)imidazo[1,2-a]pyridin-2-yl]-3H-benzoxazol-2-one and the hydrochloride thereof;
[2-(2-furan-3-ylimidazo[1,2-a]pyridin-6-yl)phenyl]methanol hydrochloride (1:1);
{3-[2-(5-bromo-2,3-dihydrobenzofuran-7-yl)imidazo[1,2-a]pyridin-6-yl]phenyl}methanol;
{3-[2-(5-chlorothien-2-yl)imidazo[1,2-a]pyridin-6-yl]phenyl}methanol and the hydrochloride thereof;
{3-[2-(6-dimethylaminopyridin-3-yl)imidazo[1,2-a]pyridin-6-yl]phenyl}methanol and the hydrochloride thereof;
{3-[2-(1H-indol-4-yl)imidazo[1,2-a]pyridin-6-yl]phenyl}methanol and the hydrochloride thereof;
{3-[2-(6-aminopyridin-3-yl)imidazo[1,2-a]pyridin-6-yl]phenyl} methanol and the hydrochloride thereof;
{3-[2-(1H-indol-3-yl)imidazo[1,2-a]pyridin-6-yl]phenyl}methanol and the hydrochloride thereof;
{3-[2-(2-aminopyridin-3-yl)imidazo[1,2-a]pyridin-6-yl]phenyl}methanol and the hydrochloride thereof;
{3-[2-(1H-pyrrolo[2,3-b]pyridin-5-yl)imidazo[1,2-a]pyridin-6-yl]phenyl}methanol and the hydrochloride thereof;
{3-[2-(3-phenylisoxazol-5-yl)imidazo[1,2-a]pyridin-6-yl]phenyl}methanol;
[3-[2-(benzofuran-2-yl)imidazo[1,2-a]pyridin-6-yl]phenyl]methanol;
[3-[2-(benzofuran-3-yl)imidazo[1,2-a]pyridin-6-yl]phenyl]methanol;
[4-[2-(benzofuran-3-yl)imidazo[1,2-a]pyridin-6-yl]phenyl]methanol;
[3-[2-(pyridin-2-yl)imidazo[1,2-a]pyridin-6-yl]phenyl]methanol;
[4-[2-(pyridin-2-yl]imidazo[1,2-a]pyridin-6-yl]phenyl]methanol;
[3-[2-(thien-2-yl)imidazo[1,2-a]pyridin-6-yl]phenyl]methanol;
2-(benzofuran-2-yl)-6-[3-(2-methoxyethoxymethyl)phenyl]imidazo[1,2-a]pyridine;
6-[3-(2-methoxyethoxymethyl)phenyl]-2-(thien-2-yl)imidazo[1,2-a]pyridine and the oxalate thereof;
[3-(2-thien-3-ylimidazo[1,2-a]pyridin-6-yl)phenyl]methanol;
[3-(3-methyl-2-thien-2-ylimidazo[1,2-a]pyridin-6-yl)phenyl]methanol and the hydrochloride thereof;
{3-[2-(1H-indol-3-yl)-3-methylimidazo[1,2-a]pyridin-6-yl]phenyl}methanol and the hydrochloride thereof;
{3-[2-(1H-indol-6-yl)imidazo[1,2-a]pyridin-6-yl]phenyl}methanol and the hydrochloride thereof;
{3-[2-(2-ethoxypyrimidin-5-yl)imidazo[1,2-a]pyridin-6-yl]phenyl}methanol and the hydrochloride thereof;
[2-(2-quinolin-3-ylimidazo[1,2-a]pyridin-6-yl)phenyl]methanol and the hydrochloride thereof;
{3-[2-(2-chloropyridin-4-yl)imidazo[1,2-a]pyridin-6-yl]phenyl}methanol and the hydrochloride thereof;
[3-(2-benzothiazol-2-ylimidazo[1,2-a]pyridin-6-yl)phenyl]methanol and the hydrochloride thereof;
[3-(2-benzo[b]thiophen-2-ylimidazo[1,2-a]pyridin-6-yl)phenyl]methanol and the hydrochloride thereof;
[3-(2-benzo[b]thiophen-5-ylimidazo[1,2-a]pyridin-6-yl)phenyl]methanol and the hydrochloride thereof;
3-(2-benzo[b]thiophen-3-ylimidazo[1,2-a]pyridin-6-yl)phenyl]methanol and the hydrochloride thereof;
{2-[2-(1H-indol-6-yl)imidazo[1,2-a]pyridin-6-yl]phenyl}methanol and the hydrochloride thereof;
{3-[2-(2,3-dihydrobenzofuran-5-yl)imidazo[1,2-a]pyridin-6-yl]phenyl}methanol and the hydrochloride thereof;
{2-[2-(1H-indol-5-yl)imidazo[1,2-a]pyridin-6-yl]phenyl}methanol and the hydrochloride thereof;
[3-(2-benzofuran-5-ylimidazo[1,2-a]pyridin-6-yl)phenyl]methanol;
{3-[2-(3-chlorothien-2-yl)imidazo[1,2-a]pyridin-6-yl]phenyl}methanol;
{2-fluoro-6-[2-(5-methylisoxazol-3-yl)imidazo[1,2-a]pyridin-6-yl]phenyl}methanol;
2-{3-[2-(1H-indol-6-yl)imidazo[1,2-a]pyridin-6-yl]phenyl}propan-2-ol;
2-[3-(3-methyl-2-thien-2-ylimidazo[1,2-a]pyridin-6-yl)phenyl]propan-2-ol;
2-[3-(2-thien-3-ylimidazo[1,2-a]pyridin-6-yl)phenyl]propan-2-ol;
2-[3-(2-pyridin-2-ylimidazo[1,2-a]pyridin-6-yl)phenyl]propan-2-ol;
2-{3-[2-(5-chlorothien-2-yl)imidazo[1,2-a]pyridin-6-yl]phenyl}propan-2-ol;
2-[3-(2-benzofuran-2-ylimidazo[1,2-a]pyridin-6-yl)phenyl]propan-2-ol;
2-[3-(2-thien-2-ylimidazo[1,2-a]pyridin-6-yl)phenyl]propan-2-ol;
2-[3-(2-benzofuran-3-ylimidazo[1,2-a]pyridin-6-yl)phenyl]propan-2-ol;
2-[3-(2-benzothiazol-2-ylimidazo[1,2-a]pyridin-6-yl)phenyl]propan-2-ol;
2-[3-(2-benzo[b]thienyl-2-ylimidazo[1,2-a]pyridin-6-yl)phenyl]propan-2-ol;
2-{3-[2-(1-methyl-1H-benzimidazol-2-yl)imidazo[1,2-a]pyridin-6-yl]phenyl}propan-2-ol;
2-{3-[2-(2,3-dihydrobenzofuran-5-yl)imidazo[1,2-a]pyridin-6-yl]phenyl}propan-2-ol;
2-[3-(2-furan-2-ylimidazo[1,2-a]pyridin-6-yl)phenyl]propan-2-ol;
2-[3-(2-benzofuran-5-ylimidazo[1,2-a]pyridin-6-yl)phenyl]propan-2-ol;
2-[3-(2-benzo[b]thienyl-5-ylimidazo[1,2-a]pyridin-6-yl)phenyl]propan-2-ol;
2-[3-(2-thiazol-2-ylimidazo[1,2-a]pyridin-6-yl)phenyl]propan-2-ol;
{2-fluoro-6-[2-(1H-indazol-3-yl)imidazo[1,2-a]pyridin-6-yl]phenyl}methanol and the hydrochloride thereof;
2-{3-[2-(1H-indazol-3-yl)imidazo[1,2-a]pyridin-6-yl]phenyl}propan-2-ol and the hydrochloride thereof;
{2,6-difluoro-3-[2-(1H-indazol-3-yl)imidazo[1,2-a]pyridin-6-yl]phenyl}methanol and the hydrochloride thereof;
[2-fluoro-6-(2-thien-3-ylimidazo[1,2-a]pyridin-6-yl)phenyl]methanol;
[2-fluoro-6-(2-pyridin-2-ylimidazo[1,2-a]pyridin-6-yl)phenyl]methanol;
[2-fluoro-6-(2-thien-2-ylimidazo[1,2-a]pyridin-6-yl)phenyl]methanol;
[2-(2-benzothiazol-2-ylimidazo[1,2-a]pyridin-6-yl)-6-fluorophenyl]methanol;
[2-(2-benzo[b]thiophen-2-ylimidazo[1,2-a]pyridin-6-yl)-6-fluorophenyl]methanol;
{2-[2-(2,3-dihydrobenzofuran-5-yl)imidazo[1,2-a]pyridin-6-yl]-6-fluorophenyl}methanol;
[2-(2-benzofuran-5-ylimidazo[1,2-a]pyridin-6-yl)-6-fluorophenyl]methanol;
[2-(2-benzo[b]thienyl-5-ylimidazo[1,2-a]pyridin-6-yl)-6-fluorophenyl]methanol;

[2-fluoro-6-(2-thiazol-2-ylimidazo[1,2-a]pyridin-6-yl) phenyl]methanol;
[2,6-difluoro-3-(3-methyl-2-thien-2-ylimidazo[1,2-a]pyridin-6-yl)phenyl]methanol;
[2,6-difluoro-3-(2-thien-3-ylimidazo[1,2-a]pyridin-6-yl) phenyl]methanol;
[2,6-difluoro-3-(2-pyridin-2-ylimidazo[1,2-a]pyridin-6-yl)phenyl]methanol;
{3-[2-(5-chlorothien-2-yl)imidazo[1,2-a]pyridin-6-yl]-2,6-difluorophenyl}methanol;
[3-(2-benzofuran-2-ylimidazo[1,2-a]pyridin-6-yl)-2,6-difluorophenyl]methanol;
[2,6-difluoro-3-(2-thien-2-ylimidazo[1,2-a]pyridin-6-yl) phenyl]methanol;
[3-(2-benzofuran-3-ylimidazo[1,2-a]pyridin-6-yl)-2,6-difluorophenyl]methanol;
[3-(2-benzothiazol-2-ylimidazo[1,2-a]pyridin-6-yl)-2,6-difluorophenyl]methanol;
[2,6-difluoro-3-(2-thiazol-2-ylimidazo[1,2-a]pyridin-6-yl)phenyl]methanol;
6-(3-methoxymethylphenyl)-2-(1-methyl-1H-indol-6-yl) imidazo[1,2-a]pyridine and the hydrochloride thereof;
2-(1H-indol-6-yl)-6-(3-methoxymethylphenyl)imidazo[1,2-a]pyridine and the hydrochloride thereof;
2-{3-[2-(5-methylisoxazol-3-yl)imidazo[1,2-a]pyridin-6-yl]phenyl}propan-2-ol;
[2-fluoro-6-(3-methyl-2-thienyl-2-ylimidazo[1,2-a]pyridin-6-yl)phenyl]methanol;
{2-[2-(5-chlorothiophen-2-yl)imidazo[1,2-a]pyridin-6-yl]-6-fluorophenyl}methanol;
[2-(2-benzofuran-2-ylimidazo[1,2-a]pyridin-6-yl)-6-fluorophenyl]methanol;
[2-(2-benzofuran-3-ylimidazo[1,2-a]pyridin-6-yl)-6-fluorophenyl]methanol;
{2-fluoro-6-[2-(1-methyl-1H-benzimidazol-2-yl)imidazo[1,2-a]pyridin-6-yl]phenyl}methanol;
[2-fluoro-6-(2-furan-2-ylimidazo[1,2-a]pyridin-6-yl)phenyl]methanol;
[3-(2-benzo[b]thienyl-2-ylimidazo[1,2-a]pyridin-6-yl)-2,6-difluorophenyl]methanol;
{2,6-difluoro-3-[2-(1-methyl-1H-benzimidazol-2-yl)imidazo[1,2-a]pyridin-6-yl]phenyl}methanol;
{3-[2-(2,3-dihydrobenzofuran-5-yl)imidazo[1,2-a]pyridin-6-yl]-2,6-difluorophenyl}methanol;
[2,6-difluoro-3-(2-furan-2-ylimidazo[1,2-a]pyridin-6-yl) phenyl]methanol;
[3-(2-benzofuran-5-ylimidazo[1,2-a]pyridin-6-yl)-2,6-difluorophenyl]methanol;
[3-(2-benzo[b]thienyl-5-ylimidazo[1,2-a]pyridin-6-yl)-2,6-difluorophenyl]methanol;
2-(1H-indol-6-yl)-6-[3-[2-(methoxyethyl)oxymethyl] phenyl]imidazo[1,2-a]pyridine;
2-[3-(2-benzo[d]isoxazol-3-ylimidazo[1,2-a]pyridin-6-yl)phenyl]propan-2-ol;
[2-(2-benzo[d]isoxazol-3-ylimidazo[1,2-a]pyridin-6-yl)-6-fluorophenyl]methanol;
2-{3-[2-(1H-indol-5-yl)imidazo[1,2-a]pyridin-6-yl] phenyl}propan-2-ol;
2-{3-[2-(1H-indol-4-yl)imidazo[1,2-a]pyridin-6-yl] phenyl}propan-2-ol;
2-{3-[2-(2-methoxypyridin-3-yl)imidazo[1,2-a]pyridin-6-yl]phenyl}propan-2-ol;
2-{3-[2-(4-methylthien-3-yl)imidazo[1,2-a]pyridin-6-yl] phenyl}propan-2-ol;
2-{3-[2-(1-methyl-1H-indol-5-yl)imidazo[1,2-a]pyridin-6-yl]phenyl}propan-2-ol;
2-[3-(2-quinolin-5-ylimidazo[1,2-a]pyridin-6-yl)phenyl] propan-2-ol;
2-[3-(2-isoquinolin-5-ylimidazo[1,2-a]pyridin-6-yl)phenyl]propan-2-ol;
2-{3-[2-(2,6-difluoropyridin-4-yl)imidazo[1,2-a]pyridin-6-yl]phenyl}propan-2-ol;
2-(3-{2-[1-(3-methylbutyl)-1H-pyrazol-4-yl]imidazo[1,2-a]pyridin-6-yl}phenyl)propan-2-ol;
2-[3-(2-quinolin-3-ylimidazo[1,2-a]pyridin-6-yl)phenyl] propan-2-ol;
{2-fluoro-6-[2-(1H-indol-5-yl)imidazo[1,2-a]pyridin-6-yl]phenyl}methanol;
{2-fluoro-6-[2-(6-methoxypyridin-3-yl)imidazo[1,2-a] pyridin-6-yl]phenyl}methanol;
{2-fluoro-6-[2-(3-fluoropyridin-4-yl)imidazo[1,2-a]pyridin-6-yl]phenyl}methanol;
{2-fluoro-6-[2-(4-methylthien-2-yl)imidazo[1,2-a]pyridin-6-yl]phenyl}methanol;
[2-fluoro-6-(2-pyrimidin-5-ylimidazo[1,2-a]pyridin-6-yl) phenyl]methanol;
{2-fluoro-6-[2-(1H-indol-4-yl)imidazo[1,2-a]pyridin-6-yl]phenyl}methanol;
{2-fluoro-6-[2-(1H-indol-6-yl)imidazo[1,2-a]pyridin-6-yl]phenyl}methanol;
{2-fluoro-6-[2-(2-methoxypyridin-3-yl)imidazo[1,2-a] pyridin-6-yl]phenyl}methanol;
{2-fluoro-6-[2-(4-methylthien-3-yl)imidazo[1,2-a]pyridin-6-yl]phenyl}methanol;
{2-fluoro-6-[2-(1-methyl-1H-indol-5-yl)imidazo[1,2-a] pyridin-6-yl]phenyl}methanol;
[2-fluoro-6-(2-quinolin-5-ylimidazo[1,2-a]pyridin-6-yl) phenyl]methanol;
[2-fluoro-6-(2-isoquinolin-5-ylimidazo[1,2-a]pyridin-6-yl)phenyl]methanol;
{2-[2(2,6-difluoropyridin-4-yl)imidazo[1,2-a]pyridin-6-yl]-6-fluorophenyl}methanol;
(2-fluoro-6-{2-[1-(3-methylbutyl)-1H-pyrazol-4-yl]imidazo[1,2-a]pyridin-6-yl}phenyl)methanol;
{2,6-difluoro-3-[2-(1H-indol-5-yl)imidazo[1,2-a]pyridin-6-yl]phenyl}methanol;
{2,6-difluoro-3-[2-(6-methoxypyridin-3-yl)imidazo[1,2-a]pyridin-6-yl]phenyl}methanol;
{2,6-difluoro-3-[2-(4-methylthien-2-yl)imidazo[1,2-a] pyridin-6-yl]phenyl}methanol;
{2,6-difluoro-3-[2-(1H-indol-6-yl)imidazo[1,2-a]pyridin-6-yl]phenyl}methanol;
{2,6-difluoro-3-[2-(2-methoxypyridin-3-yl)imidazo[1,2-a]pyridin-6-yl]phenyl}methanol;
{2,6-difluoro-3-[2-(4-methylthien-3-yl)imidazo[1,2-a] pyridin-6-yl]phenyl}methanol;
{2,6-difluoro-3-[2-(1-methyl-1H-indol-5-yl)imidazo[1,2-a]pyridin-6-yl]phenyl}methanol;
[2,6-difluoro-3-(2-quinolin-5-ylimidazo[1,2-a]pyridin-6-yl)phenyl]methanol;
[2,6-difluoro-3-(2-isoquinolin-5-ylimidazo[1,2-a]pyridin-6-yl)phenyl]methanol;
{3-2-(2,6-difluoropyridin-4-yl)imidazo[1,2-a]pyridin-6-yl]-2,6-difluorophenyl}methanol;
(2,6-difluoro-3-{2-[1-(3-methylbutyl)-1H-pyrazol-4-yl] imidazo[1,2-a]pyridin-6-yl}phenyl)methanol; and
N-tert-butyl-5-[6-(2,4-difluoro-3-hydroxymethylphenyl) imidazo[1,2-a]pyridin-2-yl]nicotinamide.

12. A pharmaceutical composition comprising a compound of formula (I) according to claim 1, or a pharmaceutically acceptable salt thereof, and one or more pharmaceutically acceptable excipients.

13. A pharmaceutical composition comprising a compound of formula (I) according to claim 11, or a pharmaceutically acceptable salt thereof, and one or more pharmaceutically acceptable excipients.
14. A compound selected from the group consisting of:
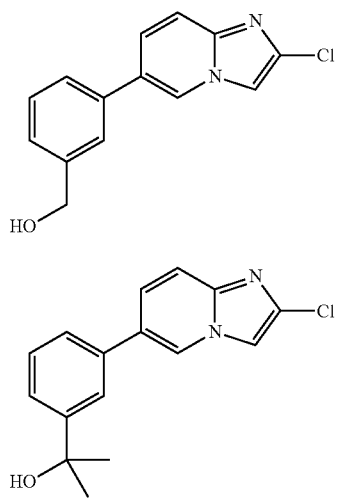
(IX-1)
(IX-2)
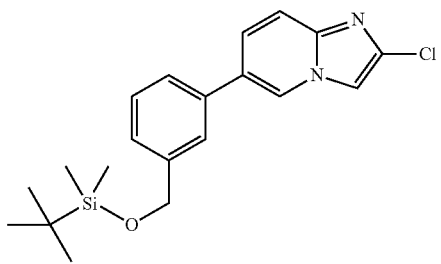
(XI-1) and
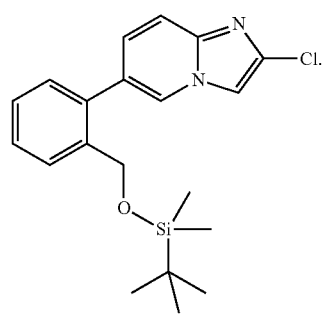
(XI-2)
* * * * *

UNITED STATES PATENT AND TRADEMARK OFFICE
CERTIFICATE OF CORRECTION

| | | |
|---|---|---|
| PATENT NO. | : 8,338,451 B2 | Page 1 of 1 |
| APPLICATION NO. | : 12/881815 | |
| DATED | : December 25, 2012 | |
| INVENTOR(S) | : De Peretti et al. | |

It is certified that error appears in the above-identified patent and that said Letters Patent is hereby corrected as shown below:

In the Claims:

In column 80, line 26, in claim 10, delete "(I)according" and insert -- (I) according --, therefor.

In column 80, line 26, in claim 10, delete "1" and insert -- 1, --, therefor.

In column 80, line 47, in claim 11, delete "{3]2" and insert -- {3-[2 --, therefor.

In column 80, line 61, in claim 11, delete "indol5" and insert -- indol-5 --, therefor.

In column 81, line 10, in claim 11, delete "[2(6" and insert -- [2-(6 --, therefor.

In column 81, line 40, in claim 11, delete "6[3" and insert -- 6-[3 --, therefor.

In column 84, line 36, in claim 11, delete "[2(2," and insert -- [2-(2, --, therefor.

In column 84, line 58, in claim 11, delete "{3-2" and insert -- {3-[2 --, therefor.

Signed and Sealed this
Eleventh Day of June, 2013

Teresa Stanek Rea
*Acting Director of the United States Patent and Trademark Office*